(12) United States Patent
Saulnier et al.

(10) Patent No.: US 9,775,831 B2
(45) Date of Patent: Oct. 3, 2017

(54) COMBINATIONS COMPRISING BIPHENYL DERIVATIVES FOR USE IN THE TREATMENT OF HCV

(71) Applicant: BRISTOL-MYERS SQUIBB COMPANY, Princeton, NJ (US)

(72) Inventors: Mark G. Saulnier, Higganum, CT (US); David B. Frennesson, Naugatuck, CT (US); Makonen Belema, North Haven, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/904,852

(22) PCT Filed: Jul. 15, 2014

(86) PCT No.: PCT/US2014/046733
§ 371 (c)(1),
(2) Date: Jan. 13, 2016

(87) PCT Pub. No.: WO2015/009744
PCT Pub. Date: Jan. 22, 2015

(65) Prior Publication Data
US 2016/0166545 A1    Jun. 16, 2016

Related U.S. Application Data

(60) Provisional application No. 61/847,440, filed on Jul. 17, 2013.

(51) Int. Cl.
| | |
|---|---|
| *A61K 31/415* | (2006.01) |
| *A61K 31/4178* | (2006.01) |
| *A61K 38/21* | (2006.01) |
| *A61K 45/06* | (2006.01) |
| *A61K 31/422* | (2006.01) |
| *A61K 31/454* | (2006.01) |
| *A61K 31/496* | (2006.01) |
| *A61K 31/5377* | (2006.01) |
| *A61K 31/7056* | (2006.01) |
| *C07D 401/14* | (2006.01) |
| *C07D 405/14* | (2006.01) |
| *C07D 317/32* | (2006.01) |
| *C07D 233/64* | (2006.01) |
| *C07D 403/14* | (2006.01) |
| *C07D 487/04* | (2006.01) |
| *A61K 31/4545* | (2006.01) |

(52) U.S. Cl.
CPC ........ *A61K 31/4178* (2013.01); *A61K 31/422* (2013.01); *A61K 31/454* (2013.01); *A61K 31/4545* (2013.01); *A61K 31/496* (2013.01); *A61K 31/5377* (2013.01); *A61K 31/7056* (2013.01); *A61K 38/21* (2013.01); *A61K 45/06* (2013.01); *C07D 233/64* (2013.01); *C07D 317/32* (2013.01); *C07D 401/14* (2013.01); *C07D 403/14* (2013.01); *C07D 405/14* (2013.01); *C07D 487/04* (2013.01)

(58) Field of Classification Search
CPC .................................................. A61K 31/4178
USPC ........................................................ 514/397
See application file for complete search history.

(56) References Cited

U.S. PATENT DOCUMENTS

| | | |
|---|---|---|
| 5,654,451 A | 8/1997 | Kari |
| 7,745,636 B2 | 6/2010 | Bachand et al. |
| 7,894,996 B2 | 2/2011 | Rice et al. |
| 8,288,562 B2 | 10/2012 | Bachand et al. |
| 8,303,944 B2 | 11/2012 | Bachand et al. |
| 8,492,553 B2 | 7/2013 | Bachand et al. |
| 8,574,563 B2 | 11/2013 | Bachand et al. |
| 8,618,153 B2 | 12/2013 | Bender et al. |
| 8,642,025 B2 | 2/2014 | Bachand et al. |
| 8,735,398 B2 | 5/2014 | Lopez et al. |
| 8,846,023 B2 | 9/2014 | Bachand et al. |
| 8,900,566 B2 | 12/2014 | Belema et al. |
| 9,006,455 B2 | 4/2015 | Pack et al. |
| 9,018,390 B2 | 4/2015 | Bachand et al. |
| 9,227,961 B2 | 1/2016 | Bachand et al. |
| 9,303,007 B2 | 4/2016 | Lopez |
| 9,340,520 B2 | 5/2016 | Lopez et al. |
| 9,561,212 B2 | 2/2017 | Romine et al. |
| 2010/0158862 A1 | 6/2010 | Kim et al. |
| 2011/0092415 A1 | 4/2011 | DeGoey et al. |
| 2011/0206637 A1 | 8/2011 | Or et al. |
| 2011/0218175 A1 | 9/2011 | Or et al. |
| 2011/0237636 A1 | 9/2011 | Belema et al. |

(Continued)

FOREIGN PATENT DOCUMENTS

| | | |
|---|---|---|
| WO | WO94/15909 | 7/1994 |
| WO | WO2004/005264 A2 | 1/2004 |

(Continued)

OTHER PUBLICATIONS

Lemm, et al., "Identification of Hepatitis C Virus NS5A Inhibitors," J. Virology, 84, pp. 482-491 (2010).
Gao, et al., Chemical Genetics Strategy Identifies an HCV NS5A Inhibitor with a Potent Clinical Effect, Nature, 465, pp. 96-100 (2010).
Fridell, et al., "Resistance Analysis of the Hepatitis C Virus NS5A Inhibitor BMS-790052 in an In Vitro Replicon System," Antimicrob. Agents Chemother., 54, pp. 3641-3650 (2010).
Romine, et al. "Inhibitors of HCV NS5A: From Iminothiazolidinones to Symmetrical Stilbenes," ACS Med. Chem. Lett., 2, pp. 224-229 (2011).
O'Boyle, et al., "Development of a Cell-based High-Throughput Specificity Screen Using a HCV/BVDV Dual Replicon Assay," Antimicrob. Agents Chemother., 49, pp. 1346-1353 (2005).

(Continued)

*Primary Examiner* — Shengjun Wang
(74) *Attorney, Agent, or Firm* — Pamela A. Mingo

(57) ABSTRACT

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

12 Claims, No Drawings

(56) References Cited

U.S. PATENT DOCUMENTS

| | | | |
|---|---|---|---|
| 2011/0250176 A1* | 10/2011 | Lemm | A61K 31/4178 424/85.7 |
| 2011/0268697 A1 | 11/2011 | Kim et al. | |
| 2013/0071352 A1 | 3/2013 | Dousson et al. | |
| 2013/0072523 A1 | 3/2013 | Liu et al. | |
| 2013/0072690 A1 | 3/2013 | Chen et al. | |
| 2013/0115193 A1 | 5/2013 | Lavoie et al. | |
| 2013/0157894 A1* | 6/2013 | Sun | C12Q 1/18 506/9 |
| 2013/0183269 A1* | 7/2013 | Hewawasam | A61K 31/407 424/85.5 |
| 2013/0259832 A1 | 10/2013 | Lemm et al. | |
| 2014/0018389 A1 | 1/2014 | Lavoie et al. | |
| 2014/0205564 A1 | 7/2014 | Romine et al. | |
| 2015/0023913 A1 | 1/2015 | Hewawasam et al. | |
| 2015/0297568 A1 | 10/2015 | Hewawasam et al. | |
| 2015/0322048 A1 | 11/2015 | Lavoie et al. | |
| 2015/0335655 A1 | 11/2015 | Gao et al. | |
| 2016/0067223 A1 | 3/2016 | Belema et al. | |
| 2016/0199355 A1 | 7/2016 | Hewawasam et al. | |
| 2016/0311778 A1 | 10/2016 | Bachand et al. | |

FOREIGN PATENT DOCUMENTS

| | | |
|---|---|---|
| WO | WO2006/022442 A1 | 3/2006 |
| WO | WO2006093867 A1 | 9/2006 |
| WO | WO2006/133326 A1 | 12/2006 |
| WO | WO2007/031791 A1 | 3/2007 |
| WO | WO2007/058384 A1 | 5/2007 |
| WO | WO2007/076034 A2 | 7/2007 |
| WO | WO2007/077186 A1 | 7/2007 |
| WO | WO 2007/081517 A2 | 7/2007 |
| WO | WO2007/138242 A1 | 12/2007 |
| WO | WO2008/021927 A2 | 2/2008 |
| WO | WO2008/021936 A2 | 2/2008 |
| WO | WO2008021928 A2 | 2/2008 |
| WO | WO 2008/070447 A2 | 6/2008 |
| WO | WO2008/133753 A2 | 11/2008 |
| WO | WO2008/144380 A1 | 11/2008 |
| WO | WO2009/020825 A1 | 2/2009 |
| WO | WO2009/020828 A1 | 2/2009 |
| WO | WO2009/102568 A1 | 8/2009 |
| WO | WO2009/102633 A1 | 8/2009 |
| WO | WO2009/102694 A2 | 8/2009 |
| WO | WO 2010/017401 A1 | 2/2010 |
| WO | WO 2010/039793 A1 | 4/2010 |
| WO | WO2010/062821 A1 | 6/2010 |
| WO | WO 2010/065668 A1 | 6/2010 |
| WO | WO2010/065674 A1 | 6/2010 |
| WO | WO2010/065681 A1 | 6/2010 |
| WO | WO2010/075376 A2 | 7/2010 |
| WO | WO2010/091413 A1 | 8/2010 |
| WO | WO2010/094977 A1 | 8/2010 |
| WO | WO2010/096302 A1 | 8/2010 |
| WO | WO2010/096462 A1 | 8/2010 |
| WO | WO2010/096777 A1 | 8/2010 |
| WO | WO2010/099527 A1 | 9/2010 |
| WO | WO2010/111483 A1 | 9/2010 |
| WO | WO2010/111534 A1 | 9/2010 |
| WO | WO2010/111673 A1 | 9/2010 |
| WO | WO2010/117635 A1 | 10/2010 |
| WO | WO2010/117704 A1 | 10/2010 |
| WO | WO2010/117977 A1 | 10/2010 |
| WO | WO2010/120621 A1 | 10/2010 |
| WO | WO2010/120935 A1 | 10/2010 |
| WO | WO2010/122162 A1 | 10/2010 |
| WO | WO2010/132538 A1 | 11/2010 |
| WO | WO2010/132601 A1 | 11/2010 |
| WO | WO2010/138368 A1 | 12/2010 |
| WO | WO2010/138488 A1 | 12/2010 |
| WO | WO2010/138790 A1 | 12/2010 |
| WO | WO2010/138791 A1 | 12/2010 |
| WO | WO2010/144646 A2 | 12/2010 |
| WO | WO2010/148006 A1 | 12/2010 |
| WO | WO2011/004276 A1 | 1/2011 |
| WO | WO2011/009084 A2 | 1/2011 |
| WO | WO2011/015657 A1 | 2/2011 |
| WO | WO2011/015658 A1 | 2/2011 |
| WO | WO2011/026920 A1 | 3/2011 |
| WO | WO2011/028596 A1 | 3/2011 |
| WO | WO2011/031904 A1 | 3/2011 |
| WO | WO2011/031934 A1 | 3/2011 |
| WO | WO2011/050146 A1 | 4/2011 |
| WO | WO2012/046811 A1 | 4/2011 |
| WO | WO2011/054834 A1 | 5/2011 |
| WO | WO2011/059850 A1 | 5/2011 |
| WO | WO2011/059887 A1 | 5/2011 |
| WO | WO2011/060000 A1 | 5/2011 |
| WO | WO2011/066241 A1 | 6/2011 |
| WO | WO2011/068941 A2 | 6/2011 |
| WO | WO2011/075439 A1 | 6/2011 |
| WO | WO2011/075607 A1 | 6/2011 |
| WO | WO2011/075615 A1 | 6/2011 |
| WO | WO2011/079327 A1 | 6/2011 |
| WO | WO2011/081918 A1 | 7/2011 |
| WO | WO2011/082077 A1 | 7/2011 |
| WO | WO2011/087740 A1 | 7/2011 |
| WO | WO2011/091417 A1 | 7/2011 |
| WO | WO2011/091446 A1 | 7/2011 |
| WO | WO2011/091532 A1 | 8/2011 |
| WO | WO2011/109037 A1 | 9/2011 |
| WO | WO2011/112429 A1 | 9/2011 |
| WO | WO2011/119853 A1 | 9/2011 |
| WO | WO2011/119860 A1 | 9/2011 |
| WO | WO2011/119870 A1 | 9/2011 |
| WO | WO2011/127350 A1 | 10/2011 |
| WO | WO2011/146401 A1 | 11/2011 |
| WO | WO2011/149856 A1 | 12/2011 |
| WO | WO2011/150243 A1 | 12/2011 |
| WO | WO2011/153396 A1 | 12/2011 |
| WO | WO2011/154871 A1 | 12/2011 |
| WO | WO2011/156543 A2 | 12/2011 |
| WO | WO2011156578 A1 | 12/2011 |
| WO | WO2012/003642 A1 | 1/2012 |
| WO | WO2012/009394 A2 | 1/2012 |
| WO | WO2012/013643 A1 | 2/2012 |
| WO | WO2012/018325 A1 | 2/2012 |
| WO | WO2012/018534 A2 | 2/2012 |
| WO | WO2012/020036 A1 | 2/2012 |
| WO | WO2012/021591 A1 | 2/2012 |
| WO | WO2012/021704 A1 | 2/2012 |
| WO | WO2012/027712 A2 | 3/2012 |
| WO | WO2012/040389 A2 | 3/2012 |
| WO | WO2012/040923 A1 | 4/2012 |
| WO | WO2012/040924 A1 | 4/2012 |
| WO | WO2012/041014 A1 | 4/2012 |
| WO | WO2012/041227 A1 | 4/2012 |
| WO | WO2012/048421 A1 | 4/2012 |
| WO | WO2012/050848 A1 | 4/2012 |
| WO | WO2012/050850 A1 | 4/2012 |
| WO | WO2012/050918 A2 | 4/2012 |
| WO | WO2012/051361 A1 | 4/2012 |
| WO | WO2012/018829 A1 | 5/2012 |
| WO | WO2012/061552 A1 | 5/2012 |
| WO | WO2012/068234 A2 | 5/2012 |
| WO | WO2012/074437 A2 | 6/2012 |
| WO | WO2012/083043 A1 | 6/2012 |
| WO | WO2012/083048 A2 | 6/2012 |
| WO | WO2012/083053 A2 | 6/2012 |
| WO | WO2012/083058 A2 | 6/2012 |
| WO | WO2012/083059 A1 | 6/2012 |
| WO | WO2012/083061 A2 | 6/2012 |
| WO | WO2012/083170 A1 | 6/2012 |
| WO | WO2012/087596 A1 | 6/2012 |
| WO | WO2012083164 A1 | 6/2012 |
| WO | WO2012087976 A2 | 6/2012 |
| WO | WO2012/116257 A1 | 8/2012 |
| WO | WO2012109080 A1 | 8/2012 |
| WO | WO2012/123298 A1 | 9/2012 |
| WO | WO2012/125926 A2 | 9/2012 |
| WO | WO2012122716 A1 | 9/2012 |
| WO | WO2012/135581 A1 | 10/2012 |
| WO | WO2012/154777 A1 | 11/2012 |

(56) References Cited

FOREIGN PATENT DOCUMENTS

| | | |
|---|---|---|
| WO | WO2012162578 A2 | 11/2012 |
| WO | WO2012162580 A2 | 11/2012 |
| WO | WO2012/166716 A2 | 12/2012 |
| WO | WO2012/175581 A1 | 12/2012 |
| WO | WO2013/007106 A1 | 1/2013 |
| WO | WO2013/021337 A1 | 2/2013 |
| WO | WO2013/021344 A1 | 2/2013 |
| WO | WO2013/022810 A1 | 2/2013 |
| WO | WO2013/028953 A1 | 2/2013 |
| WO | WO2013/030750 A1 | 3/2013 |
| WO | WO2013/039876 A1 | 3/2013 |
| WO | WO2013/039878 A1 | 3/2013 |
| WO | WO2013/052362 A1 | 4/2013 |
| WO | WO2013/052369 A1 | 4/2013 |
| WO | WO2013/053657 A1 | 4/2013 |
| WO | WO2013/059278 A2 | 4/2013 |
| WO | WO2013/059630 A1 | 4/2013 |
| WO | WO2013/059638 A1 | 4/2013 |
| WO | WO2013/066753 A1 | 5/2013 |
| WO | WO2013/075029 A1 | 5/2013 |
| WO | WO2013/087743 A1 | 6/2013 |
| WO | WO2013/095275 A1 | 6/2013 |
| WO | WO2013/098313 A1 | 7/2013 |
| WO | WO2013/098320 A1 | 7/2013 |
| WO | WO2013/101550 A1 | 7/2013 |
| WO | WO2013/106520 A1 | 7/2013 |
| WO | WO2013101552 A1 | 7/2013 |
| WO | WO2013/118097 A1 | 8/2013 |
| WO | WO2013/118102 A1 | 8/2013 |
| WO | WO2013/123092 A1 | 8/2013 |
| WO | WO2013/173492 A1 | 11/2013 |
| WO | WO2014/036244 A1 | 3/2014 |
| WO | WO2014/065791 A1 | 5/2014 |
| WO | WO2014/074604 A2 | 5/2014 |
| WO | WO2014/100500 A1 | 6/2014 |
| WO | WO2015/017382 A1 | 2/2015 |
| WO | WO2015/026454 A1 | 2/2015 |
| WO | WO2015/042375 A1 | 3/2015 |
| WO | WO2015/088817 A1 | 6/2015 |
| WO | WO2015/110048 A1 | 7/2015 |
| WO | WO2015/134560 A1 | 9/2015 |
| WO | WO2015/134561 A1 | 9/2015 |
| WO | WO2015/160907 A2 | 10/2015 |

OTHER PUBLICATIONS

Lemm, et al, "Discovery of Potent NS5A Inhibitors with Dimeric Structures," Antimicrob. Agents and Chemother., 55, pp. 3795-3802 (2011).

Fridell, et al., "Distinct Functions of NS5A in HCV RNA Replication Uncovered by Studies with the NS5A Inhibitor BMS-790052," J Virol., 85, pp. 7312-7320 (2011).

Fridell, et al., "Genotypic and Phenotypic Analysis of Variants Resistant to HCV NS5A Replication Complex Inhibitor BMS-790052: In Vitro and In Vivo Correlations," Hepatology, 54, pp. 1924-1935 (2011).

Nettles, et al., "Multiple ascending dose study to evaluate BMS-790052 a novel NS5A inhibitor in subjects infected with hepatitis C virus genotype 1.," Hepatology, 54, pp. 1956-1966 (2011).

Qiu, et al., "The effects of NS5A inhibitors on NS5A phosphorylation polyprotein processing and localization," J. Gen. Virology, 92, pp. 2502-2511 (2011).

Sun, "Impact of a baseline polymorphism on the emergence of resistance to the HCV NS5A replication complex inhibitor BMS-790052," Hepatology, 55, pp. 1956-1965 (2011).

Wang, et al., "In Vitro Activity of BMS-790052 on Hepatitis C Virus Genotype 4 NS5A, Antimicrob. Agents and Chemother.," 56, pp. 1588-1590 (2012).

Wang, et al., "Hepatitis C virus RNA elimination and development of resistance in replicon cells treated with BMS-790052," Antimicrob. Agents and Chemother., 56, pp. 1350-1358 (2012).

Pelosi, et al. "Effect of NS5A Inhibitor Combinations on Replication In Vitro.,," Antimicrob. Agents and Chemother., 56, pp. 5230-5639 (2012).

Wang, et al., "In vitro Activity of Daclatasvir on Hepatitis C Virus Genotype 3 NS5A," Antimicrob. Agents and Chemother., 57, pp. 611-613 (2013).

\* cited by examiner

COMBINATIONS COMPRISING BIPHENYL DERIVATIVES FOR USE IN THE TREATMENT OF HCV

CROSS-REFERENCE TO RELATED APPLICATIONS

This application claims the benefit of U.S. Provisional Application Ser. No. 61/847,440, filed on Jul. 17, 2013, which is hereby incorporated by reference in its entirety.

The present disclosure is generally directed to antiviral compounds, and more specifically directed to combinations of compounds which can inhibit the function of the NS5A protein encoded by Hepatitis C virus (HCV), compositions comprising such combinations, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Over the past decade the standard of care for the treatment of chronic HCV employed a combination of pegylated-interferon and ribavirin. The treatment has a non-optimal success rate in achieving sustained viral response (SVR) against the six major HCV genotypes, with a particularly low success rate against genotype 1, and causes numerous side effects. Recently approved drugs targeting the HCV NS3/4A protease (PIs) (Victrelis® and Incivek®) are administered with pegylated-interferon and ribavirin and provide a major improvement in the percentage of patients who experience SVR and the treatment duration required to achieve SVR. However, there is a clear and urgent need to develop additional therapies to combat protease inhibitor resistance, to improve efficacy across all HCV genotypes, and to advance antiviral therapy towards the ultimate goal of an interferon-free cure.

HCV is a positive-stranded RNA virus of approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein is a cofactor for the NS3 protease. The formation of a NS3-NS4A complex is necessary for proper protease activity. The NS3 protein also exhibits nucleoside triphosphatase and RNA helicase activities. NS5A is a multi-functional protein required for viral RNA replication and virion assembly. NS5B (also referred to herein as HCV polymerase) is a RNA-dependent RNA polymerase that is responsible for viral RNA synthesis.

Considerable heterogeneity is found within the nucleotide and encoded amino acid sequence throughout the HCV genome due to the high error rate of the encoded RNA-dependent RNA polymerase which lacks a proof-reading capability. The clinical significance of the genetic heterogeneity of HCV is the propensity for mutations to arise during monotherapy treatment, thus combination therapies with HCV inhibitors that have pan-genotype coverage and act via independent mechanisms are desired.

Compounds which selectively inhibit HCV viral replication and are useful for treating HCV-infected patients are desired. In particular, compounds which effectively inhibit the function of the NS5A protein are desired. The function and the essential role of NS5A protein for HCV replication are described, for example, in the following references: S. L. Tan, et al., *Virology*, 284:1-12 (2001); K.-J. Park, et al., *J. Biol. Chem.*, 30711-30718 (2003); T. L. Tellinghuisen, et al., *Nature*, 435, 374 (2005); R. A. Love, et al., *J. Virol*, 83, 4395 (2009); N. Appel, et al., *J. Biol. Chem.*, 281, 9833 (2006); L. Huang, *J. Biol. Chem.*, 280, 36417 (2005); M. Gao, et al, *Nature* (2010); C. Rice, et al., WO2006093867.

A method has been described to identify compounds that demonstrate synergistic inhibition of HCV replicon activity when combined with the HCV NS5A inhibitor such as BMS-790052 (PCT/US2011/043785, filed Jul. 13, 2011). In brief, each compound, when tested individually versus some NS5A resistant variants, is essentially inactive or much less active and only has synergistic inhibitory activity when tested in combination with an NS5A-targeting compound. The synergistic compounds were identified using titrations of test compounds in the presence of fixed concentrations of HCV NS5A inhibitors such as BMS-790052.

In a first aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (I):

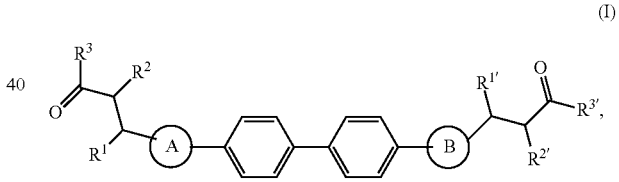

(I)

or a pharmaceutically acceptable salt thereof, wherein
A and B are independently selected from

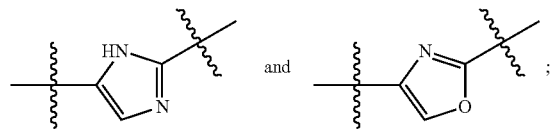 [SMILES: *c1cnc(*)[nH]1 ; *c1coc(*)n1]

$R^1$ is selected from alkoxy, alkyl, haloalkyl, and hydroxy;
$R^2$ is hydrogen; or, alternatively,
$R^1$ and $R^2$, together with the carbon atoms to which they are attached, form a dioxolanyl ring, wherein the dioxolanyl-ring is optionally substituted with one or two methyl groups;
$R^{1'}$ is selected from alkoxy, alkyl, haloalkyl, and hydroxy;
$R^{2'}$ is hydrogen; or, alternatively,
$R^{1'}$ and $R^{2'}$, together with the carbon atoms to which they are attached, form a dioxolanyl ring, wherein the dioxolanyl ring is optionally substituted with two methyl groups; and
$R^3$ and $R^{3'}$ are independently selected from alkoxy, hydroxy, and —$NR^aR^b$;

$R^a$ and $R^b$ are independently selected from hydrogen, alkoxycarbonylalkyl, alkyl, polycycloalkyl, (polycycloalkyl)alkyl, cycloalkyl, (cycloalkyl)alkyl, hydroxyalkyl, —$NR^cR^d$, ($NR^cR^d$)alkyl, ($NR^cR^d$)carbonylalkyl, phenylalkyl, and pyranyl, wherein the cycloalkyl, the cycloalkyl part of the (cycloalkyl)alkyl, and the phenyl part of the phenylalkyl is optionally substituted with one or two groups independently selected from alkoxy, alkoxyalkyl, aminocarbonyl, cyano, halo, hydroxy, and phenyl; and wherein the alkyl part of the ($NR^cR^d$)alkyl is optionally substituted with a hydroxy group; or, alternatively, $R^a$ and $R^b$, together with the nitrogen atom to which they are attached, form a ring selected from morpholine, piperidine, and piperazine wherein each ring is optionally substituted with one or two groups selected from alkoxycarbonyl, alkyl, halo, oxo, and phenyl; and one of $R^c$ and $R^d$ is selected from hydrogen and alkyl and the other is selected from hydrogen, alkoxycarbonyl, and alkyl; or, alternatively, $R^c$ and $R^d$, together with the nitrogen atom to which they are attached, form an oxazolidinone ring.

In a first embodiment of the first aspect the present disclosure provides a composition comprising said combination and one or more pharmaceutically acceptable carriers. In a second embodiment said composition comprises one or two additional compounds having anti-HCV activity. In a third embodiment at least one of the additional compounds is an interferon or a ribavirin. In a fourth embodiment the interferon is selected from interferon alpha 2B, pegylated interferon alpha, pegylated interferon lambda, consensus interferon, interferon alpha 2A, and lymphoblastoid interferon tau. In a fifth embodiment said composition comprises one or two additional compounds having anti-HCV activity wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In a second aspect the present disclosure provides a method of treating an HCV infection in a patient, comprising administering to the patient a therapeutically effective amount of said combination, or a pharmaceutically acceptable salt thereof. In a first embodiment of the second aspect the method further comprises administering one or two additional compounds having anti-HCV activity prior to, after or simultaneously with the combination, or a pharmaceutically acceptable salt thereof. In a second embodiment at least one of the additional compounds is an interferon or a ribavirin. In a third embodiment the interferon is selected from interferon alpha 2B, pegylated interferon alpha, pegylated interferon lambda, consensus interferon, interferon alpha 2A, and lymphoblastoid interferon tau. In a fourth embodiment at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

In another aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (II):

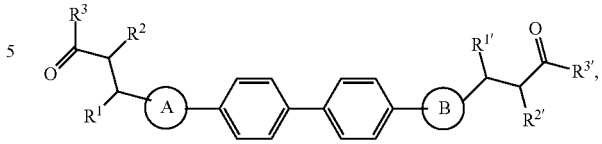

(II)

or a pharmaceutically acceptable salt thereof, wherein
A and B are independently selected from

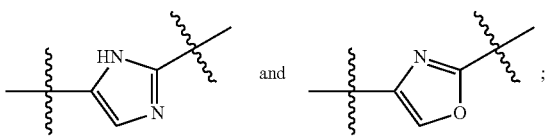 [SMILES: *c1cnc(*)[nH]1 ; *c1coc(*)n1]

$R^1$ is selected from alkoxy, alkyl, haloalkyl, and hydroxy;
$R^2$ is hydrogen; or, alternatively,
$R^1$ and $R^2$, together with the carbon atoms to which they are attached, form a dioxolanyl ring, wherein the dioxolanyl-ring is optionally substituted with two methyl groups;
$R^{1'}$ is selected from alkoxy, alkyl, haloalkyl, and hydroxy;
$R^{2'}$ is hydrogen; or, alternatively,
$R^{1'}$ and $R^{2'}$, together with the carbon atoms to which they are attached, form a dioxolanyl ring, wherein the dioxolanyl ring is optionally substituted with two methyl groups; and
$R^3$ and $R^{3'}$ are independently selected from alkoxy and —$NR^aR^b$;
$R^a$ and $R^b$ are independently selected from hydrogen, alkoxycarbonylalkyl, alkyl, —$NR^cR^d$; or, alternatively,
$R^a$ and $R^b$, together with the nitrogen atom to which they are attached, form a piperidine ring wherein the ring is optionally substituted with one or two halo groups; and
one of $R^c$ and $R^d$ is hydrogen and the other is alkoxycarbonyl.

In another aspect the present disclosure provides a combination comprising an NS5A-targeting compound and an NS5A synergist, which, when administered, provides synergistic anti-HCV activity against variants that contain mutation(s) conferring resistance to the NS5A-targeting compound alone, wherein the NS5A synergist is a compound of formula (III):

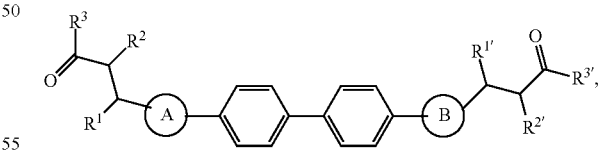

(III)

or a pharmaceutically acceptable salt thereof, wherein
A and B are independently selected from

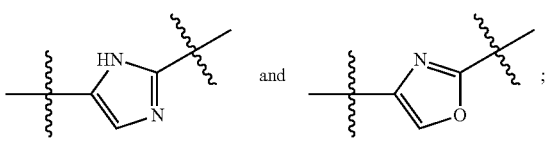

$R^1$ is selected from alkoxy, alkyl, haloalkyl, and hydroxy;

$R^2$ is hydrogen; or, alternatively, $R^1$ and $R^2$, together with the carbon atoms to which they are attached, form a dioxolanyl ring, wherein the dioxolanyl-ring is optionally substituted with one or two methyl groups;

$R^{1'}$ is selected from alkoxy, alkyl, haloalkyl, and hydroxy;

$R^{2'}$ is hydrogen; or, alternatively, $R^{1'}$ and $R^{2'}$, together with the carbon atoms to which they are attached, form a dioxolanyl ring, wherein the dioxolanyl ring is optionally substituted with two methyl groups; and $R^3$ and $R^{3'}$ are independently selected from alkoxy and —$NR^aR^b$;

$R^a$ and $R^b$ are independently selected from hydrogen, alkoxycarbonylalkyl, alkyl, cycloalkyl, (cycloalkyl)alkyl, hydroxyalkyl, —$NR^cR^d$, —$(NR^cR^d)$carbonylalkyl, phenylalkyl, and pyranyl, wherein the cycloalkyl and the cycloalkyl part of the (cycloalkyl)alkyl is optionally substituted with one or two groups independently selected from cyano, halo, and hydroxy; or, alternatively, $R^a$ and $R^b$, together with the nitrogen atom to which they are attached, form a ring selected from morpholine, piperidine, and piperazine wherein each ring is optionally substituted with one or two groups selected from alkoxycarbonyl, alkyl, halo, oxo, and phenyl; and one of $R^c$ and $R^d$ is selected from hydrogen and alkyl and the other is selected from hydrogen, alkoxycarbonyl and alkyl.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order to accommodate a substituent at any given location.

In some instances, the number of carbon atoms in any particular group is denoted before the recitation of the group. For example, the term "$C_{2-6}$ alkenyl" denotes an alkenyl group containing two to six carbon atoms. Where these designations exist they supersede all other definitions contained herein.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term "aryl".

As used herein, the term "NS5A synergist" refers to a molecule that alone shows a weaker activity against HCV wild type than the NS5A-targeting compound, but when combined with an NS5A-targeting compound shows a greater than three-fold increase in $EC_{50}$ potency than the potency of the NS5A-targeting compound alone.

As used herein, the term "synergistic anti-HCV activity" refers to a greater than three-fold increase in $EC_{50}$ potency than the potency of the NS5A-targeting compound alone.

As used herein, the term "NS5A-targeting compound", refers to a molecule that inhibits HCV replication for which at least one resistance substitution maps to the NS5A protein and most commonly within, but not limited to, the first 100 residues of NS5A.

The term "alkoxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "alkoxycarbonylalkyl," as used herein, refers to an alkyl group substituted with one or two alkoxycarbonyl groups.

The term "alkyl," as used herein, refers to a group derived from a straight or branched chain saturated hydrocarbon containing from one to seven carbon atoms.

The term "aminocarbonyl," as used herein, refers to —$C(O)NH_2$.

The term "cyano," as used herein, refers to —CN.

The term "cycloalkyl," as used herein, refers to a three- to seven-membered monocyclic carbocycle.

The term "(cycloalkyl)alkyl," as used herein, refers to an alkyl group substituted with one, two, or three cycloalkyl groups.

The term "halo," as used herein, refers to Cl, Br, F, or I.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

The term "$(NR^cR^d)$alkyl," as used herein, refers to an alkyl group substituted with one, two, or three —$NR^cR^d$ groups.

The term "$(NR^cR^d)$carbonyl," as used herein, refers to an —$NR^cR^d$ group attached to the parent molecular moiety through a carbonyl group.

The term "$(NR^cR^d)$carbonylalkyl," as used herein, refers to an alkyl group substituted with one, two, or three $(NR^cR^d)$ carbonyl groups.

The term "oxo," as used herein, refers to =O.

The term "phenylalkyl," as used herein, refers to an alkyl group substituted with one, two, or three phenyl groups.

The term "polycycloalkyl," as used herein, refers to a polycyclic saturated fused, bridged, or spirocyclic hydrocarbon ring system having five to twelve carbon atoms and zero heteroatoms.

The term "(polycycloalkyl)alkyl," as used herein, refers to an alkyl group substituted with one, two, or three polycycloalkyl groups.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure also exist as tautomers; therefore the present disclosure also encompasses all tautomeric forms.

The term "compounds of the present disclosure", and equivalent expressions, are meant to embrace the compounds making up the combination of the present disclosure and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthalenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of each compound of the combination, as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of the compounds comprising the combination or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of the combination and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing the compounds of the combination, or pharmaceutically acceptable salts thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of Formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of the combination and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table A below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE A

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phameuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |

TABLE A-continued

| Brand Name | Physiological Class | Type of Inhibitor or Target | Source Company |
|---|---|---|---|
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |

TABLE A-continued

| Brand Name | Physiological Class | Type of Inhibitor or Target | Source Company |
|---|---|---|---|
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |

TABLE A-continued

| Brand Name | Physiological Class | Type of Inhibitor or Target | Source Company |
|---|---|---|---|
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Gilead |
| sofosbuvir | Antiviral | Nucleotide NS5B Polymerase Inhibitor | Gilead |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |
| daclatasvir | Antiviral | NS5A inhibitor | Bristol-Myers Squibb |
| BMS-791325 | Antiviral | NS5B Polymerase Inhibitor | Bristol-Myers Squibb |
| ACH-3102 | Antiviral | NS5A inhibitor | Achillion |
| asunaprevir | Antiviral | serine protease inhibitor | Bristol-Myers Squibb |
| IDX-719 | Antiviral | NS5A inhibitor | Idenix |
| Ledipasvir | Antiviral | NS5A inhibitor | Gilead |
| GS-5816 | Antiviral | NS5A inhibitor | Gilead |
| Ombitasvir | Antiviral | NS5A inhibitor | Abbvie |
| GSK-2336805 | Antiviral | NS5A inhibitor | GlaxoSmithKline |
| PPI-461 | Antiviral | NS5A inhibitor | Presidio |
| EDP-239 | Antiviral | NS5A inhibitor | Enanta |
| Elbasvir | Antiviral | NS5A inhibitor | Merck |
| IDX-21437 | Antiviral | Nucleotide Polymerase Inhibitor | Idenix |
| Samatasvir | Antiviral | NS5A Inhibitor | Idenix |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: RT or rt for room temperature or retention time (context will dictate); $R_t$ for retention time; TFA for trifluoroacetic acid; min or mins for minutes; ACN or MeCN for acetonitrile; DIEA for diisopropylethylamine; h or hr or hrs for hours; EtOAc for ethyl acetate; HOAT for 1-hydroxy-7-azabenzotriazole; EDC for 1-ethyl-3-(3-dimethylaminopropyl)carbodiimide hydrochloride; DMAP for 4-(dimethylamino)pyridine; DMF for N,N-dimethylformamide; HATU for O-(7-azabenzotriazole-1-yl)-1,1,3,3-tetramethyluronium hexafluorophosphate; THF for tetrahydrofuran (Note: all THF was freshly distilled over sodium/benzophenone ketyl); MeOH for methanol; DCM for dichloromethane; and NMP for 1-methyl-2-pyrrolidinone.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what was believed to be the most useful and readily understood description of its procedures and conceptual aspects.

Starting materials can be obtained from commercial sources or prepared by well-established literature methods known to those of ordinary skill in the art.

LC/MS Condition MD-1:
Column=Phenomenex-Luna, 2.0×50 mm, 3 μm
Solvent A=0.1% TFA in 10% methanol/90% water
Solvent B=0.1% TFA in 90% methanol/10% water
Start % B=0; Final % B=100
Gradient time=4 min
Flow Rate=0.8 mL/min
Wavelength=220 nm or 254 nm
Oven temp.=40° C.
LC/MS Condition MD-2:
Column=Phenomenex-Luna C18, 2.0×50 mm, 3 μm
Solvent A=10 mM ammonium acetate in 5% acetonitrile/95% water
Solvent B=10 mM ammonium acetate in 90% acetonitrile/5% water
Start % B=0; Final % B=100
Gradient time=4 min
Flow Rate=0.8 mL/min
Wavelength=220 nm or 254 nm
Oven temp.=40° C.
LC/MS Condition B-12:
Column=Ascentis Express C18, 2.1×50 mm, 2.7 μm
Solvent A=$CH_3CN$ (2%)+10 mM ammonium formate in $H_2O$ (98%)
Solvent B=$CH_3CN$ (98%)+10 mM ammonium formate in $H_2O$ (2%)
Start % B=0; Final % B=100
Gradient time=1.4 min
Flow Rate=1 mL/min; Wavelength=220 nm
LC/MS Condition B-32:
Column=Sunfire C18, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min
Flow Rate=1 mL/min
Wavelength=220 & 254 nm
LC/MS Condition B-35:
Column=Xbridge phenyl, 4.6×150 mm, 3.5 um
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min
Flow Rate=1 mL/min
Wavelength=220 & 254 nm
Reverse Phase Preparative HPLC Condition MD-1:
Unless noted otherwise, all reverse phase prep HPLC conditions for the purification of Example MD-1 to MD-61 are as follows:
Column=Phenomenex Luna Axia C-18, 30×100 mm, 10 μm
Solvent A=0.1% TFA in 10% methanol/90% water
Solvent B=0.1% TFA in 90% methanol/10% water
Gradient: linear gradient, specific for each example
Gradient time: specific for each example
Flow rate=40 mL/min
Wavelength=254 nm
Analytical HPLC Conditions:
MD-A:
Column=Xbridge C18, 3.0×150 mm, 3.5 μm
Solvent A=10 mM $NH_4HCO_3$ in 5% methanol/95% water
Solvent B=10 mM $NH_4HCO_3$ in 95% methanol/5% water
Start % B=0; Final % B=100
Gradient time=30 min
Flow Rate=1.0 mL/min
Wavelength=220 nm or 254 nm
MD-B:
Column=Xbridge phenyl, 3.0×150 mm, 3.5 μm
Start % B=0; Final % B=100
Gradient time=30 min
Flow Rate=1.0 mL/min; Wavelength=220 nm or 254 nm
Solvent A=10 mM $NH_4HCO_3$ in 5% methanol/95% water
Solvent B=10 mM $NH_4HCO_3$ in 95% methanol/5% water
MD-C:
Column=Sunfire C18, 3.0×150 mm, 3.5 μm
Start % B=0; Final % B=100
Gradient time=30 min
Flow Rate=1.0 mL/min; Wavelength=220 nm or 254 nm
Solvent A=0.05% TFA in 5% ACN/95% water
Solvent B=0.05% TFA in 95% ACN/5% water
MD-D:
Column=Xbridge phenyl, 3.0×150 mm, 3.5 μm
Start % B=0; Final % B=100
Gradient time=30 min
Flow Rate=1.0 mL/min; Wavelength=220 nm or 254 nm
Solvent A=0.05% TFA in 5% ACN/95% water
Solvent B=0.05% TFA in 95% ACN/5% water

EXAMPLE MD-1

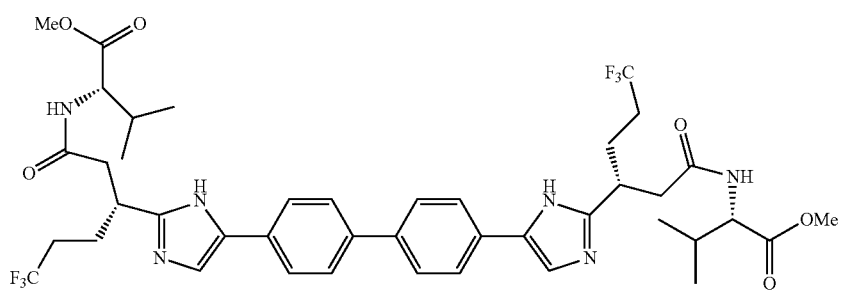 [SMILES: COC(=O)[C@@H](NC(=O)C[C@@H](CCC(F)(F)F)c1ncc(-c2ccc(-c3ccc(-c4cnc([C@H](CCC(F)(F)F)CC(=O)N[C@H](C(=O)OC)C(C)C)[nH]4)cc3)cc2)[nH]1)C(C)C]

EXAMPLE MD-1

Step a

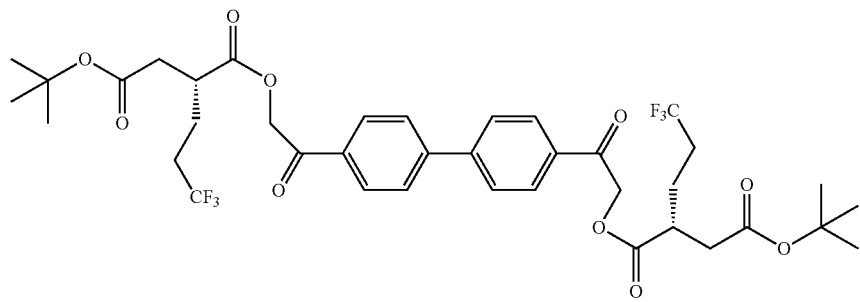 [SMILES: CC(C)(C)OC(=O)C[C@@H](CCC(F)(F)F)C(=O)OCC(=O)c1ccc(-c2ccc(C(=O)COC(=O)[C@H](CCC(F)(F)F)CC(=O)OC(C)(C)C)cc2)cc1]

To a suspension of 1,1'-([1,1'-biphenyl]-4,4'-diyl)bis(2-bromoethanone) (500 mg, 1.262 mmol) and (R)-2-(2-(tert-butoxy)-2-oxoethyl)-5,5,5-trifluoropentanoic acid (700 mg, 2.052 mmol) (prepared according to the procedure described in WO2012129353-A1) in anhydrous ACN (15 mL) at 0° C. was slowly added DIEA (485 µL, 2.78 mmol). The reaction was flushed well with $N_2$, securely capped and allowed to stir for 18 h while slowly warming to room temp. The solvent was removed in vacuo and the crude product was purified by flash column chromatography (80 g Teledyne Isco Silica Flash Column, 100% hexanes to 60% ethyl acetate/hexanes over 10 column volumes) to afford the title compound (880 mg) as a white solid. $^1$H NMR (500 MHZ, $CDCl_3$) δ 8.04 (d, J=8.4 Hz, 4H), 7.76 (d, J=8.4 Hz, 4H), 5.53 (d, J=16.4 Hz, 2H), 5.34 (d, J=16.3 Hz, 2H), 3.16-2.99 (m, 2H), 2.83 (dd, J=16.4, 8.2 Hz, 2H), 2.58-2.22 (m, 6H), 2.14-1.86 (m, 4H), 1.48 (s, 18H).

EXAMPLE MD-1

Step b

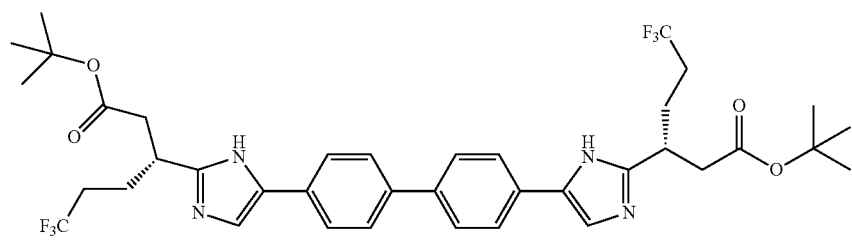 [SMILES: CC(C)(C)OC(=O)C[C@@H](CCC(F)(F)F)c1ncc(-c2ccc(-c3ccc(-c4cnc([C@H](CCC(F)(F)F)CC(=O)OC(C)(C)C)[nH]4)cc3)cc2)[nH]1]

To a 48 ml, pressure bottle under $N_2$ was added material from Example MD-1, step a (880 mg, 1.136 mmol), ammonium acetate (2.65 g, 34.4 mmol), imidazole (462 mg, 6.79 mmol) and anhydrous toluene (18 mL). The reaction was flushed with $N_2$, capped and heated at 110° C. for 18 h. The reaction was diluted with EtOAc (300 mL) and the organic layer was washed with saturated aqueous $NaHCO_3$ (70 mL), water (2×50 mL), brine (1×50 mL), dried over $Na_2SO_4$, filtered and concentrated to dryness in vacuo. The crude product was purified by flash column chromatography (80 g Teledyne Isco Silica Flash Column, 100% dichloromethane to 100% ethyl acetate over 12 column volumes) to afford the title compound (510 mg) as a white solid. LC/MS Condition MD-1: $[M+H]^+$ 735, $R_t$=3.401 min; $^1$H NMR (500 MHZ, $CDCl_3$) δ 7.73 (br. s., 2H), 7.60 (br. s., 4H), 7.32-7.15 (m, 4H), 3.33-3.23 (m, 2H), 2.78-2.50 (m, 4H), 2.18-1.75 (m, 8H), 1.43-1.24 (m, 18H).

EXAMPLE MD-1

Step c

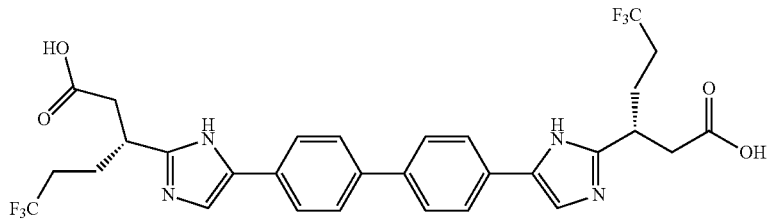 [SMILES: O=C(O)C[C@@H](CCC(F)(F)F)c1ncc(-c2ccc(-c3ccc(-c4cnc([C@H](CCC(F)(F)F)CC(=O)O)[nH]4)cc3)cc2)[nH]1]

To a suspension of material from Example MD-1, step b (508 mg, 0.691 mmol) in anhydrous dichloromethane (8 mL) with vigorous swirling was added TFA (10.0 mL, 130 mmol). The reaction was allowed to stand at room temp for 125 min, then the volatiles were removed under a gentle stream of $N_2$. The residue was suspended in toluene (30 mL) and the solvent was removed in vacuo to give the title compound (785 mg) as a tris TFA salt as a tan solid. LC/MS Condition MD-1: $[M+H]^+$ 623, $R_t$=3.02 min; $^1H$ NMR (500 MHZ, DMSO-$d_6$) δ 14.6 (m, 3H), 12.5 (m, 1H), 8.19 (s, 2H), 8.00-7.96 (m, 4H), 7.96-7.87 (m, 4H), 3.62-3.52 (m, 2H), 3.05-2.90 (m, 4H), 2.42-2.20 (m, 4H), 2.09-1.96 (m, 4H); $^{19}F$ NMR (470 MHZ, DMSO-$d_6$) δ −64.84 (s, 6F), −74.51 (s, 9F).

EXAMPLE MD-1

To a mixture of material from Example MD-1, step c (44.3 mg, 0.046 mmol), (S)-methyl 2-amino-3-methylbutanoate, HCl (67.8 mg, 0.4.4 mmol), and HOAT (18.7 mg, 0.137 mmol) in anhydrous dichloromethane (3 mL) under $N_2$ was added EDC (62.4 mg, 0.326 mmol) and DIEA (130 μL, 0.744 mmol). The reaction was flushed with $N_2$, securely capped and stirred at room temp for 18 h. DMAP (23.4 mg, 0.192 mmol) was added and the reaction was allowed to stir at room temp for 4 days. The solvent was evaporated under a gentle stream of $N_2$, and the crude product was purified by reverse phase preparative HPLC conditions MD-1 using a gradient from 20% solvent B/80% solvent A to 100% solvent B over 11 min to give the title compound (16.8 mg) as a bis TFA salt as a white solid. LC/MS Condition MD-1: $[M+H]^+$ 849, $R_t$=3.31 min; $^1H$ NMR (500 MHZ, $CD_3OD$) δ 7.90 (s, 2H), 7.90-7.85 (m, 8H), 4.29 (d, J=6.0 Hz, 2H), 3.72 (s, 6H), 3.71-3.66 (m, 2H), 3.03-2.97 (m, 2H), 2.97-2.90 (m, 2H), 2.42-2.31 (m, 2H), 2.24-2.09 (m, 8H), 0.91 (d, J=6.9 Hz, 6H), 0.89 (d, J=6.9 Hz, 6H).
Analytical HPLC MD-A: $R_t$=27.37 min, λ=220 nm
Analytical HPLC MD-B: $R_t$=27.12 min, λ=220 nm
Analytical HPLC MD-C: $R_t$=5.65 min, λ=254 nm
Analytical HPLC MD-D: $R_t$=6.29 min, λ=254 nm

EXAMPLE MD-2

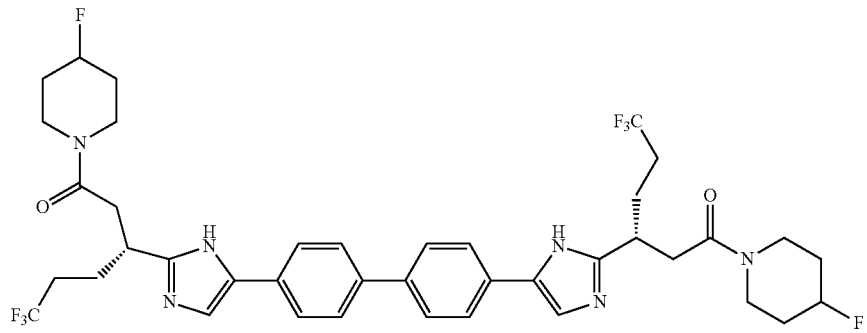 [SMILES: O=C(C[C@@H](CCC(F)(F)F)c1ncc(-c2ccc(-c3ccc(-c4cnc([C@H](CCC(F)(F)F)CC(=O)N5CCC(F)CC5)[nH]4)cc3)cc2)[nH]1)N1CCC(F)CC1]

To a mixture of material from Example MD-1, step c (47 mg, 0.049 mmol), 4-fluoropiperidine, HCl (76 mg, 0.544 mmol) and HOAT (19.6 mg, 0.144 mmol) in anhydrous dichloromethane (4 mL) under $N_2$ was added EDC (83 mg, 0.433 mmol) and DIEA (160 μL, 0.916 mmol). The reaction was flushed with $N_2$, securely capped and stirred at room temp for 18 h. Imidazole (150 mg, 2.203 mmol) and additional EDC (190 mg, 0.991 mmol) was added and the reaction was allowed to stir at room temp for 18 h. The solvent was evaporated under a gentle stream of $N_2$, and the crude product was purified by reverse phase preparative HPLC conditions MD-1 using a gradient from 30% solvent B/70% solvent A to 100% solvent B over 11 min to give the impure title compound as a tris TFA salt as a white solid. LC/MS Condition MD-1: $[M+H]^+$ 793, $R_t$=3.2 min. The impure title compound was further purified via preparative LC/MS with the following conditions: Column: XBridge C18, 19×mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 25 min, then a 5-min hold at 100% B; Flow: 20 mL/min. to give the pure title compound (11.4 mg). $^1H$ NMR (500 MHZ, DMSO-$d_6$) δ 7.81 (br. s., 4H), 7.69 (br. s., 4H), 7.55 (br. s., 2H), 4.95-4.78 (m, 2H), 3.67-3.42 (m, 10H), 2.96 (dd, J=16.0, 7.3 Hz, 2H), 2.69 (d, J=16.0 Hz, 2H), 2.32-2.23 (m, 2H), 2.22-2.12 (m, 2H), 1.97-1.80 (m, 7H), 1.76-1.52 (m, 5H).

EXAMPLE MD-3

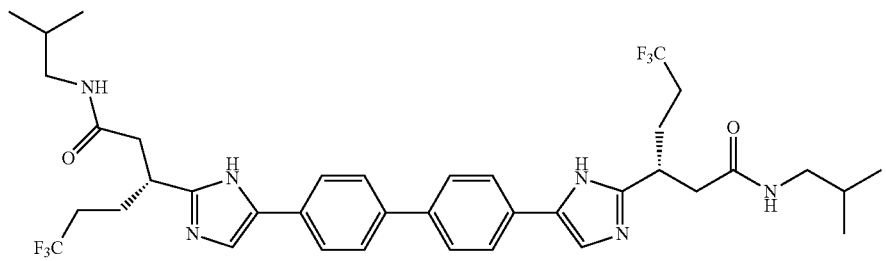 [SMILES: CC(C)CNC(=O)C[C@@H](CCC(F)(F)F)c1ncc(-c2ccc(-c3ccc(-c4cnc([C@H](CCC(F)(F)F)CC(=O)NCC(C)C)[nH]4)cc3)cc2)[nH]1]

To a mixture of material from Example MD-1, step c (70 mg, 0.073 mmol), 2-methylpropan-1-amine (65.7 mg, 0.898 mmol) and HOAT (14 mg, 0.103 mmol) in anhydrous DMF (4 mL) was added EDC (90 mg, 0.469 mmol). The reaction was flushed with $N_2$, securely capped and stirred at 55° C. for 18 h. The volatiles were evaporated off under a gentle stream of $N_2$ and the crude product was purified by reverse phase preparative HPLC conditions MD-1 using a gradient from 25% solvent B/75% solvent A to 100% solvent B over 10 min to give the TFA salt of the title compound (9.0 mg) as a white solid. LC/MS Condition MD-1: [M+H]$^+$ 733, $R_f$=3.38 min; $^1$H NMR (500 MHZ, $CD_3OD$) δ 7.90 (s, 2H), 7.90-7.85 (m, 8H), 3.76-3.59 (m, 2H), 3.06-3.00 (m, 2H), 2.98-2.92 (m, 2H), 2.91-2.81 (m, 4H), 2.40-2.30 (m., 2H), 2.26-2.10 (m, 6H), 1.73 (m, J=6.7 Hz, 2H), 0.88 (d, J=6.7 Hz, 6H), 0.87 (d, J=6.7 Hz, 6H); $^{19}$F NMR (470 MHZ, $CD_3OD$) δ −67.89 (s, 6F), −77.10 (s, 6F).

EXAMPLE MD-4

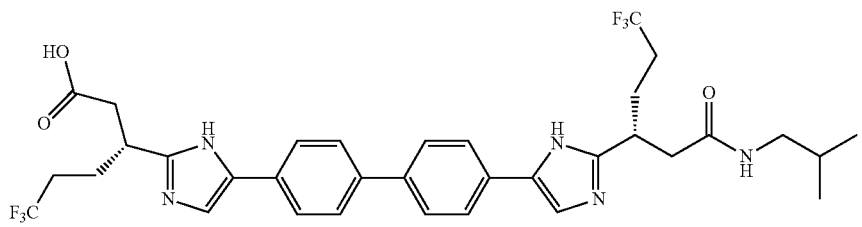 [SMILES: CC(C)CNC(=O)C[C@@H](CCC(F)(F)F)c1ncc(-c2ccc(-c3ccc(-c4cnc([C@H](CCC(F)(F)F)CC(=O)O)[nH]4)cc3)cc2)[nH]1]

Also isolated from the reaction described in Example MD-3 was the TFA salt of the title compound (16.9 mg) shown above as a white solid. LC/MS Condition MD-1: [M+H]$^+$ 678, $R_f$=3.17 min; $^1$H NMR (500 MHZ, $CD_3OD$) δ 7.91 (s, 1H), 7.90 (s, 1H), 7.89-7.86 (m, 8H), 3.74-3.63 (m, 2H), 3.06-2.99 (m, 3H), 2.98-2.86 (m, 3H), 2.39-2.30 (m, 2H), 2.23-2.12 (m, 6H), 1.72 (dquart, J=6.7 Hz, 1H), 0.87 (d, J=6.7 Hz, 3H), 0.86 (dd, J=6.7 Hz, 3H); $^{19}$F NMR (470 MHZ, $CD_3OD$) δ −67.33 (s, 3F), −68.74 (s, 3F), −77.07 (s, 6F).

EXAMPLE MD-5

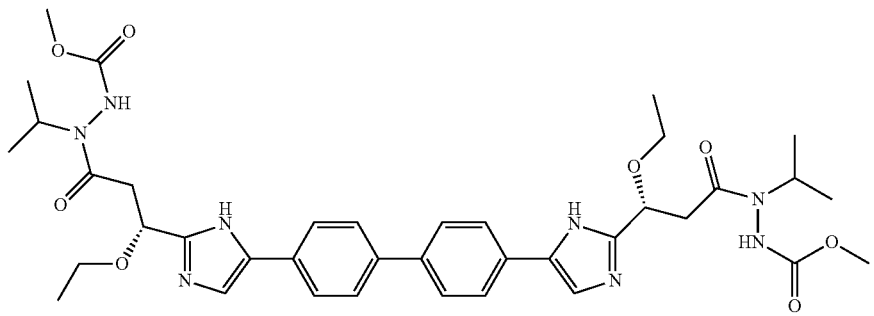 [SMILES: CCO[C@H](CC(=O)N(NC(=O)OC)C(C)C)c1ncc(-c2ccc(-c3ccc(-c4cnc([C@@H](CC(=O)N(NC(=O)OC)C(C)C)OCC)[nH]4)cc3)cc2)[nH]1]

EXAMPLE MD-5

Step a

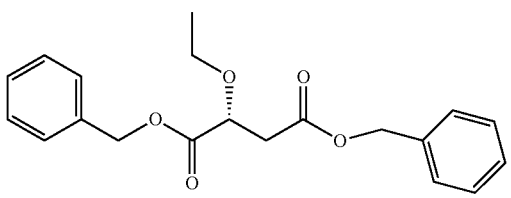 [SMILES: CCO[C@H](CC(=O)OCc1ccccc1)C(=O)OCc1ccccc1]

To a rapidly stirred solution of (R)-dibenzyl 2-hydroxysuccinate (prepared according to the procedure described in *J. Chem. Soc., Perkin Trans. 1: Organic and Bio-Organic Chemistry* (1972-1999), 1995, #22, p. 2877-2882) (1.0 g, 3.18 mmol) in iodoethane (60 mL) was added silver(I) oxide (3.90 g, 16.83 mmol). The reaction was flushed with nitrogen and heated to 80° C. for 48 h. The solid was filtered off, the solvent was removed in vacuo and the crude product was purified by flash column chromatography (80 g Teledyne Isco Silica Flash Column, 100% hexanes to 35% ethyl acetate/65% hexanes over 10 column volumes) to afford the title compound (682 mg) as colorless oil. LC/MS Condition MD-2: [M+H]$^+$ 343, R$_t$=3.36 min; $^1$H NMR (500 MHZ, CDCl$_3$) δ 7.42-7.30 (m, 10H), 5.21-5.10 (m, 4H), 4.37 (dd, J=8.2, 4.9 Hz, 1H), 3.74 (dq, J=9.0, 7.0 Hz, 1H), 3.50 (dq, J=9.1, 7.0 Hz, 1H), 2.91-2.78 (m, 2H), 1.19 (t, J=7.0 Hz, 3H).

EXAMPLE MD-5

Step b

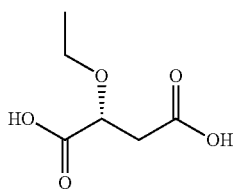

To a rapidly stirred solution of material from MD-5, step a (682 mg, 1.992 mmol) in methanol (40 mL) was added 30% Pd/C (385 mg). The resulting black suspension was flushed with nitrogen, securely capped, purged very well with H$_2$ and stirred overnight at room temperature under H$_2$. The reaction was flushed with N$_2$, the catalyst was filtered off thru a small pad of Celite and the solvent was removed in vacuo to give the title compound (323 mg) as a white solid. $^1$H NMR (500 MHZ, CDCl$_3$) δ 4.31 (dd, J=7.0, 4.7 Hz, 1H), 3.86-3.74 (m, 1H), 3.72-3.59 (m, 1H), 3.02-2.84 (m, 2H), 1.27 (t, J=6.9 Hz, 3H).

EXAMPLE MD-5

Step c

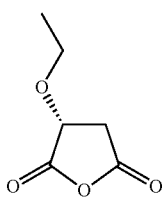

To a rapidly stirred solution of material from MD-5, step b (273 mg, 1.684 mmol) in anhydrous dichloromethane (15 mL) was added trifluoroacetic anhydride (20 mL, 142 mmol). The resulting pale yellow solution was stirred at room temp for 20 min, and then the solvent was removed in vacuo. The residue was redissolved in anhydrous dichloromethane (7 mL) and evaporated to dryness to give the title compound (243 mg) as a TFA salt. $^1$H NMR (400 MHZ, CDCl$_3$) δ 4.51 (dd, J=8.5, 5.5 Hz, 1H), 4.04 (dq, J=9.3, 7.0 Hz, 1H), 3.70 (dq, J=9.0, 7.0 Hz, 1H), 3.26 (dd, J=18.7, 8.7 Hz, 1H), 2.96 (dd, J=18.7, 5.6 Hz, 1H), 1.27 (t, J=7.0 Hz, 3H).

EXAMPLE MD-5

Step d

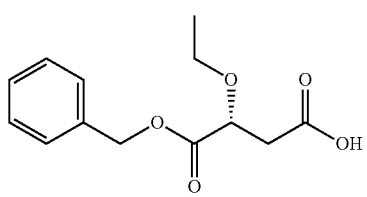 [SMILES: CCO[C@H](CC(=O)O)C(=O)OCc1ccccc1]

To a rapidly stirred solution of material from MD-5, step c (243 mg, 1.684 mmol) in THF (1.5 mL) was added benzyl alcohol (185 µL, 1.78 mmol). The reaction was flushed well with N$_2$, securely capped and placed in a 60° C. sand-bath for 24 h. The solvent was removed in vacuo, the residue was redissolved in dichloromethane (10 mL) and the solvent was again removed in vacuo to give the title compound (425 mg). $^1$H NMR (500 MHZ, CDCl$_3$) δ 7.48-7.31 (m, 5H), 5.29-5.17 (m, 2H), 4.34 (dd, J=8.2, 4.7 Hz, 1H), 3.84-3.74 (m, 1H), 3.56 (dq, J=9.1, 7.0 Hz, 1H), 2.92-2.77 (m, 2H), 1.23 (t, J=6.9 Hz, 3H).

EXAMPLE MD-5

Step e

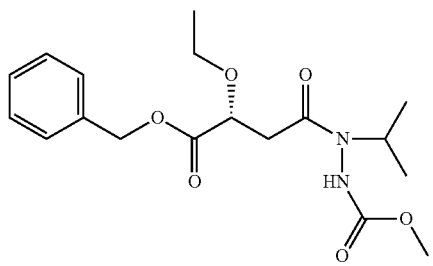 [SMILES: CCO[C@H](CC(=O)N(NC(=O)OC)C(C)C)C(=O)OCc1ccccc1]

To a solution of material from MD-5, step d (212 mg, 0.842 mmol), methyl 2-isopropylhydrazinecarboxylate (117 mg, 0.885 mmol), and 1-hydroxy-7-azabenzotriazole (10 mg, 0.073 mmol) in anhydrous dichloromethane (1.5 mL) was added EDC (200 mg, 1.043 mmol), followed immediately by DIEA (190 µL, 1.088 mmol). The reaction was flushed briefly with N$_2$, capped and stirred at room temp for 18 h. The reaction was diluted with dichloromethane (200 mL) and the organic layer was washed with saturated aqueous NaHCO$_3$ (50 mL), water (50 mL), brine (50 mL), dried over Na$_2$SO$_4$, filtered and evaporated to dryness in vacuo. The crude product was purified by flash column chromatography (40 g Teledyne Isco Silica Flash Column, 100% dichloromethane to 75% ethyl acetate/dichloromethane over 12 column volumes) to afford the title compound (161 mg) as a colorless film. LC/MS Condition MD-1:

[M+H]⁺ 367; [M+Na]⁺ 389, R$_f$=3.32 min; LC/MS Condition MD-2: [M+H]⁺ 367; [M–H]⁻ 365, R$_f$=2.62 min; ¹H NMR (500 MHZ, CDCl₃) δ 7.48-7.31 (m, 5H), 5.21 (s, 2H), 4.80 (ddd, J=19.6, 13.2, 6.6 Hz, 1H), 4.57-4.32 (m, 1H), 3.64-3.40 (m, 1H), 3.09-2.83 (m, 1H), 2.74-2.50 (m, 1H), 1.28-0.95 (m, 10H).

EXAMPLE MD-5

Step f

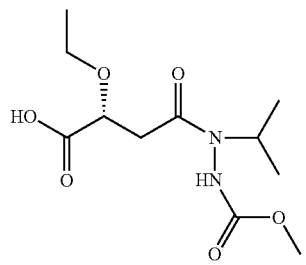 [SMILES: CCO[C@H](CC(=O)N(NC(=O)OC)C(C)C)C(=O)O]

To a solution of material from MD-5, step e (161 mg, 0.439 mmol) in a mixture of dioxane (2.15 mL) and water (1.3 mL) was added sodium hydroxide (21.0 mg, 0.91 mmol) over 40 min. After the addition was complete, the resulting solution was stirred at room temp for 95 min, cooled briefly, and quenched with 1.0 M aq. HCl (1 mL, 1.0 mmol). The reaction was diluted with dichloromethane (60 mL) and the water layer was back-extracted with dichloromethane (3×25 mL). The organic layers were combined, dried over Na₂SO₄ and MgSO₄, filtered and evaporated to dryness in vacuo to give the title compound (190 mg) as a colorless oil. LC/MS Condition MD-1: [M+H]⁺ 277; [M+Na]⁺299, R$_f$=2.39 min.

EXAMPLE MD-5

Step g

To a solution of material from MD-5, step f (121 mg, 0.438 mmol), 1,1'-([1,1'-biphenyl]-4,4'-diyl)bis(2-bromoethanone) (77 mg, 0.194 mmol) in anhydrous ACN (5 mL) at 0° C. was slowly added DIEA (120 µL, 0.687 mmol). The reaction was flushed well with N₂, securely capped and allowed to stir for 18 h while slowly warming to room temp. The solvent was removed in vacuo and the crude product was purified by flash column chromatography (24 g Teledyne Isco Silica Flash Column, 100% dichloromethane to 100% EtOAc over 12 column volumes) to afford the title compound (133.2 mg) as a colorless oil. LC/MS Condition MD-1: [M+H]⁺ 787, R$_f$=3.91 min; ¹H NMR (500 MHZ, CDCl₃) δ 8.04 (t, J=8.9 Hz, 4H), 7.77 (d, J=6.3 Hz, 4H), 5.72-5.33 (m, 4H), 4.95-4.74 (m, 2H), 4.69-4.52 (m, 2H), 3.97-3.74 (m, 8H), 3.71-3.48 (m, 2H), 3.26 (dd, J=14.5, 9.5 Hz, 1H), 3.04 (d, J=9.6 Hz, 1H), 2.87-2.64 (m, 2H), 1.34-0.98 (m, 18H).

EXAMPLE MD-5

To a solution of material from MD-5, step g (67.3 mg, 0.086 mmol) in anhydrous toluene (3.1 mL) was added ammonium acetate (268.7 mg, 3.49 mmol) and imidazole (37.8 mg, 0.555 mmol). The reaction was flushed with N₂, securely capped and placed in 90° C. oil bath for 2 h 45 min. After heating, the reaction was stirred at room temp for 18 h, heated to 100° C. for 75 min., and then DIEA (150 µL, 0.859 mmol) was added and heating continued at 100° C. for an additional 3 h 45 min. The solvent was evaporated off under a gentle stream of N₂ and the residue was purified by reverse phase preparative HPLC conditions MD-1 using a gradient from 20% solvent B/80% solvent A to 100% solvent B over 12 min to give the impure title compound (9.2 mg) as a TFA salt. LC/MS Condition MD-1: [M+H]⁺ 747, R$_f$=3.06 min.

The impure title compound was further purified via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min. to give the pure title compound (2.6 mg). ¹H NMR (500 MHZ, DMSO-d₆) δ 12.45-12.12 (m, 2H), 9.71 (br. s., 2H), 7.97-7.43 (m, 10H), 4.86 (d, J=6.7 Hz, 2H), 4.68-4.42 (m, 2H), 3.75-3.64 (m, 14H), 1.09-0.89 (m, 18H).

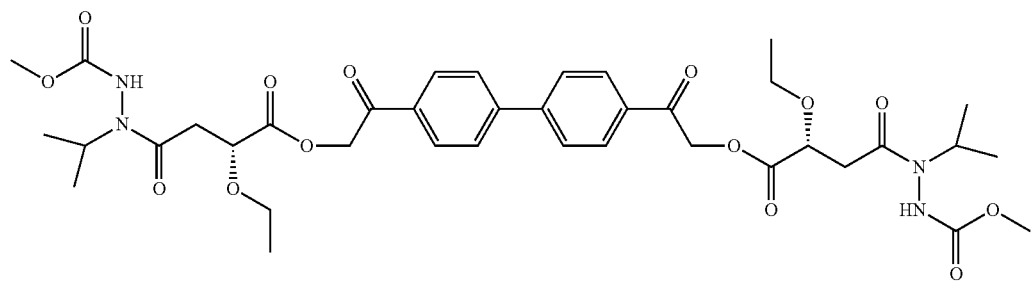

EXAMPLE MD-6

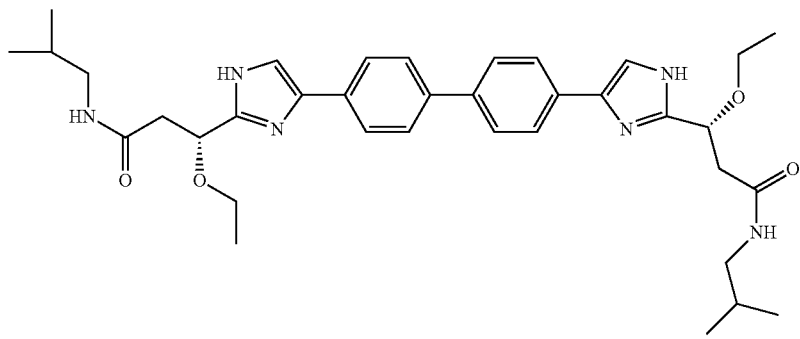 [SMILES: CCO[C@H](CC(=O)NCC(C)C)c1nc(-c2ccc(-c3ccc(-c4c[nH]c([C@@H](CC(=O)NCC(C)C)OCC)n4)cc3)cc2)c[nH]1]

EXAMPLE MD-6

Step a

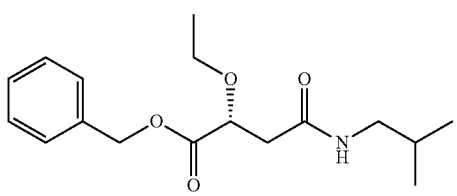 [SMILES: CCO[C@H](CC(=O)NCC(C)C)C(=O)OCc1ccccc1]

To a solution of material from MD-5, step d (212 mg, 0.842 mmol) isobutylamine (115 μL, 1.148 mmol), and HOAT (20 mg, 0.147 mmol) in anhydrous dichloromethane (1.6 mL) was added EDC (200 mg, 1.043 mmol), followed immediately by DIEA (200 μl, 1.145 mmol). The reaction was flushed briefly with $N_2$, capped and stirred at room temp for 1 h, and then the solvent was removed under a gentle stream of $N_2$ overnight. The crude product was dissolved in dichloromethane (5 mL) and purified by flash column chromatography (24 g Teledyne Isco Silica Flash Column, 100% dichloromethane to 100% ethyl acetate over 12 column volumes) to afford the title compound (161 mg) as colorless film. LC/MS Condition MD-1: [M+H]$^+$ 308; [M+Na]$^+$330, $R_f$=3.50 min; $^1$H NMR (500 MHZ, CDCl$_3$) δ 7.50-7.32 (m, 5H), 6.08 (br. s., 1H), 5.29-5.13 (m, 2H), 4.32 (dd, J=8.6, 3.7 Hz, 1H), 3.76 (dd, J=9.2, 7.0 Hz, 1H), 3.62-3.44 (m, 1H), 3.13 (dt, J=13.2, 6.5 Hz, 1H), 3.08-2.98 (m, 1H), 2.74-2.66 (m, 1H), 2.62-2.52 (m, 1H), 1.76 (dt, J=13.4, 6.7 Hz, 1H), 1.24 (t, J=7.0 Hz, 3H), 0.92 (dd, J=6.6, 0.4 Hz, 6H).

EXAMPLE MD-6

Step b

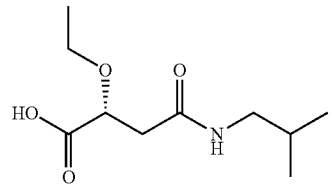

To a solution of material from MD-6, step a (177 mg, 0.576 mmol) in methanol (75 mL) was added 30% palladium on carbon (78 mg). The reaction was flushed with $N_2$, securely capped, then purged well with $H_2$ gas and allowed to stir at room temp for 18 h under an atmosphere of $H_2$. The reaction was filtered through a 45μ frit and the solvent was removed in vacuo to afford the title compound (126.9 mg) as colorless oil. LC/MS Condition MD-1: [M+Na]$^+$240, $R_f$=2.39 min; $^1$H NMR (500 MHZ, CDCl$_3$) δ 7.88-7.43 (brs, 1H), 6.45 (t, J=5.3 Hz, 1H), 4.26 (dd, J=7.1, 4.8 Hz, 1H), 3.87-3.73 (m, 1H), 3.64-3.48 (m, 1H), 3.23-3.02 (m, 2H), 2.80 (dd, J=15.2, 4.8 Hz, 1H), 2.67 (dd, J=15.3, 7.2 Hz, 1H), 1.80 (dt, J=13.4, 6.7 Hz, 1H), 1.25 (t, J=7.0 Hz, 3H), 0.93 (d, J=6.7 Hz, 6H).

EXAMPLE MD-6

Step c

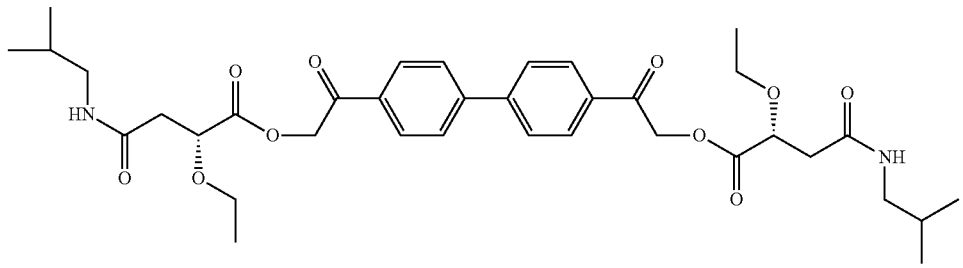 [SMILES: CCO[C@H](CC(=O)NCC(C)C)C(=O)OCC(=O)c1ccc(-c2ccc(C(=O)COC(=O)[C@@H](CC(=O)NCC(C)C)OCC)cc2)cc1]

To a suspension of 1,1'-([1,1'-biphenyl]-4,4'-diyl)bis(2-bromoethanone) (51 mg, 0.129 mmol) and material from MD-6, step b (62.1 mg, 0.286 mmol) in anhydrous ACN (3.5 mL) at 0° C. was slowly added DIEA (80 μL, 0.458 mmol). The resulting off white suspension was flushed well with N$_2$, securely capped and allowed to stir for 18 h while slowly warming to room temp. The solvent was removed in vacuo and the crude product was purified by flash column chromatography (80 g Teledyne Isco Silica Flash Column, 100% dichloromethane to 100% ethyl acetate over 11 column volumes) to afford the title compound (79.7 mg) as white solid. LC/MS Condition MD-1: [M+Na]$^+$669, R$_t$=3.93 min; $^1$H NMR (500 MHZ, CDCl$_3$) δ 8.12-7.98 (m, 4H), 7.84-7.69 (m, 4H), 6.18 (t, J=5.7 Hz, 2H), 5.58-5.38 (m, 4H), 4.51 (dd, J=8.4, 4.1 Hz, 2H), 3.93-3.82 (m, 2H), 3.62 (dq, J=9.0, 7.1 Hz, 2H), 3.24-3.06 (m, 4H), 2.89 (dd, J=14.8, 4.1 Hz, 2H), 2.72 (dd, J=14.9, 8.3 Hz, 2H), 1.80 (dt, J=13.4, 6.7 Hz, 2H), 1.29 (t, J=7.0 Hz, 6H), 0.95 (d, J=6.7 Hz, 12H).

EXAMPLE MD-6

To a 48 mL pressure bottle under N$_2$ was added material from Example MD-6, step c (42.3 mg, 0.063 mmol), ammonium acetate (170 mg, 2.205 mmol), imidazole (25 mg, 0.367 mmol) and anhydrous toluene (3 mL). The reaction was flushed with N$_2$, securely capped and heated at 100° C. for 6 h. The solvent was evaporated off under a gentle stream of N$_2$ and the crude product was purified by reverse phase preparative HPLC conditions MD-1 using a gradient from 30% solvent B/70% solvent A to 100% solvent B over 10 min to give the TFA salt of the title compound (8.3 mg) as white solid. LC/MS Condition MD-1: [M+H]$^+$ 629, R$_t$=3.21 min; $^1$H NMR (500 MHZ, CD$_3$OD) δ 7.94 (s, 2H), 7.89 (s, 8H), 5.18 (t, J=6.5 Hz, 2H), 3.71-3.61 (m, 4H), 3.05-3.01 (m, 4H), 2.95 (dd, J=8.2, 6.6 Hz, 4H), 1.78 (dt, J=13.5, 6.7 Hz, 2H), 1.27 (t, J=6.9 Hz, 6H), 0.92 (dd, J=6.6, 0.7 Hz, 12H).
Analytical HPLC MD-A: R$_t$=25.67 min, λ=220 nm
Analytical HPLC MD-B: R$_t$=25.32 min, λ=220 nm
Analytical HPLC MD-C: R$_t$=8.90 min, λ=254 nm

EXAMPLE MD-7

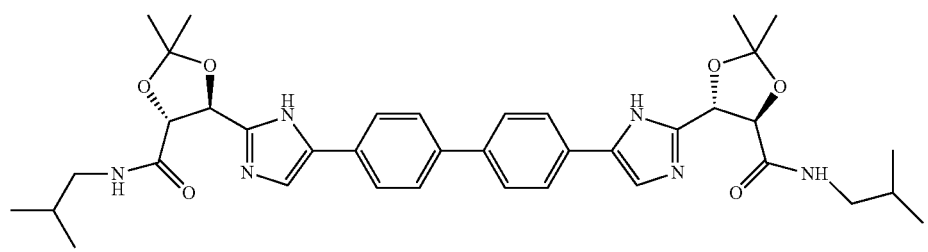 [SMILES: CC(C)CNC(=O)[C@@H]1OC(C)(C)O[C@H]1c1ncc(-c2ccc(-c3ccc(-c4cnc([C@@H]5OC(C)(C)O[C@H]5C(=O)NCC(C)C)[nH]4)cc3)cc2)[nH]1]

EXAMPLE MD-7

Step a

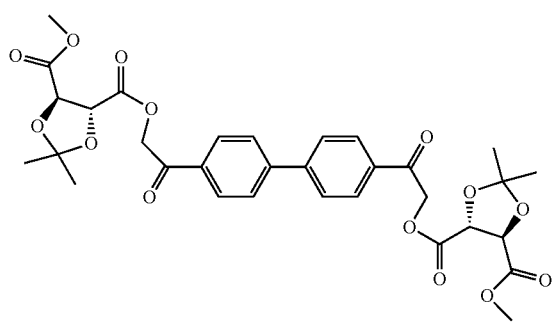 [SMILES: COC(=O)[C@@H]1OC(C)(C)O[C@H]1C(=O)OCC(=O)c1ccc(-c2ccc(C(=O)COC(=O)[C@@H]3OC(C)(C)O[C@H]3C(=O)OC)cc2)cc1]

To a suspension of 1,1'-([1,1'-biphenyl]-4,4'-diyl)bis(2-bromoethanone) (800 mg, 2.02 mmol) and (4R,5R)-5-(methoxycarbonyl)-2,2-dimethyl-1,3-dioxolane-4-carboxylic acid (BMCL, 2003, vol. 13, No. 10 p. 1713-1716) (950 mg, 4.65 mmol) in anhydrous ACN (25 mL) at 0° C. was slowly added DIEA (850 μL, 4.87 mmol). The resulting off-white suspension was flushed well with N$_2$, securely capped and allowed to stir for 18 h while slowly warming to room temp. The solvent was removed in vacuo and the crude product was purified by flash column chromatography (80 g Teledyne Isco Silica Flash Column, 100% hexanes to 70% ethyl acetate/hexanes over 11 column volumes) to afford the title compound (1.11 g) as a white solid. LC/MS Condition MD-1: [M+Na]$^+$665, R$_t$=3.79 min. $^1$H NMR (500 MHZ, CDCl$_3$) δ 8.04 (d, J=8.7 Hz, 4H), 7.77 (d, J=8.5 Hz, 4H), 5.61 (d, J=16.2 Hz, 2H), 5.44 (d, J=16.2 Hz, 2H), 5.12 (d, 2H, J=5.3 Hz), 5.07 (d, 2H, J=5.3 Hz), 3.88 (s, 6H), 1.60 (s, 6H), 1.56 (s, 6H).

EXAMPLE MD-7

Step b

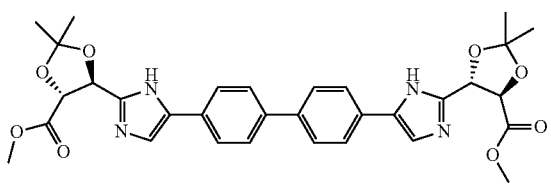 [SMILES: COC(=O)[C@@H]1OC(C)(C)O[C@H]1c1ncc(-c2ccc(-c3ccc(-c4cnc([C@@H]5OC(C)(C)O[C@H]5C(=O)OC)[nH]4)cc3)cc2)[nH]1]

To a microwave vial under N$_2$ was added material from Example MD-7, step a (108.1 mg, 0.168 mmol), ammonium acetate (330 mg, 4.28 mmol), and anhydrous toluene (4 mL). The reaction was flushed with N$_2$, securely capped and heated at 110° C. for 45 min. The reaction was then heated at 106° C. for 5 h, followed by 60° C. for 18 h. The solvent was evaporated off under a gentle stream of N$_2$, and the residue was partitioned between EtOAc and aq. satd. NaHCO$_3$. The water layer was back extracted with EtOAc, the organic layers were combined, washed with brine, dried over Na$_2$SO$_4$, filtered and evaporated to dryness. The crude product was purified by reverse phase preparative HPLC conditions MD-1 using a gradient from 25% solvent B/75% solvent A to 100% solvent B over 11 min to give the title compound (26.8 mg) as a TFA salt as a white solid. LC/MS Condition MD-1: [M+H]$^+$ 603, R$_t$=2.88 min. $^1$H NMR (500 MHZ, CD$_3$OD) δ 8.00 (s, 2H), 7.93-7.86 (m, 8H), 5.67 (d, J=6.7 Hz, 2H), 4.98 (d, J=6.7 Hz, 2H), 3.87 (s, 6H), 1.64 (s, 6H), 1.55 (s, 6H).

EXAMPLE MD-7

To a 2-5 mL microwave vial under N$_2$ was added material from Example MD-7, step b (18 mg, 0.022 mmol), 2-methylpropan-1-amine (100 mg, 1.367 mmol) and anhydrous MeOH (2 mL). The reaction was flushed with $N_2$, securely capped and heated in a microwave heating unit at 155° C. for 90 min under high power, followed by additional heating at 130° C. for 16 h under high power. The volatiles were removed under a gentle stream of $N_2$ and the crude product was purified by reverse phase preparative HPLC conditions MD-1 using a gradient from 20% solvent B/80% solvent A to 100% solvent B over 10 min to give the title compound (7.8 mg) as a TFA salt as a white solid. LC/MS Condition MD-1: $[M+H]^+$ 685, $R_t$=3.31 min; $^1$H NMR (400 MHZ, $CD_3OD$) δ 8.00 (s, 2H), 7.89 (s, 8H), 5.45 (d, J=7.7 Hz, 2H), 4.79 (d, J=7.7 Hz, 2H), 3.22-3.14 (m, 2H), 3.12-3.06 (m, 2H), 1.89 (m, 2H), 1.67 (s, 6H), 1.61 (s, 6H), 0.98-0.93 (m, 12H).

Analytical HPLC MD-A: $R_t$=25.18 min, λ=220 nm
Analytical HPLC MD-B: $R_t$=25.07 min, λ=220 nm
Analytical HPLC MD-C: $R_t$=10.66 min, λ=254 nm
Analytical HPLC MD-D: $R_t$=11.83 min, λ=254 nm

EXAMPLE MD8

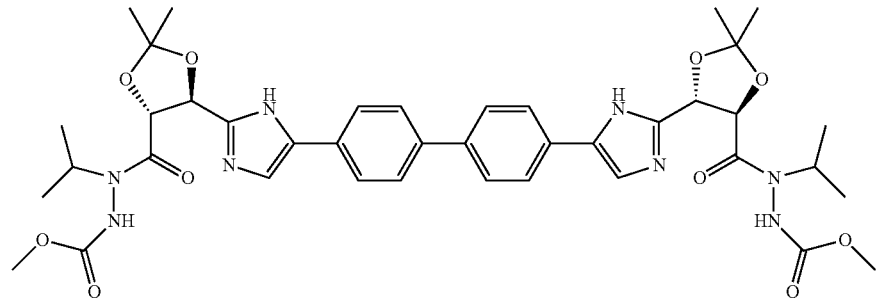

EXAMPLE MD-8

Step a

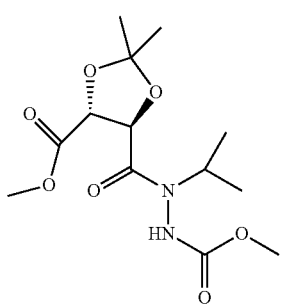

To a suspension of (4R,5R)-5-(methoxycarbonyl)-2,2-dimethyl-1,3-dioxolane-4-carboxylic acid (*BMCL*, 2003, vol. 13, #10 p. 1713-1716) (610 mg, 2.99 mmol), methyl 2-isopropylhydrazinecarboxylate (375.5 mg, 2.84 mmol), and HOAT (62 mg, 3.19 mmol) in anhydrous dichloromethane (5 mL) was added EDC (612 mg, 3.19 mmol), followed immediately by DIEA (600 μl, 1.209 mmol). The reaction was flushed briefly with N2, capped and stirred at room temp for 18 h. The reaction was diluted with dichloromethane (50 mL) and the organic layer was washed with aq. saturated $NaHCO_3$ (1×50 mL), water (1×25 mL), brine (1×50 mL), dried over $Na_2SO4$, filtered and the solvent removed in vacuo. The crude product was dissolved in dichloromethane (10 mL) and purified by flash column chromatography (120 g Teledyne Isco Silica Flash Column, 100% dichloromethane to 80% ethyl acetate/dichloromethane over 10 column volumes) to afford the title compound (320 mg) as a white solid. LC/MS Condition MD-1: $[M+H]^+$ 319, $R_t$=2.71 min; LC/MS Condition MD-2: $[M+H]^+$ 319; $[M-H]^-$ 317, $R_t$=2.09 min; $^1$H NMR (500 MHZ, $CDCl_3$) δ 5.30-5.20 (m, 1H), 5.02-4.67 (m, 2H), 3.87-3.76 (m, 6H), 1.55-1.41 (m, 6H), 1.29-1.10 (m, 6H).

EXAMPLE MD-8

Step b

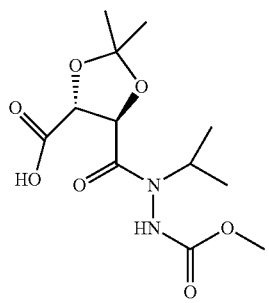 [SMILES: COC(=O)NN(C(=O)[C@@H]1OC(C)(C)O[C@H]1C(=O)O)C(C)C]

To a solution of material from MD-8, step a (315 mg, 0.990 mmol) in a mixture of dioxane (5 mL) and water (3 mL) was added sodium hydroxide (47.4 mg, 2.06 mmol) slowly over 30 min. The reaction was stirred at room temp for 1 h, cooled briefly in a −20° C. freezer and quenched with 1.0 N HCl (1.4 mL). The reaction was diluted with dichloromethane (80 mL) and water (4 mL), the organic layer was separated, dried over $Na_2SO_4/MgSO_4$, filtered and the sol vent removed in vacuo to give the title compound (255 mg) as a white solid. LC/MS Condition MD-1: [M+Na]⁺327, $R_t$=2.38 min.

EXAMPLE MD-8

Step c

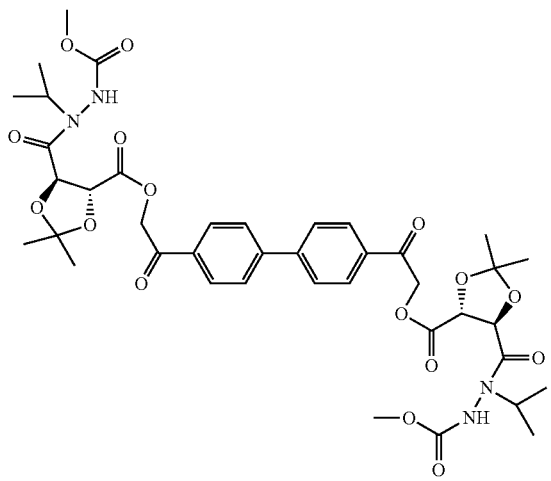 [SMILES: COC(=O)NN(C(=O)[C@@H]1OC(C)(C)O[C@H]1C(=O)OCC(=O)c1ccc(-c2ccc(C(=O)COC(=O)[C@@H]3OC(C)(C)O[C@H]3C(=O)N(NC(=O)OC)C(C)C)cc2)cc1)C(C)C]

To a suspension of 1,1'-([1,1'-biphenyl]-4,4'-diyl)bis(2-bromoethanone) (130 mg, 0.328 mmol) and material from MD-8, step b (250 mg, 0.822 mmol) in anhydrous ACN (15 mL) at 0° C. was slowly added DIEA (200 µL, 1.145 mmol). The reaction was flushed well with $N_2$, securely capped and allowed to stir for 18 h while slowly warming to room temp. The reaction was diluted with dichloromethane (10 mL), cooled to −20° C. for 1 h and the white precipitate was filtered off to give the title compound (184 mg) as a white solid. LC/MS Condition MD-1: [M+Na]⁺865, $R_t$=3.708 min.

EXAMPLE MD-8

To a dry 5-10 mL microwave vial under $N_2$ was added material from MD-8, step c (82 mg, 0.097 mmol), ammonium acetate (280 mg, 3.63 mmol), imidazole (40 mg, 0.588 mmol) and anhydrous toluene (3.5 mL). The resulting suspension was flushed well with $N_2$, securely capped, stirred at room temp for 5 min, then heated to 100° C. for 3.5 h, and then stirred at room temp for 18 h. The resulting crude solid was washed with toluene (3×2 mL), the solvent removed under a gentle stream of $N_2$ and the resulting crude solid was purified by reverse phase preparative HPLC conditions MD-1 using a gradient from 20% solvent B/80% solvent A to 100% solvent B over 11 min to give the title compound (10.8 mg) as a TFA salt as a white solid. LC/MS Condition MD-1: [M+H]⁺803, $R_t$=3.32 min. ¹H NMR (500 MHZ, CD₃OD) δ 7.97 (s, 2H), 7.89 (s, 8H), 5.84 (d, J=6.7 Hz, 2H), 4.96 (d, J=6.7 Hz, 2H), 4.73 (m, 2H), 3.64 (s, 6H), 1.61 (s, 6H), 1.56 (s, 6H), 1.17 (d, J=6.7 Hz, 6H), 1.12 (d, J=6.7 Hz, 6H)

Analytical HPLC MD-A: $R_t$=23.35 min, λ=220 nm
Analytical HPLC MD-B: $R_t$=23.79 min, λ=220 nm
Analytical HPLC MD-C: $R_t$=9.31 min, λ=254 nm
Analytical HPLC MD-D: $R_t$=10.05 min, λ=254 nm

EXAMPLE MD-9

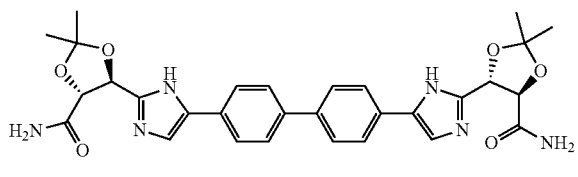 [SMILES: CC1(C)O[C@@H](C(N)=O)[C@H](c2ncc(-c3ccc(-c4ccc(-c5cnc([C@@H]6OC(C)(C)O[C@H]6C(N)=O)[nH]5)cc4)cc3)[nH]2)O1]

To a 48 mL pressure bottle under $N_2$ was added material from MD-7, step a (226 mg, 0.352 mmol), ammonium acetate (850 mg, 11.03 mmol) and anhydrous toluene (8 mL). The reaction was flushed with $N_2$, securely capped and heated at 110° C. for 18 h. The supernatant was removed and the resulting crude solid was via preparative LC/MS with the following conditions: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 30-80% B over 25 min, then a 5-min hold at 100% B; Flow: 20 mL/min to give the title compound (13.1 mg). ¹H NMR (500 MHZ, DMSO-d₆) δ 7.86 (br. s., 3H), 7.71 (br. s., 5H), 7.57-7.41 (m, 4H), 5.13 (d, J=7.3 Hz, 2H), 4.87 (br. s., 2H), 2.55 (s, 4H), 1.47 (br. s., 12H).

EXAMPLE MD-10

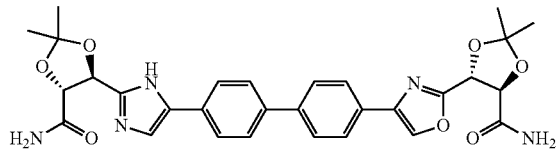

Also isolated from the reaction described in Example MD-9 was the compound shown above (7.4 mg). ¹H NMR (500 MHZ, DMSO-d₆) δ 7.84 (d, J=7.7 Hz, 4H), 7.71 (d, J=7.7 Hz, 4H), 7.62 (s, 1H), 7.54 (br. s., 1H), 7.47 (br. s., 1H), 5.13 (d, J=7.0 Hz, 1H), 5.12-5.10 (d, J=7.3 Hz, 1H), 4.89 (d, J=7.0 Hz, 1H), 4.81 (d, J=7.3 Hz, 1H), 2.55 (s, 2H), 2.51 (br. s., 2H), 1.47 (br. s., 6H), 1.43 (d, 6H).

EXAMPLE MD-11

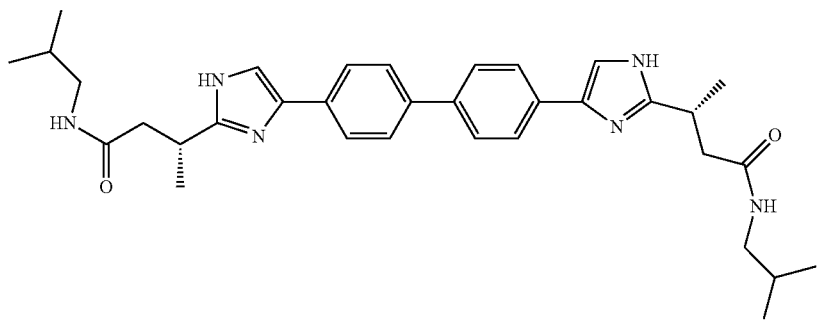 [SMILES: CC(C)CNC(=O)C[C@@H](C)c1nc(-c2ccc(-c3ccc(-c4c[nH]c([C@H](C)CC(=O)NCC(C)C)n4)cc3)cc2)c[nH]1]

EXAMPLE MD-11

Step a

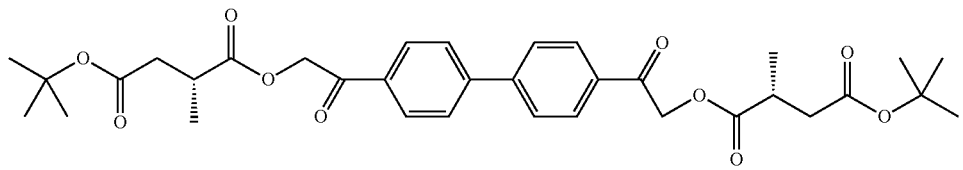 [SMILES: C[C@H](CC(=O)OC(C)(C)C)C(=O)OCC(=O)c1ccc(-c2ccc(C(=O)COC(=O)[C@H](C)CC(=O)OC(C)(C)C)cc2)cc1]

To an ice-cold suspension of 1,1'-([1,1'-biphenyl]-4,4'-diyl)bis(2-bromoethanone) (1.2 g, 3.03 mmol), (R)-4-(tert-butoxy)-2-methyl-4-oxobutanoic acid (prepared according to the procedure described in *J. Org. Chem.*, V. 64 (1999), issue 17, p. 6411-6417) (1.72 g, 9.14 mmol) in anhydrous acetonitrile (30 mL) was slowly added DIEA (1.6 mL, 9.16 mmol). The reaction was flushed well with $N_2$, securely capped and allowed to stir for 18 h while slowly warming to room temp. The solvent was removed in vacuo and the crude product was purified by flash column chromatography (120 g Teledyne Isco Silica Flash Column, 100% hexanes to 100% ethyl acetate over 11 column volumes) to afford the title compound (980 mg) as a white solid. LC/MS Condition MD-1: [M+Na]+633, $R_f$=4.42 min; $^1$H NMR (400 MHZ, $CDCl_3$) δ 8.03 (d, J=8.3 Hz, 4H), 7.75 (d, J=8.5 Hz, 4H), 5.57-5.39 (m, 2H), 5.37-5.25 (m, 2H), 3.19-2.98 (m, 2H), 2.79 (dd, J=16.4, 7.7 Hz, 2H), 2.43 (dd, J=16.3, 6.5 Hz, 2H), 1.51-1.45 (m, 18H), 1.35 (d, J=7.3 Hz, 6H).

EXAMPLE MD-11

Step b

To a dry 48 mL pressure bottle under $N_2$ was added material from MD-11, step a (807 mg, 1.321 mmol), ammonium acetate (3.06 g, 39.7 mmol), imidazole (540 mg, 7.93 mmol) and anhydrous toluene (20 mL). The reaction was flushed well with $N_2$, securely capped and stirred at room temp for 5 min, then heated at 110° C. oil for 18 h. Evaporate off the solvent under a gentle stream of $N_2$ while warming to 60° C. for 7 h. The residue was dissolved in a mixture of ethyl acetate (425 mL) and water (50 mL) and the organic layer was extracted with water (5×50 mL), brine (1×50 mL), dried over $Na_2SO_4$, filtered and the solvent removed in vacuo. The crude product was purified by flash column chromatography (24 g Teledyne Isco Silica Flash Column (equilibrated with 1% triethylamine in dichloromethane), 100% dichloromethane to 100% ethyl acetate over 10 column volumes) to afford the title compound (448 mg) as a yellow solid. LC/MS Condition MD-1: [M+H]+ 571, $R_f$=3.15 min. $^1$H NMR (500 MHZ, $CDCl_3$) δ 10.15 (br. s., 1H), 9.91-9.71 (m, 1H), 7.85 (d, J=6.4 Hz, 3H), 7.72-7.45 (m, 6H), 7.25 (br. s., 1H), 3.55-3.34 (m, 2H), 2.82-2.61 (m, 4H), 1.55-1.41 (m, 24H).

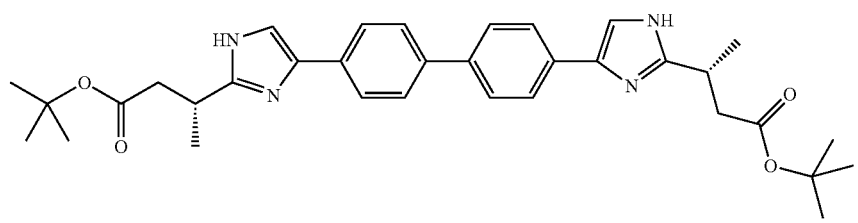 [SMILES: C[C@H](CC(=O)OC(C)(C)C)c1nc(-c2ccc(-c3ccc(-c4c[nH]c([C@H](C)CC(=O)OC(C)(C)C)n4)cc3)cc2)c[nH]1]

EXAMPLE MD-11

Step c

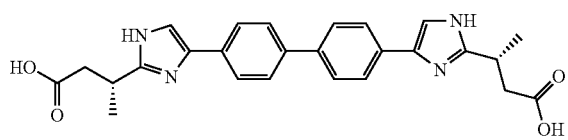 [SMILES: C[C@H](CC(=O)O)c1nc(-c2ccc(-c3ccc(-c4c[nH]c([C@H](C)CC(=O)O)n4)cc3)cc2)c[nH]1]

To a rapidly swirled solution of material from MD-11, step b (141.6 mg, 0.248 mmol) in anhydrous dichloromethane (5 mL) was added TFA (8 mL, 104 mmol). The resulting red/orange solution was allowed to stand at room temp for 90 min, and then the volatiles were removed under a gentle stream of $N_2$. The residue was suspended in dichloromethane (20 mL) and the solvent was removed under a gentle stream of $N_2$. The residue was suspended in toluene (25 mL), sonicated briefly and the solvent was removed in vacuo to give the title compound (182.7 mg) as a tan solid as a TFA salt. LC/MS Condition MD-1: [M+H]$^+$ 4591, $R_t$=2.35 min; $^1$H NMR (500 MHZ, DMSO-d$_6$) δ 8.17 (s, 2H), 8.03-7.87 (m, 8H), 3.71-3.53 (m, 2H), 2.95 (dd, J=17.1, 8.4 Hz, 2H), 2.87-2.77 (m, 2H), 1.41 (d, J=7.0 Hz, 6H).

EXAMPLE MD-11

To a suspension of material from MD-11, step c (15 mg, 0.022 mmol) in anhydrous DMF (600 μL) was added isobutylamine (25 μL, 0.250 mmol), DIEA (40 μL, 0.229 mmol) and HATU (85 mg, 0.224 mmol). The resulting solution was flushed well with $N_2$, securely capped and stirred at room temp for 80 min. The reaction was diluted with DMF (1.4 mL), filtered thru a 45μ frit, and purified by reverse phase preparative HPLC conditions MD-1 using a gradient from 20% solvent B/80% solvent A to 100% solvent B over 10 min to give the title compound (8.5 mg) as a TFA salt as a white solid. LC/MS Condition MD-1: [M+H]$^+$ 569, $R_t$=3.02 min. $^1$H NMR (500 MHZ, CD$_3$OD) δ 7.94-7.78 (m, 10H), 3.77-3.65 (m, 2H), 3.07-2.94 (m, 4H), 2.88-2.77 (m, 4H), 1.76 (dt, J=13.5, 6.8 Hz, 2H), 1.52 (d, J=7.2 Hz, 6H), 0.90 (dd, J=6.7, 1.8 Hz, 12H).

EXAMPLE MD-12

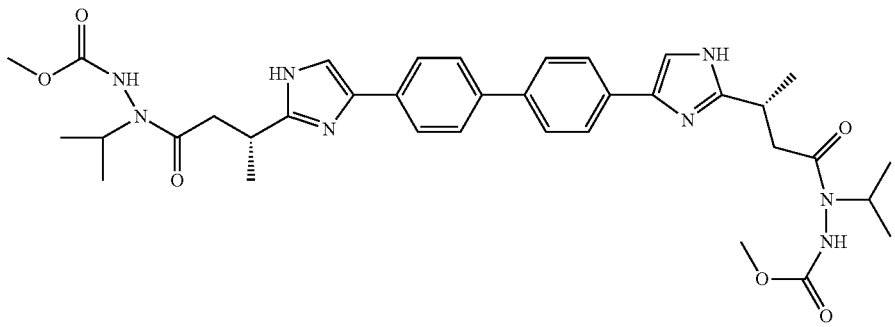 [SMILES: COC(=O)NN(C(=O)C[C@@H](C)c1nc(-c2ccc(-c3ccc(-c4c[nH]c([C@H](C)CC(=O)N(NC(=O)OC)C(C)C)n4)cc3)cc2)c[nH]1)C(C)C]

EXAMPLE MD-12

Step a

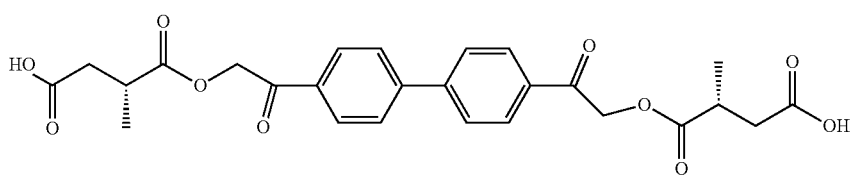 [SMILES: C[C@H](CC(=O)O)C(=O)OCC(=O)c1ccc(-c2ccc(C(=O)COC(=O)[C@H](C)CC(=O)O)cc2)cc1]

To a rapidly swirled solution of material from MD-11, step a (103 mg, 0.169 mmol) in anhydrous dichloromethane (4 mL) was added TFA (5.5 mL, 71.4 mmol). The resulting clear, colorless solution was allowed to stand at room temp for 1 h, and then the solvent was removed in vacuo. The residue was dissolved in dichloromethane and the solvent was removed in vacuo. The residue was dissolved in toluene and the solvent was removed in vacuo to give the title compound (84.7 mg) as a white solid. LC/MS Condition MD-1: [M+Na]$^+$ 521, R$_t$=3.43 min.

EXAMPLE MD-12

Step b

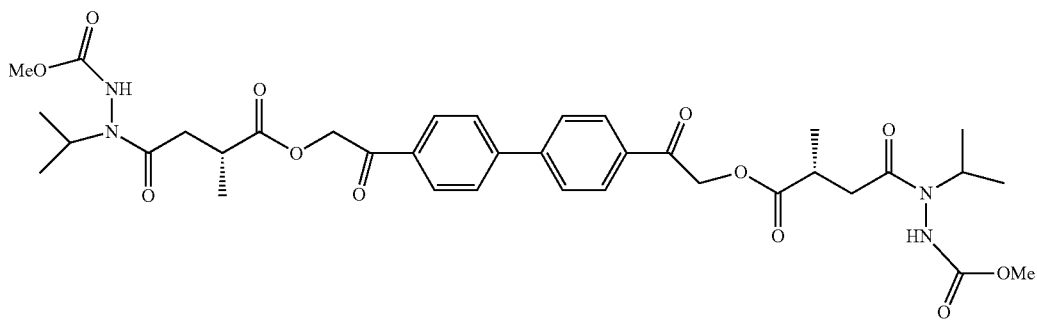 [SMILES: COC(=O)NN(C(=O)C[C@@H](C)C(=O)OCC(=O)c1ccc(-c2ccc(C(=O)COC(=O)[C@H](C)CC(=O)N(NC(=O)OC)C(C)C)cc2)cc1)C(C)C]

To a dichloromethane (2 mL) solution of material from MD-12, step a (84.7 mg, 0.170 mmol), methyl 2-isopropylhydrazinecarboxylate (60 mg, 0.454 mmol), and HOAT (10 mg, 0.073 mmol) was added EDC (51 mg, 0.266 mmol) and DIEA (150 µL, 0.037 mmol). The reaction was flushed with N$_2$, securely capped and allowed to stir at room temp for 18 h. The solvent was removed in vacuo and the residue was purified by flash column chromatography (24 g Teledyne Isco Silica Flash Column, 100% dichloromethane to 100% ethyl acetate over 11 column volumes) to afford the title compound (136.5 mg) as a colorless film. LC/MS Condition MD-1: [M+H]$^+$ 727, R$_t$=3.85 min.

EXAMPLE MD-12

To a dry 10-20 mL microwave vial under N$_2$ was added material from MD-12, step b (136.5 mg, 0.188 mmol), ammonium acetate (455 mg, 5.90 mmol), imidazole (83 mg, 1.219 mmol) and anhydrous toluene (3.0 mL). The reaction was flushed with N$_2$, securely capped and placed in a 110° C. oil bath for 18 h. The crude reaction was purified by reverse phase preparative HPLC conditions MD-1 using a gradient from 25% solvent B/75% solvent A to 100% solvent B over 10 min to give the impure title compound (15.3 mg) as a TFA salt as a pale yellow solid. LC/MS Condition MD-1: [M+H]$^+$ 687, R$_t$=2.83 min.

The impure title compound was then further purified by via preparative LC/MS with the following conditions: Column: XBridge C18, 19×mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min, then a 5-min hold at 100% B; Flow: 20 mL/min to give the pure title compound (3.1 mg) as a white film. $^1$H NMR (500 MHZ, CD$_3$OD) δ 7.89-7.56 (m, 8H), 7.32 (d, J=8.2 Hz, 2H), 4.80-4.61 (m, 2H), 3.80 (d, J=19.8 Hz, 6H), 3.54 (dt, J=14.0, 6.8 Hz, 2H), 3.00 (dd, J=16.3, 7.9 Hz, 1H), 2.88 (dd, J=16.4, 8.3 Hz, 1H), 2.67 (dd, J=16.4, 5.9 Hz, 1H), 2.54 (dd, J=16.2, 6.7 Hz, 1H), 1.38 (d, J=7.0 Hz, 6H), 1.19-0.96 (m, 12H).

EXAMPLE MD-13

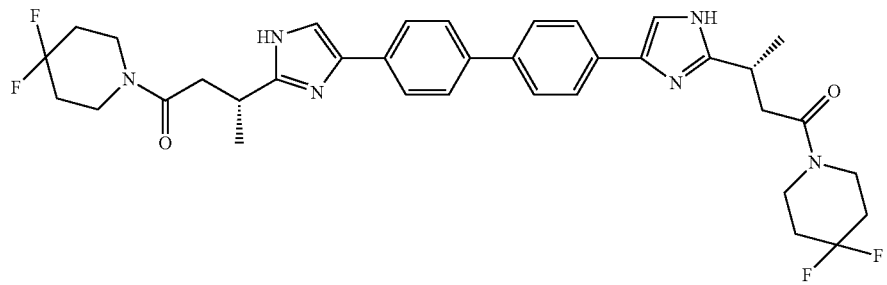 [SMILES: C[C@H](CC(=O)N1CCC(F)(F)CC1)c1nc(-c2ccc(-c3ccc(-c4c[nH]c([C@H](C)CC(=O)N5CCC(F)(F)CC5)n4)cc3)cc2)c[nH]1]

To a dry vial under N$_2$ was added material from MD-11, step c (25 mg, 0.036 mmol), 4,4-difluoropiperidine, 1.00 HCl (50 mg, 0.317 mmol), HOAT (15 mg, 0.110 mmol), anhydrous dichloromethane (2.5 mL), EDC (50 mg, 0.261 mmol), and DIEA (105 µL, 0.601 mmol). The reaction was flushed briefly with N$_2$, capped, stirred at room temp for 80 min, and then treated with DMAP (19 mg, 0.156 mmol) and allowed to stir at room temp for 70 h. The reaction was then treated with additional EDC (56 mg, 0.292 mmol) and DIEA (105 µL, 0.601 mmol), flushed with N$_2$ and allowed to stir at room temp for 24 h. The solvent was removed under a gentle stream of N$_2$ and the residue was diluted with DMF (1.4 mL), filtered thru a 45µ frit, and purified by reverse phase preparative HPLC conditions MD-1 using a gradient from 20% solvent B/80% solvent A to 100% solvent B over 11 min to give the impure TFA salt of the title compound (18 mg) as a colorless film. LC/MS Condition MD-1: [M+H]$^+$ 665, R$_t$=3.03 min.

The impure title compound was further purified via preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 50-90% B over 30 min, then a 7-min hold at 100% B; Flow: 20 mL/min. to give the pure title compound (6.0 mg). $^1$H NMR (500 MHZ, DMSO-d$_6$) δ 12.13 (br. s., 1H), 11.86 (br. s., 1H), 8.00-7.40 (m, 10H), 3.62 (d, J=7.3 Hz, 10H), 2.99 (dd, J=15.1, 6.9 Hz, 2H), 2.62 (dd, J=15.4, 6.9 Hz, 2H), 2.09-1.81 (m, 8H), 1.29 (d, J=6.7 Hz, 6H).

EXAMPLE MD-14

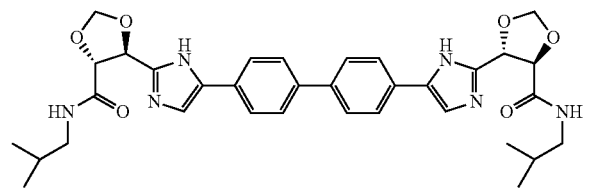 [SMILES: CC(C)CNC(=O)[C@@H]1OCO[C@H]1c1ncc(-c2ccc(-c3ccc(-c4cnc([C@@H]5OCO[C@H]5C(=O)NCC(C)C)[nH]4)cc3)cc2)[nH]1]

EXAMPLE MD-14

Step a

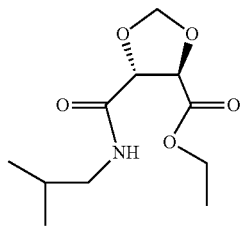 [SMILES: CCOC(=O)[C@@H]1OCO[C@H]1C(=O)NCC(C)C]

To a solution of (4R,5R)-5-(ethoxycarbonyl)-1,3-dioxolane-4-carboxylic acid (prepared according to the procedure described in *BOMCL*, 2002, vol. 10, #5, 1567-1580) (200 mg, 1.052 mmol), 2-methylpropan-1-amine (100 mg, 1.367 mmol), HOAT (40 mg, 0.294 mmol) in dichloromethane (8 mL) was added EDC (250 mg, 1.304 mmol) and DIEA (220 μL, 1.260 mmol). The reaction was flushed with N$_2$, securely capped and stirred at room temp for 18 h. The reaction was washed once with water, once with brine, dried over Na$_2$SO$_4$, filtered and the solvent was removed in vacuo to give the title compound (240 mg) as colorless oil. LC/MS Condition MD-1: [M+H]$^+$ 246, R$_t$=2.99 min.

EXAMPLE MD-14

Step b

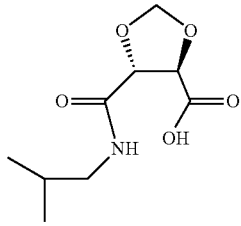

To a solution of material from MD-14, step a (240 mg, 0.979 mmol) in a mixture of dioxane (5 mL) and water (3 mL) was slowly added sodium hydroxide (45 mg, 1.125 mmol). The reaction was stirred at room temp for 80 min, cooled to −20° C. and quenched with aq. 1N HCl (1.5 mL, 1.50 mmol). The reaction was diluted with dichloromethane (80 mL) and the organic layer was washed with water (3 mL). The water layer was back extracted with additional dichloromethane (30 mL), the organic layers were combined, dried over Na$_2$SO$_4$/MgSO$_4$, filtered and the solvent was removed in vacuo to give the title compound (152 mg) as a white solid. LC/MS Condition MD-1: [M+H]$^+$ 218, R$_t$=2.33 min. $^1$H NMR (500 MHZ, CDCl$_3$) δ 6.84 (br. s., 1H), 5.26 (s, 1H), 5.24 (s, 1H), 4.62 (d, J=6.7 Hz, 1H), 4.56 (d, J=6.7 Hz, 1H), 3.26-3.16 (m, 2H), 1.87 (m, 1H), 0.97 (d, J=6.7 Hz, 6H).

EXAMPLE MD-14

Step c

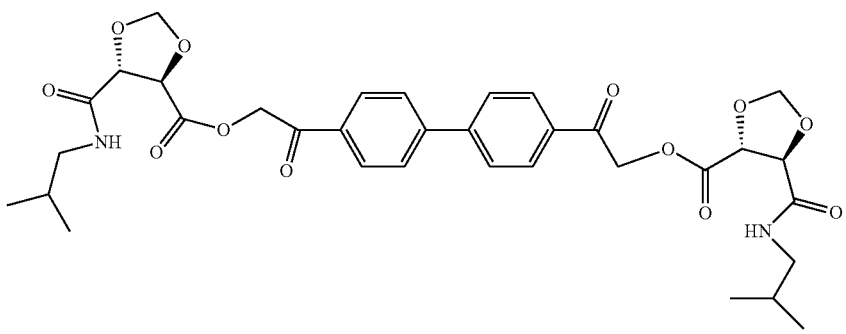 [SMILES: CC(C)CNC(=O)[C@@H]1OCO[C@H]1C(=O)OCC(=O)c1ccc(-c2ccc(C(=O)COC(=O)[C@@H]3OCO[C@H]3C(=O)NCC(C)C)cc2)cc1]

To an ice cold suspension of 1,1'-([1,1'-biphenyl]-4,4'-diyl)bis(2-bromoethanone) (125 mg, 0.316 mmol), material from MD-14, step b (152 mg, 0.700 mmol) in anhydrous acetonitrile (7 mL) was slowly added DIEA (180 µL, 1.031 mmol). The reaction was flushed well with N$_2$, securely capped and allowed to stir for 60 h while slowly warming to room temp. The solvent was removed in vacuo and the crude product was purified by flash column chromatography (40 g Teledyne Isco Silica Flash Column, 100% dichloromethane to 100% ethyl acetate over 9 column volumes) to afford the title compound (173 mg) as a white solid. LC/MS Condition MD-1: [M+H]$^+$ 669, R$_t$=3.72 min; $^1$H NMR (500 MHZ, CDCl$_3$) δ 8.03 (d, J=8.4 Hz, 4H), 7.77 (d, J=8.4 Hz, 4H), 6.68 (t, J=5.9 Hz, 2H), 5.66 (d, J=16.3 Hz, 2H), 5.43 (d, J=16.3 Hz, 2H), 5.35 (s, 2H), 5.31 (s, 2H), 5.08 (d, J=3.5 Hz, 2H), 5.02 (d, J=3.5 Hz, 2H), 3.18 (m, 4H), 1.84 (m, 2H), 0.96 (d, J=6.7 Hz, 12H).

EXAMPLE MD-14

To a 48 mL pressure bottle under N$_2$ was added material from MD-14, step c (88 mg, 0.132 mmol), ammonium acetate (350 mg, 4.54 mmol), imidazole (50.8 mg, 0.746 mmol) and anhydrous toluene (4 mL). The reaction was flushed well with N$_2$, securely capped and heated at 110° C. for 10 h. The solvent was removed in vacuo and the crude product was purified by reverse phase preparative HPLC conditions MD-1 using a gradient from 30% solvent B/70% solvent A to 100% solvent B over 11 min to give the TFA salt of the title compound (6.9 mg) as a white solid. LC/MS Condition MD-1: [M+H]$^+$ 629, R$_t$=3.14 min. $^1$H NMR (500 MHZ, CD$_3$OD) δ 7.95 (s, 2H), 7.89 (m, 8H), 5.54 (d, J=4.9 Hz, 2H), 5.50 (s, 2H), 5.25 (s, 2H), 4.89 (d, J=4.9 Hz, 2H), 3.14 (d, J=7.0 Hz, 4H), 2.67 (s, 2H), 1.94-1.86 (m, 2H), 0.96 (d, J=6.7 Hz, 12H). Analytical HPLC MD-A: R$_t$=23.22 min, λ=220 nm
Analytical HPLC MD-B: R$_t$=23.62 min, λ=220 nm.
Analytical HPLC MD-C: R$_t$=8.49 min, λ=254 nm
Analytical HPLC MD-D: R$_t$=9.42 min, λ=254 nm

EXAMPLE MD-15

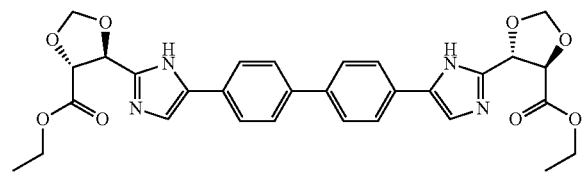 [SMILES: CCOC(=O)[C@@H]1OCO[C@H]1c1ncc(-c2ccc(-c3ccc(-c4cnc([C@@H]5OCO[C@H]5C(=O)OCC)[nH]4)cc3)cc2)[nH]1]

EXAMPLE MD-15

Step a

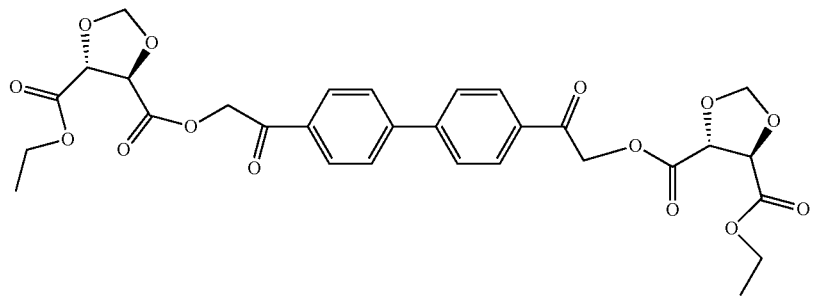 [SMILES: CCOC(=O)[C@@H]1OCO[C@H]1C(=O)OCC(=O)c1ccc(-c2ccc(C(=O)COC(=O)[C@@H]3OCO[C@H]3C(=O)OCC)cc2)cc1]

To an ice cold suspension of 1,1'-([1,1'-biphenyl]-4,4'-diyl)bis(2-bromoethanone) (870 mg, 2.197 mmol), (4R,5R)-5-(ethoxycarbonyl)-1,3-dioxolane-4-carboxylic acid (prepared according to the procedure described in BOMC, 2002, vol. 10, No.#5, 1567-1580) (1.25 g, 6.57 mmol) in anhydrous acetonitrile (25 mL) was slowly added DIEA (1.3 mL, 7.44 mmol). The reaction was flushed well with N$_2$, securely capped and allowed to stir for 18 h while slowly warming to room temp. The solvent was removed in vacuo and the crude product was purified by flash column chromatography (80 g Teledyne Isco Silica Flash Column, 100% hexanes to 70% ethyl acetate/hexanes over 11 column volumes) to afford the title compound (865 mg) as a white solid. LC/MS Condition MD-1: [M+Na]$^+$ 637, R$_t$=3.65 min $^1$H NMR (500 MHZ, CDCl$_3$) δ 8.04 (d, J=8.5 Hz, 4H), 7.78 (d, J=8.5 Hz, 4H), 5.62 (d, J=16.3 Hz, 2H), 5.46 (d, J=16.3 Hz, 2H), 5.37 (s, 2H), 5.35 (s, 2H), 5.11 (d, J=3.4 Hz, 2H), 5.00 (d, J=3.4 Hz, 2H), 4.33 (q, J=7.2 Hz, 4H), 1.37 (t, J=7.2 Hz, 6H).

EXAMPLE MD-15

To a dry 10-20 mL microwave vial under N$_2$ was added material from Example MD-15, step a (100 mg, 0.163 mmol), ammonium acetate (365 mg, 4.74 mmol) and anhydrous toluene (4 mL). The reaction was flushed well with N$_2$, securely capped and heated at 60° C. for 18 h. The reaction was heated further at 80° C. for 3 h, then 90° C. for 2.5 h. The solvent was removed under a gentle stream of N$_2$ and the crude product was purified by reverse phase preparative HPLC conditions MD-1 using a gradient from 20% solvent B/80% solvent A to 100% solvent B over 11 min to give the TFA salt of the impure title compound (18 mg) as an off-white solid. The impure title compound was further purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-min hold at 100% B; Flow: 20 mL/min to give the pure title compound (5.4 mg). LC/MS Condition MD-1: [M+H]$^+$ 575, R$_t$=2.76 min; $^1$H NMR (500 MHZ, DMSO-d$_6$) δ 12.86 (br. s., 1H), 12.53 (br. s., 1H), 8.09-7.56 (m, 10H), 5.33-5.02 (m, 8H), 4.21 (d, J=7.0 Hz, 4H), 1.23 (t, J=7.0 Hz, 6H).

EXAMPLE MD-16

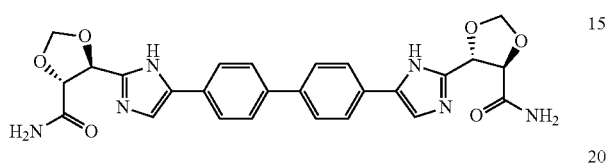

To a dry 10-20 mL microwave vial under N$_2$ was added material from Example MD-15, step a (100 mg, 0.163 mmol), ammonium acetate (330 mg, 4.74 mmol) and anhydrous toluene (4 mL). The reaction was flushed well with N$_2$, securely capped, stirred at room temp for 10 min, and then placed in a 110° C. oil bath for 4.5 h. The reaction was partitioned between EtOAc and aq. satd. NaHCO$_3$, organic layer was removed and evaporated to dryness. LC/MS Condition MD-2: [M+H]$^+$ 575, [M–H]$^-$ 573; R$_t$=2.58 min.

The resulting residue was purified via preparative LC/MS with the following conditions: Column: XBridge C18, 19×200 mm, 5-µm particles; Mobile Phase A: 5:95 methanol:water with 10-mM ammonium acetate; Mobile Phase B: 95:5 methanol:water with 10-mM ammonium acetate; Gradient: 30-70% B over 20 min, then a 5-min hold at 100% B; Flow: 20 mL/min to give the title compound (1.0 mg); $^1$H NMR (500 MHZ, DMSO-d$_6$) δ 12.86 (br. s., 1H), 12.53 (br. s., 1H), 8.09-7.56 (m, 10H), 5.33-5.02 (m, 8H), 4.21 (d, J=7.0 Hz, 4H), 1.23 (t, J=7.0 Hz, 6H).

EXAMPLE MD-17

EXAMPLE MD-17

Step a

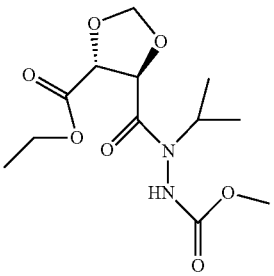

To a solution of (4R,5R)-5-(ethoxycarbonyl)-1,3-dioxolane-4-carboxylic acid (prepared according to the procedure described in BOMC, 2002, vol. 10, No. 5, 1567-1580) (490 mg, 2.58 mmol), methyl 2-isopropylhydrazinecarboxylate (388 mg, 1.139 mmol), HOAT (80 mg, 0.588 mmol) in dichloromethane (6 mL) was added EDC (600 mg, 3.13 mmol) and DIEA (600 µL, 3.44 mmol). The reaction was flushed with N$_2$, securely capped and stirred at room temp for 18 h. The solvent was evaporated off under a gentle stream of N2 and the crude product was purified by flash column chromatography (120 g Teledyne Isco Silica Flash Column, 100% dichloromethane to 80% ethyl acetate/hexanes over 11 column volumes) to afford the title compound (60 mg) as a white solid. LC/MS Condition MD-1: [M+Na]$^+$327, R$_t$=2.54 min.

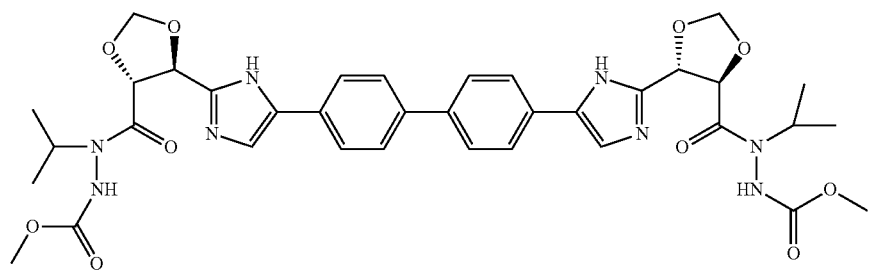

EXAMPLE MD-17

Step b

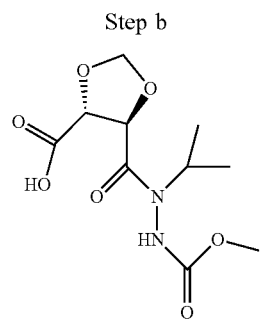

To a solution of material from MD-17, step a (60 mg, 0.197 mmol) in a mixture of dioxane (3 mL) and water (1 mL) was added sodium hydroxide (11 mg, 0.275 mmol). The reaction was securely capped, stirred at room temp for 1 h, cooled to −20° C. and quenched with 1 N HCl (400 μL). The reaction was diluted with dichloromethane (70 mL) and water (3 mL), the organic layer was removed, dried over $Na_2SO_4/MgSO_4$, filtered and the solvent was removed in vacuo to give the title compound (52 mg) as a colorless solid. LC/MS Condition MD-1: $[M+H]^+$ 277, $[M+Na]^+$ 299; $R_t$=1.96 min.

EXAMPLE MD-17

Step c

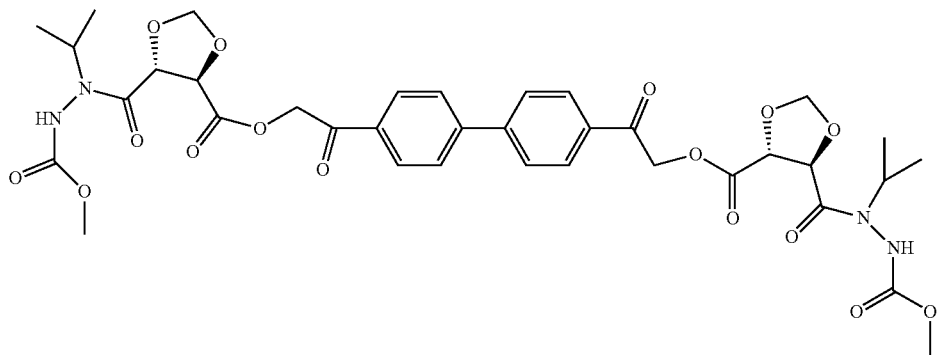 [SMILES: COC(=O)NN(C(=O)[C@@H]1OCO[C@H]1C(=O)OCC(=O)c1ccc(-c2ccc(C(=O)COC(=O)[C@@H]3OCO[C@H]3C(=O)N(NC(=O)OC)C(C)C)cc2)cc1)C(C)C]

To an ice cold suspension of 1,1'-([1,1'-biphenyl]-4,4'-diyl)bis(2-bromoethanone) (37 mg, 0.093 mmol), material from MD-17, step b (52 mg, 0.188 mmol) in anhydrous acetonitrile (3 mL) was slowly added DIEA (60 μL, 0.344 mmol). The reaction was flushed well with $N_2$, securely capped and allowed to stir for 18 h while slowly warming to room temp. The solvent was removed in vacuo and the crude product was purified by flash column chromatography (12 g Teledyne Isco Silica Flash Column, 100% hexanes to 70% ethyl acetate/hexanes over 10 column volumes) to afford the title compound (35 mg) as a white solid. LC/MS Condition MD-1: $[M+H]^+$ 787, $[M+Na]^+$ 809; $R_t$=3.42 min.

EXAMPLE MD-17

To 15 ml, pressure bottle under $N_2$ was added material from MD-17, step c (35 mg, 0.044 mmol), ammonium acetate (115 mg, 1.492 mmol) and anhydrous toluene (4 mL). The reaction was flushed with $N_2$ and immediately put in a 79° C. oil bath which was ramping up to 101° C. The reaction was heated at 101° C. for 5 h. The solvent was removed under a gentle stream of $N_2$ and the crude product was purified by reverse phase preparative HPLC conditions MD-1 using a gradient from 30% solvent B/70% solvent A to 100% solvent B over 11 min to give the TFA salt of the title compound (7.0 mg) as a white solid. LC/MS Condition MD-1: $[M+H]^+$ 747, $R_t$=2.94 min; $^1H$ NMR (500 MHZ, $CD_3OD$) δ 8.03-7.76 (m, 10H), 5.77-5.08 (m, 8H), 4.77-4.66 (m, 2H), 3.81-3.53 (m, 6H), 1.29-1.07 (m, 12H).

Analytical HPLC MD-A: $R_t$=20.63 min, λ=220 nm
Analytical HPLC MD-B: $R_t$=21.73 min, λ=220 nm
Analytical HPLC MD-C: $R_t$=7.04 min, λ=254 nm
Analytical HPLC MD-D: $R_t$=7.50 min, λ=254 nm

EXAMPLE MD-18

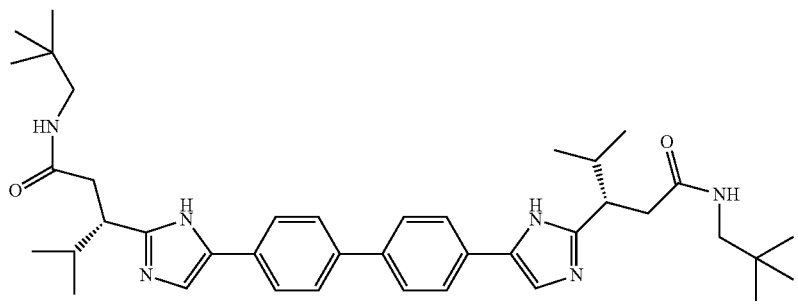 [SMILES: CC(C)[C@H](CC(=O)NCC(C)(C)C)c1ncc(-c2ccc(-c3ccc(-c4cnc([C@@H](CC(=O)NCC(C)(C)C)C(C)C)[nH]4)cc3)cc2)[nH]1]

EXAMPLE MD-18

Step a

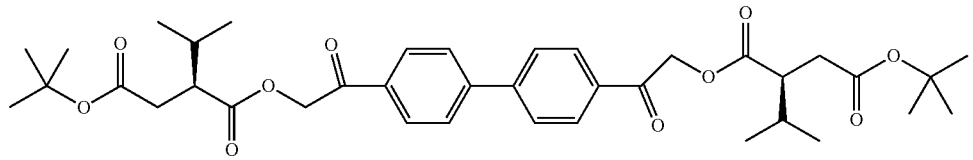 [SMILES: CC(C)[C@H](CC(=O)OC(C)(C)C)C(=O)OCC(=O)c1ccc(-c2ccc(C(=O)COC(=O)[C@@H](CC(=O)OC(C)(C)C)C(C)C)cc2)cc1]

To an ice cold suspension of 1,1'-([1,1'-biphenyl]-4,4'-diyl)bis(2-bromoethanone) (750 mg, 1.894 mmol), (S)-4-(tert-butoxy)-2-isopropyl-4-oxobutanoic acid (prepared according to the procedure described in *J. Org. Chem*, 1999, 64, 6411-6417) (859 mg, 3.97 mmol) in anhydrous acetonitrile (20 mL) was slowly added DIEA (1.1 mL, 6.30 mmol). The reaction was flushed well with $N_2$, securely capped and allowed to stir for 18 h while slowly warming to room temp. The solvent was removed in vacuo and the crude product was purified by flash column chromatography (80 g Teledyne Isco Silica Flash Column, 100% hexanes to 60% ethyl acetate/hexanes over 10 column volumes) to afford the title compound (1.23 g) as a white solid. LC/MS Condition MD-1: [M+Na]$^+$666; $R_t$=4.76 min; $^1$H NMR (500 MHZ, CDCl$_3$) δ 8.04 (d, J=8.4 Hz, 4H), 7.75 (d, J=8.5 Hz, 4H), 5.51 (d, J=16.2 Hz, 2H), 5.30 (d, J=16.3 Hz, 2H), 2.94-2.87 (m, 2H), 2.75 (dd, J=16.6, 10.5 Hz, 2H), 2.43 (dd, J=16.6, 4.1 Hz, 2H), 2.24-2.14 (m, 2H), 1.47 (s, 18H), 1.08/1.06 (two overlapping doublets, J=6.8, 7.0 Hz, 12H).

EXAMPLE MD-18

Step b

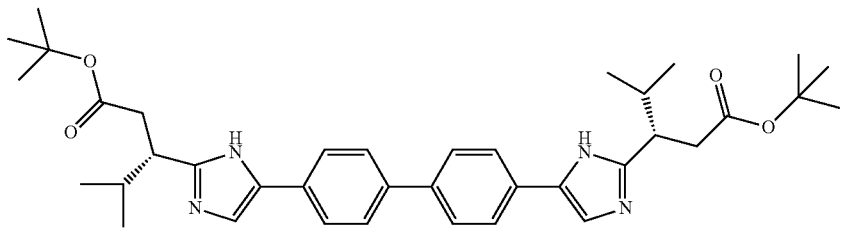 [SMILES: CC(C)[C@H](CC(=O)OC(C)(C)C)c1ncc(-c2ccc(-c3ccc(-c4cnc([C@@H](CC(=O)OC(C)(C)C)C(C)C)[nH]4)cc3)cc2)[nH]1]

To 15 mL pressure bottle under $N_2$ was added material from MD-18, step a (232 mg, 0.348 mmol), ammonium acetate (812 mg, 10.53 mmol), imidazole (141 mg, 2.071 mmol) and anhydrous toluene (5.5 mL). The reaction was flushed with $N_2$ and immediately put in a 78° C. oil bath which was programmed for 120° C. The reaction was heated at 120° C. for 18 h. The solvent was removed under a gentle stream of $N_2$ and the crude product was purified by flash column chromatography (24 g Teledyne Isco Silica Flash Column, 100% dichloromethane to 100% ethyl acetate over 12 column volumes) to afford the title compound (80.2 mg) as a yellow solid. LC/MS Condition MD-1: [M+H]$^+$ 627; $R_t$=3.42 min; $^1$H NMR (500 MHZ, CD$_3$OD) δ 7.89-7.63 (m, 8H), 7.34 (br. s., 2H), 3.07 (ddd, J=10.3, 7.8, 5.5 Hz, 2H), 2.87-2.69 (m, 4H), 2.61-2.46 (m, 2H), 1.99 (dd, J=14.2, 6.9 Hz, 2H), 1.32 (s, 18H), 1.04 (d, J=6.7 Hz, 6H), 0.88 (d, J=6.9 Hz, 6H).

EXAMPLE MD-18

Step c

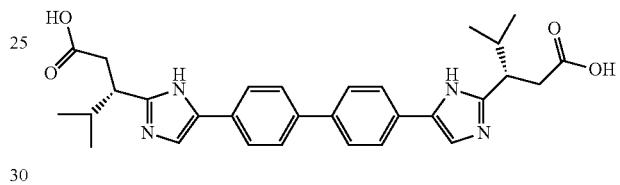

To a solution of material from MD-18, step b (80.2 mg, 0.128 mmol) in anhydrous dichloromethane (5 mL) was added TFA (8 mL) with vigorous swirling. The resulting solution was allowed to stand at room temp for 70 min, then the volatiles were removed under a gentle stream of $N_2$ to give the title compound (134.8 mg) as a TFA salt as a yellow film. LC/MS Condition MD-1: [M+H]$^+$ 515; $R_t$=2.97 min.

EXAMPLE MD-18

Step d

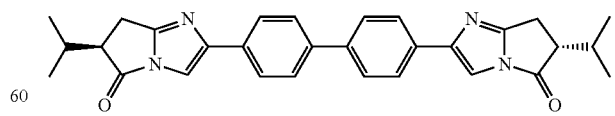

Regiochemistry of cyclization onto the imidazole was not determined

To a suspension of material from MD-18, step c (460 mg, 0.537 mmol) in dichloromethane (14 mL) was added DIEA (540 µL, 3.09 mmol), followed immediately by HATU (877 mg, 2.306 mmol). The resulting suspension was flushed briefly with N2, capped, sonicated briefly and stirred at room temp for 1.5 h. The reaction was filtered thru a 45μ frit and purified by flash column chromatography (80 g Teledyne Isco Silica Flash Column, 100% dichloromethane to 50% dichloromethane:50% ethyl acetate over 5 column volumes) to afford the title compound (170 mg) as a pale yellow solid. LC/MS Condition MD-1: [M+H]$^+$ 479; R$_t$=4.23 min; $^1$H NMR (400 MHZ, CDCl$_3$) δ 7.97-7.88 (m, 4H), 7.78-7.66 (m, 4H), 7.55 (s, 2H), 3.39 (ddd, J=8.2, 5.3, 3.1 Hz, 2H), 3.29-3.19 (m, 2H), 2.92 (dd, J=18.6, 3.3 Hz, 2H), 2.38-2.24 (m, 2H), 1.13 (d, J=6.8 Hz, 6H), 1.03 (d, J=6.8 Hz, 6H).

EXAMPLE MD-18

A dry 0.5-2.0 mL microwave vial under N$_2$ was charged with material from MD-18, step d (20.2 mg, 0.042 mmol), pivalic acid (44 μL, 0.378 mmol), 2,2-dimethylpropan-1-amine (29.2 mg, 0.355 mmol) and anhydrous NMP (700 μL). The reaction was flushed briefly with N$_2$, securely capped and placed in a 75° C. sand bath for 10 min. The reaction was then heated in a microwave heating unit for 1 min. at 110° C. under high power. LC/MS Condition MD-1: [M+H]$^+$ 653; R$_t$=3.52 min. The reaction was diluted with DMF (700 μL) and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-100% B over 15 min, then a 10-min hold at 100% B; Flow: 20 mL/min. to give the title compound (22.8 mg). $^1$H NMR (500 MHZ, DMSO-d$_6$) δ 12.32-11.66 (m, 2H), 7.98-7.57 (m, 10H), 7.49 (br. s., 2H), 3.21-3.09 (m, 2H), 2.88 (dd, J=13.4, 6.7 Hz, 2H), 2.82-2.67 (m, 4H), 2.56 (br. s., 2H), 2.00-1.88 (m, 2H), 0.87 (dd, J=14.2, 6.6 Hz, 12H), 0.74 (s, 18H).

EXAMPLE MD-19

To a solution material from Example MD-18, step d (24 mg, 0.050 mmol) and pivalic acid (52 μL, 0.450 mmol) in anhydrous NMP (600 μL) is added (2-chlorophenyl)methanamine (54 mg, 0.381 mmol). The reaction is flushed briefly with argon, securely capped and heated to 85° C. for 3.25 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 min, then a 5-min hold at 100% B; Flow: 20 mL/min to give the pure title compound (28 mg). LC/MS Condition MD-2: [M+H]$^+$ 761, 763, [M–H]$^-$ 759, 761; R$_t$=3.62 min. $^1$H NMR (400 MHz, DMSO-d$_6$) δ 12.12 (br. s., 1H), 11.82 (br. s., 1H), 8.45 (t, J=5.8 Hz, 2H), 7.84 (d, J=8.3 Hz, 3H), 7.78-7.56 (m, 5H), 7.50 (s, 1H), 7.41-7.24 (m, 2H), 7.19-6.98 (m, 2H), 6.96-6.77 (m, 3H), 4.46-4.21 (m, 2H), 4.06 (dd, J=16.7, 4.9 Hz, 2H), 3.21-3.00 (m, 2H), 2.93-2.69 (m, 2H), 2.55 (dd, J=14.7, 4.9 Hz, 2H), 2.02-1.78 (m, 2H), 0.87/0.83 (two overlapping doublets, J=6.8, 6.8 Hz, 12H).

EXAMPLE MD-20 to MD-32

Example MD-20 to MD-32 are prepared using the general procedure as outlined in Example MD-19. In the Examples below, all LC/MS data were obtained under LC/MS Condition MD-2.

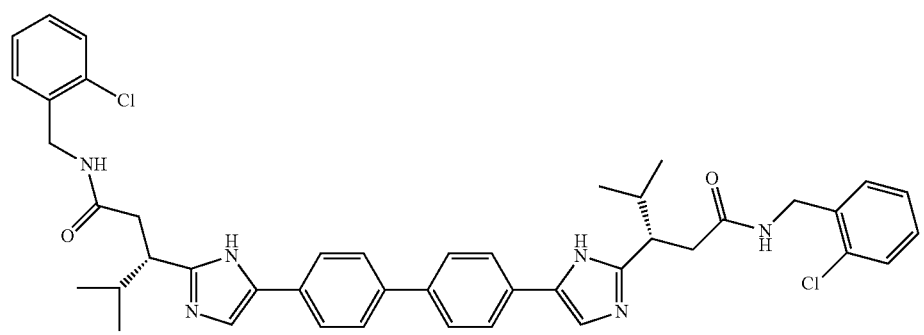 [SMILES: CC(C)[C@H](CC(=O)NCc1ccccc1Cl)c1ncc(-c2ccc(-c3ccc(-c4cnc([C@@H](CC(=O)NCc5ccccc5Cl)C(C)C)[nH]4)cc3)cc2)[nH]1]

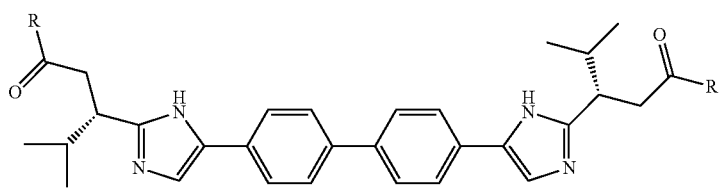
| Example | R | RT (min) | Obs. Mass ion (M + H)+ | Obs. Mass ion (M − H)− |
|---|---|---|---|---|
| MD-20 | ⸺NH-CH2-C(cyclopropyl)-CH2-O-Et | 2.81 | 737.8 | 735.9 |
| MD-21 | ⸺NH-CH2-(pinanyl) | 4.2 | 785.8 | 783.9 |
| MD-22 | ⸺NH-CH2-adamantyl | 4.03 | 809.7 | 807.8 |
| MD-23 | ⸺NH-CH2-C(phenyl)(cyclohexyl) | 4.05 | 857.8 | 855.8 |
| MD-24 | ⸺N(Me)-CH2-C(=O)-NEt2 | 2.96 | 767.7 | 765.7 |
| MD-25 | ⸺N(Me)-CH2-C(=O)-NH-tBu | 2.85 | 767.8 | — |
| MD-26 | ⸺N(iPr)(nBu) | 3.7 | 709.8 | 707.9 |
| MD-27 | ⸺N(neopentyl)-CH2CH2-(oxazolidinone) | 3.18 | 879.7 | 877.8 |

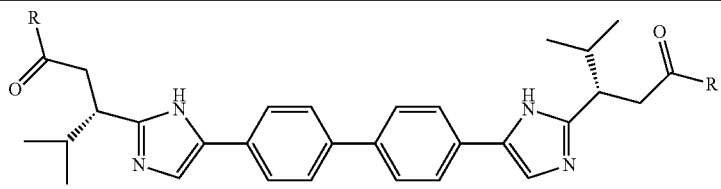

| Example | R | RT (min) | Obs. Mass ion (M + H)+ | Obs. Mass ion (M − H)− |
|---|---|---|---|---|
| MD-28 | ![structure] | 3.89 | 901.7 | 899.8 |
| MD-29 | ![structure] | 2.93 | 831.6 | 829.7 |
| MD-30 | ![structure] | 2.7 | 711.6 | 709.7 |
| MD-31 | ![structure] | 2.81 | 643.5 | 641.6 |
| MD-32 | ![structure] | 3.97 | 865.6 | 863.8 |

EXAMPLE MD-33

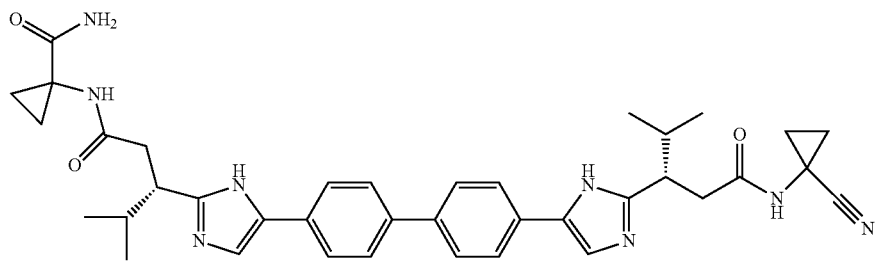 [SMILES: CC(C)[C@H](CC(=O)NC1(C#N)CC1)c1ncc(-c2ccc(-c3ccc(-c4cnc([C@@H](CC(=O)NC5(C(N)=O)CC5)C(C)C)[nH]4)cc3)cc2)[nH]1]

To a solution of Example MD-19, step a (17.0 mg, 0.036 mmol) and pivalic acid (36.4 μL, 0.313 mmol) in anhydrous NMP is added 1-aminocyclopropanecarbonitrile/1.0 HCl (35 mg, 0.295 mmol), followed by DIEA (52 μL, 0.298 mmol). The reaction is flushed with N₂, securely capped, and placed in a 75° C. sand bath for 2 h and 45 min. The reaction is further heated in a microwave reactor at 100° C. for 1 h under high power. The crude material was purified via preparative HPLC with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 15 min, then a 5-min hold at 100% B; Flow: 20 mL/min to give the pure title compound (3.4 mg). LC/MS Condition MD-2: [M+H]+ 661, [M−H]− 659; $R_t$=2.71 min.

EXAMPLE MD-34

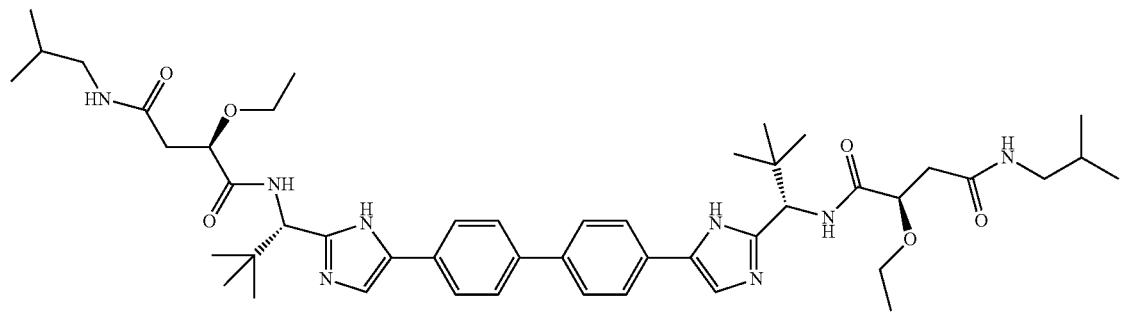 [SMILES: CCO[C@H](CC(=O)NCC(C)C)C(=O)N[C@H](c1ncc(-c2ccc(-c3ccc(-c4cnc([C@@H](NC(=O)[C@@H](CC(=O)NCC(C)C)OCC)C(C)(C)C)[nH]4)cc3)cc2)[nH]1)C(C)(C)C]

To a solution of (1S,1'S)-1,1'-(5,5'-([1,1'-biphenyl]-4,4'-diyl)bis(1H-imidazole-5,2-diyl))bis(2,2-dimethylpropan-1-amine)/4.0 HCl (see patent application WO2013106520; 110 mg, 0.183 mmol), material from Example MD-6, step b (32.4 mg, 0.149 mmol) and HATU (70 mg, 0.184 mmol) in anhydrous CH$_2$Cl$_2$ (3 mL) is added DIEA (100 μL, 0.573 mmol). The reaction is flushed briefly with argon, securely capped and allowed to stir at room temp for 18 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-80% B over 15 min, then a 5-min hold at 100% B; Flow: 20 mL/min to give the pure title compound (26.4 mg). LC/MS Condition MD-1: [M+H]+ 855, $R_t$=3.79 min. $^1$H NMR (600 MHZ, DMSO-d$_6$) δ 12.12 (br. s., 2H), 7.94-7.50 (m, 12H), 4.89 (d, J=9.5 Hz, 2H), 4.23 (d, J=6.6 Hz, 2H), 3.64-3.48 (m, 4H), 3.03-2.77 (m, 4H), 2.50-2.29 (m, 4H), 1.66 (dt, J=13.3, 6.6 Hz, 2H), 1.18 (t, J=6.6 Hz, 6H), 0.95 (s, 18H), 0.83 (d, J=6.6 Hz, 12H).

EXAMPLE MD-35

To a suspension of material from Example MD-18, step c (64 mg, 0.066 mmol) in dichloromethane (4 mL) is added HOAT (50 mg, 0.367 mmol), isobutylamine (65.2 μL, 0.656 mmol), EDC (95 mg, 0.496 mmol) and DIEA (115 μL, 0.658 mmol). The resulting solution is flushed briefly with N$_2$, capped and stirred at room temp for 18 h. Additional EDC (60 mg, 0.313 mmol), DIEA (70 μL, 0.401 mmol) and isobutylamine (200 μL, 2.01 mmol) is added, the reaction is flushed reaction briefly with N$_2$, securely capped and stirred at room temp for 18 h. The solvent is removed under a gentle stream of N$_2$ and the crude product is purified by preparative LC/MS with the following conditions: Column: XBridge C18, 19×200 mm, 5-μm particles; Mobile Phase A: 5:95 methanol:water with 10-mM ammonium acetate; Mobile Phase B: 95:5 methanol:water with 10-mM ammonium acetate; Gradient: 60-100% B over 30 min, then a 5-min hold at 100% B; Flow: 20 mL/min. to give the title compound (4.5 mg). LC/MS Condition MD-1: [M+H]+ 625; $R_t$=3.32 min.

EXAMPLE MD-36 TO MD-40

Example MD-36 to MD-40 were prepared using the general procedure outlined in Example MD-13, except using material from Example MD-11, step c. Note: in Example MD-38 and Example MD-40, THF was used as the solvent in place of dichloromethane. For the Examples below, all LC/MS data was obtained under Condition MD-1.

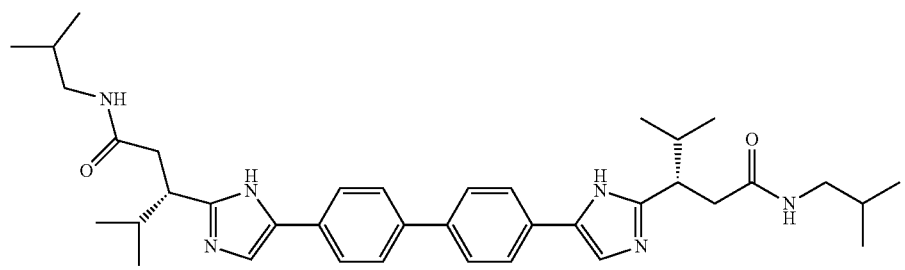 [SMILES: CC(C)CNC(=O)C[C@H](c1ncc(-c2ccc(-c3ccc(-c4cnc([C@@H](CC(=O)NCC(C)C)C(C)C)[nH]4)cc3)cc2)[nH]1)C(C)C]

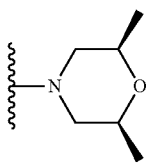

| Example | R | $R_t$ (min) | Obs. Mass ion $(M + H)^+$ |
|---|---|---|---|
| MD-36 | 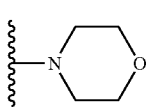 | 2.82 | 653.4 |
| MD-37 | 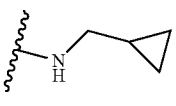 [SMILES: *NCC1CC1] | 2.58 | 597.4 |
| MD-38 | 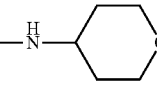 | 2.90 | 565.4 |
| MD-39 | 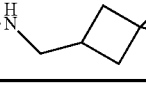 | 2.65 | 625.4 |
| MD-40 | 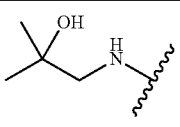 | 2.96 | 665.4 |

EXAMPLE MD-41 TO MD-54

Example MD-41 to MD-54 were prepared using the general procedure outlined in Example MD-19, except using material from Example MD-18, step d. Note: In the examples where the reagent was a salt, DIEA (8.3 mole equivalents) was added to the reaction. For the Examples below, all LC/MS data was obtained using Condition MD-1.

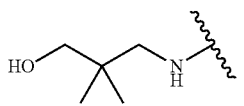 [SMILES: *NCC(C)(C)CO]

| Example | R | $R_t$ (min) | Obs. Mass ion $(M + H)^+$ |
|---|---|---|---|
| MD-41 | 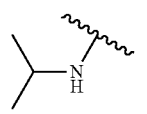 | 3.03 | 657.6 |
| MD-42 |  | 3.12 | 685.6 |
| MD-43 |  | 3.20 | 625.5 |

-continued
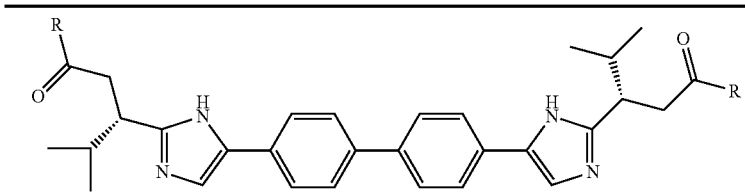
| Example | R | $R_t$ (min) | Obs. Mass ion (M + H)⁺ |
|---|---|---|---|
| MD-44 | propyl-N-CH₂-cyclopropyl | 3.61 | 705.6 |
| MD-45 | 2-ethylbutyl-NH- | 3.71 | 681.5 |
| MD-46 | diisobutylamino- | 3.81 | 738.6 |
| MD-47 | 2-methyl-2-phenylpropyl-NH- | 3.75 | 777.6 |
| MD-48 | isopropyl-NH-C(O)-CH₂-N(CH₃)- | 3.25 | 739.6 |
| MD-49 | neopentyl-N(CH₃)- | 3.55 | 681.6 |
| MD-50 | tetrahydropyran-4-yl-N(CH₃)- | 2.83 | 709.6 |
| MD-51 | H₂N-C(O)-C(CH₃)₂-CH₂-NH- | 3.00 | 711.5 |
| MD-52 | isopropyl-N(CH₂Ph)- | 3.69 | 777.6 |
| MD-53 | 4-methyl-3-oxopiperazin-1-yl | 2.90 | 707.5 |
| MD-54 | (1-hydroxycyclobutyl)methyl-NH- | 3.14 | 681.5 |

-continued

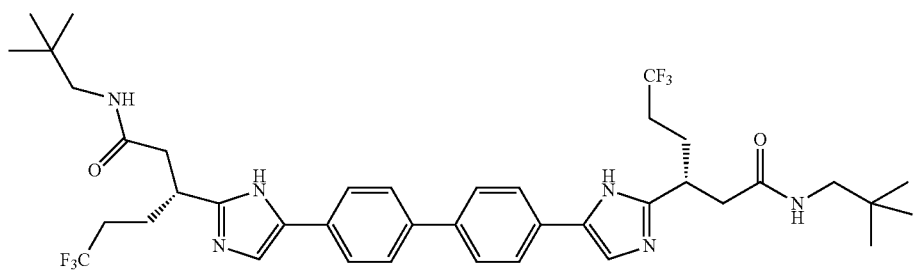

| Example | R | $R_t$ (min) | Obs. Mass ion $(M + H)^+$ |
|---|---|---|---|

EXAMPLE MD-55

[Structure of MD-55]

EXAMPLE MD-55

Step a

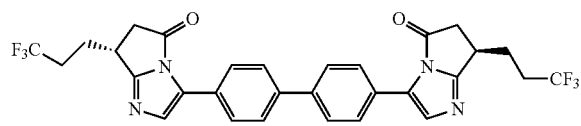 [SMILES: O=C1C[C@@H](CCC(F)(F)F)c2ncc(-c3ccc(-c4ccc(-c5cnc6n5C(=O)C[C@H]6CCC(F)(F)F)cc4)cc3)n21]

Regiochemistry of cyclization onto the imidazole was not determined

Following the general procedure as described in Example MD-18, step d, except using the material from Example MD-1, step C (290 mg, 0.301 mmol), the title compound is obtained as a white solid. $^1$H NMR (400 MHz, CDCl$_3$) δ 8.02-7.84 (m, 4H), 7.81-7.65 (m, 4H), 7.57 (s, 2H), 3.60-3.37 (m, 4H), 2.86 (dd, J=17.9, 2.9 Hz, 2H), 2.80-2.64 (m, 2H), 2.54-2.35 (m, 2H), 2.24-2.08 (m, 4H). LC/MS Condition MD-1; [M+H]$^+$ 651.4, $R_t$=3.18 min.

EXAMPLE 55

Example MD-55 was prepared using the general procedure outlined in Example MD-19. LC/MS Condition MD-1; [M+H]$^+$ 761.6, $R_t$=3.3.60 min.

EXAMPLE MD-56 TO MD-57

Example MD-56 was prepared using the general procedure outlined in Example MD-19, except using material from Example MD-55, step a and N-isopropylcyclopropanamine Note that because of isopropylamine contamination in the amine precursor, Example MD-57 was also isolated. For the Examples below, $R_t$ was obtained using LC/MS Condition MD-1.

[Structure with R and R$_1$ substituents]

| Example | R | R$_1$ | $R_t$ (min) | Obs. Mass ion $(M + H)^+$ |
|---|---|---|---|---|
| MD-56 | N-isopropyl-cyclopropyl | N-isopropyl-cyclopropyl | 3.50 | 785.6 |

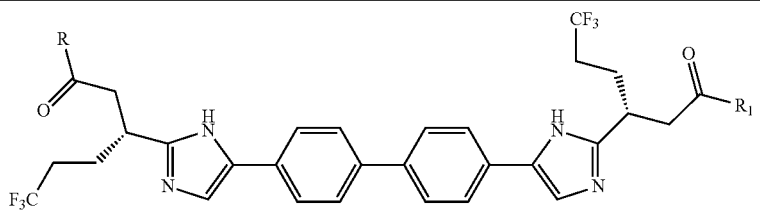

| Example | R | R₁ | $R_t$ (min) | Obs. Mass ion $(M + H)^+$ |
|---|---|---|---|---|
| MD-57 | | | 3.40 | 745.5 |

EXAMPLE MD-58

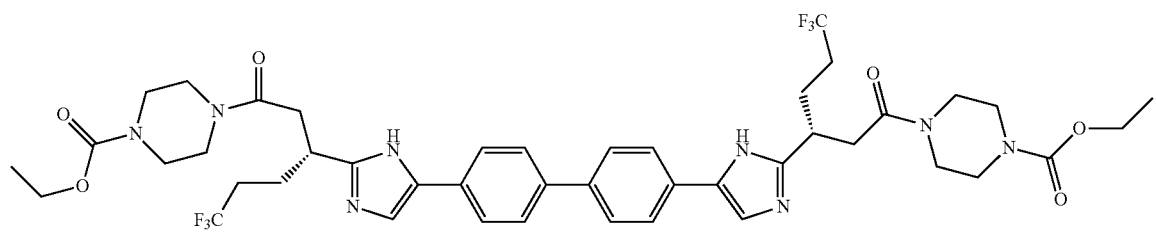

The title compound was prepared following the general procedure described in Example MD-3. Note: in this example, DIEA (200 µL, 1.15 mmol) was added to the reaction. LC/MS Condition MD-1: [M+H]⁺903.5, $R_t$=3.22 min.

EXAMPLE MD-59 TO MD-60

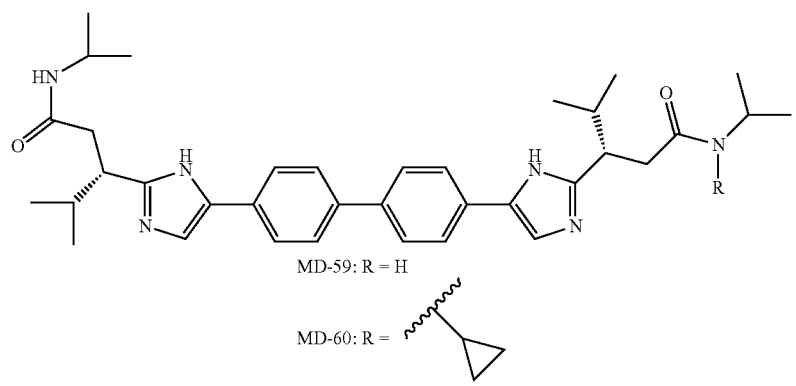

To a dry microwave vial under N₂ is added Example MD-18, step d (20 mg, 0.042 mmol), pivalic acid (43.1 µL, 0.371 mmol) and anhydrous NMP (700 µL). The reaction is flushed with N₂, then treated with N-(propan-2-yl)cyclopropanamine (23 µl, 0.169 mmol). The reaction was securely capped and placed in a 75° C. sand bath for 10 min, and then heated with a microwave unit for 3 h at 130° C. under high power. The crude material was purified via preparative LC/MS with the following conditions to afford Example MD-59 and MD-60: Column: XBridge C18, 19×mm, 5-µm particles; Mobile Phase A: 5:95 methanol:water with 10-mM ammonium acetate; Mobile Phase B: 95:5 methanol:water with 10-mM ammonium acetate; Gradient: 40-100% B over 16 min, then a 5-min hold at 100% B; Flow: 20 mL/min.

Note that the origin of the final products is likely because of contamination of the starting amine.

Example MD-59: LC/MS Condition MD-1: [M+H]⁺ 597.5, $R_t$=3.22 min.

Example MD-60: LC/MS Condition MD-1: [M+H]⁺ 637.6, $R_t$=3.36 min.

EXAMPLE MD-61

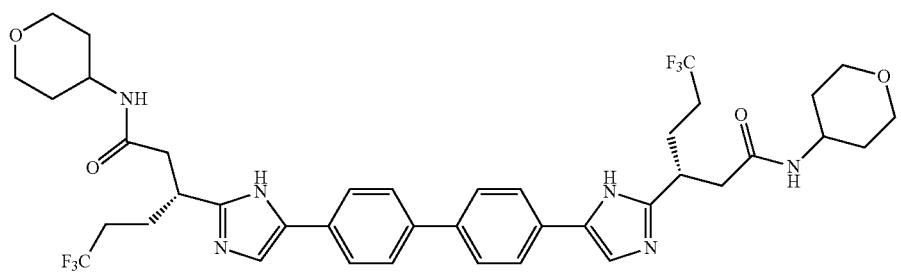 [SMILES: O=C(C[C@@H](CCC(F)(F)F)c1ncc(-c2ccc(-c3ccc(-c4cnc([C@H](CCC(F)(F)F)CC(=O)NC5CCOCC5)[nH]4)cc3)cc2)[nH]1)NC1CCOCC1]

The title compound was prepared according to the general procedure as described in Example MD-2. LC/MS Condition MD-1: [M+H]$^+$ 789.5, $R_t$=3.09 min.

EXAMPLE B1

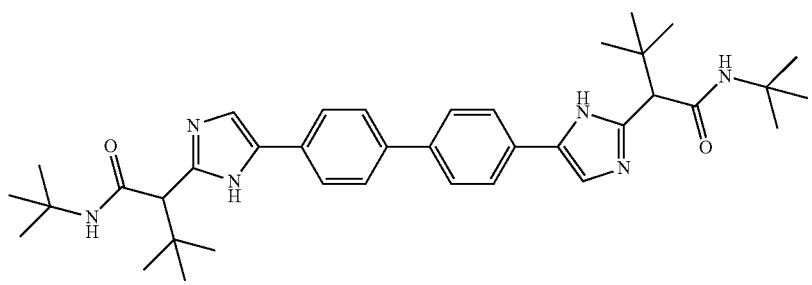 [SMILES: CC(C)(C)NC(=O)C(c1ncc(-c2ccc(-c3ccc(-c4cnc(C(C(=O)NC(C)(C)C)C(C)(C)C)[nH]4)cc3)cc2)[nH]1)C(C)(C)C]

EXAMPLE B1

Step a

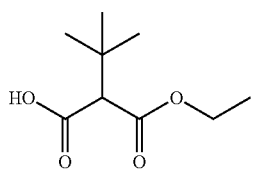

To a solution of diethyl 2-(tert-butyl)malonate (1.5 g, 6.94 mmol) in ethanol (5 mL) was added solution of KOH (0.389 g, 6.94 mmol) in ethanol (1 mL). Reaction mixture was allowed to stir at RT for overnight. The volatile component was removed in vacuo. The residue was diluted with water, extracted with hexane to remove impurities. The aqueous layer was acidified with 1.5 N HCl and extracted with in ethyl acetate (25 mL×2), washed with water (15 mL) and brine (20 mL), dried with Na$_2$SO$_4$, filtered and concentrated in vacuo to afford title compound (0.9 g) as colorless gummy material. $^1$HNMR (CDCl$_3$, δ=7.26 ppm, 400 MHz): δ 4.26 (q, J=4.80 Hz, 2H), 3.26 (s, 1H), 1.31 (t, J=7.20 Hz, 3H), 1.14 (s, 9H).

EXAMPLE B1

Step b

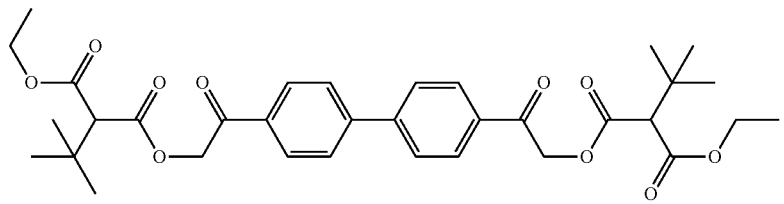 [SMILES: CCOC(=O)C(C(=O)OCC(=O)c1ccc(-c2ccc(C(=O)COC(=O)C(C(=O)OCC)C(C)(C)C)cc2)cc1)C(C)(C)C]

To a solution of 1,1'-([1,1'-biphenyl]-4,4'-diyl)bis(2-bromoethanone) (1.052 g, 2.66 mmol) in DMF (10 mL) was added Example B1, Step a (1 g, 5.31 mmol) and DIEA (5.57 mL, 31.9 mmol). The reaction mixture was stirred at RT for 3 h. The volatile component was removed in vacuo and the residue was diluted with water and extracted with DCM (10 ml×2), dried over Na$_2$SO$_4$ and concentrated in vacuo. Crude reaction mixture was purified by ISCO (40 g Redisep silica column, 34% ethyl acetate/hexanes) to afford Example B1, Step b (1.6 g) as colorless gummy material. $^1$HNMR (MeOD, δ=3.34 ppm, 400 MHz): δ 8.09 (dd, J=1.6, 4.8 Hz, 4H), 7.87 (dd, J=2.00, 6.80 Hz, 4H), 5.43-5.56 (m, 4H), 4.20 (q, J=7.20 Hz, 4H), 3.47 (s, 2H), 1.28 (t, J=7.20 Hz, 6H), 1.19 (s, 18H).

EXAMPLE B1

Step c

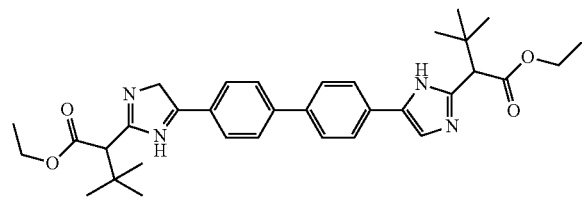 [SMILES: CCOC(=O)C(C1=NCC(c2ccc(-c3ccc(-c4cnc(C(C(=O)OCC)C(C)(C)C)[nH]4)cc3)cc2)=N1)C(C)(C)C]

To a solution of Example B1, Step b (1.6 μm, 1.637 mmol) in Xylene (20 mL) was added ammonium acetate (2.52 g, 32.7 mmol) and imidazole (0.669 g, 9.82 mmol). Reaction mixture was purged with argon for 30 min and allowed to stir at 130° C. for overnight in a sealed tube. The volatile component was removed in vacuo, diluted with water and extracted with DCM, dried over Na$_2$SO$_4$ and concentrated in vacuo. Crude material was purified by ISCO (40 g Redisep silica column, 48% ethyl acetate/hexanes) to afford diethyl Example B1, Step c (0.49 g) as yellow solid. LC/MS Condition B-12: R$_t$=2.54 min, $^1$H NMR (MeOD, δ=3.34 ppm, 400 MHz): δ 7.81 (dd, J=2.00, 6.60 Hz, 4H), 7.70 (dd, J=2.00, 6.60 Hz, 4H), 7.44 (s, 2H), 4.33-4.16 (m, 4H), 3.85 (s, 2H), 1.37-1.21 (m, 6H), 1.11 (s, 18H), LC/MS: Anal. Calcd. for [M+2H]$^+$ C$_{21}$H$_{21}$BrN$_3$O$_2$: 570.3. found 571.0 (M+1).

EXAMPLE B1

Step d

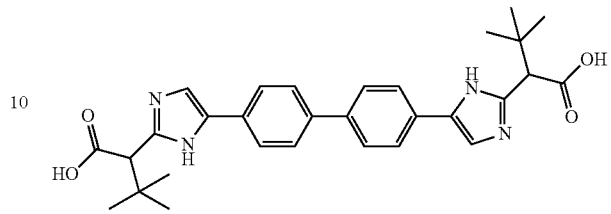

To a solution of diethyl Example B1, Step c (0.49 g, 0.859 mmol) in THF (5 mL) and methanol (5 mL) mixture was added KOH (0.482 g, 8.59 mmol) in water (5 mL). The reaction mixture was stirred at RT for 2 days. The volatile component was removed in vacuo, the aqueous layer was acidified with 1.5 N HCl, extracted with ethyl acetate (10 ml×2), washed with brine, dried over Na$_2$SO$_4$ and concentrated in vacuo to afford Example B1, Step d (0.35 g) as yellow solid. LC/MS (Condition B-12): R$_t$=1.637 min, $^1$H NMR (DMSO-d$_6$, δ=2.50 ppm, 400 MHz): δ 7.88-7.52 (m, 8H), 7.47-7.26 (m, 2H), 3.28-3.14 (m, 2H), 1.09-0.89 (m, 18H) LC/MS: Anal. Calcd. for [M+2H]$^+$ C$_{21}$H$_{21}$BrN$_3$O$_2$: 514.2. found 515.2 (M+1).

EXAMPLE B1

To a solution of Example B1, Step d (0.04 g, 0.063 mmol) in DMF (2 mL) was added 2-methylpropan-2-amine (0.023 g, 0.315 mmol), DIEA (0.088 mL, 0.504 mmol) and HATU (0.050 g, 0.132 mmol). After being stirred for overnight at RT, the volatile component was removed in vacuo and the residue was dissolved in DCM (5 mL×2), washed with brine, dried over Na$_2$SO$_4$ and concentrated in vacuo. The crude was submitted to reverse phase HPLC purification to afford Example B1 in a free base form as a mixture of stereoisomers (5.9 mg). LC (Condition 32 and 35): >98% homogeneity index. LC/MS (Condition 12): R$_t$=2.717 min. LC/MS: Anal. Calcd. for [M+H]$^+$ C$_{42}$H$_{54}$N$_{10}$O$_6$S: 624.4. found 625.4. $^1$H NMR (MeOD, δ=3.34 ppm, 400 MHz): δ 7.81 (d, J=8.0 Hz, 4H), 7.71 (d, J=8.5 Hz, 4H), 7.42 (s, 2H), 3.50 (s, 2H), 1.37 (br. s., 18H), 1.13 (br. s., 18H).

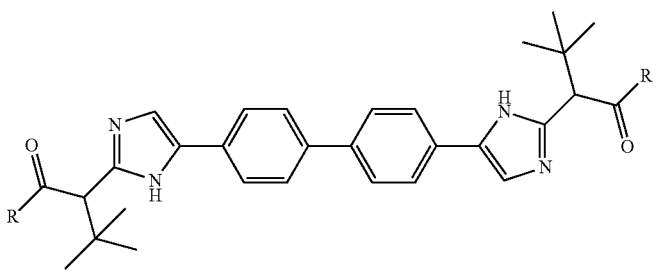

| Example | Form | R | LC & LC/MS data |
|---|---|---|---|
| B2 | Free base | (3-chlorophenyl)NH– | LC (Condition B-32 and B-35): >99% homogeneity index. LC/MS (Condition B-12): R$_t$ = 3.01 min. LC/MS: Anal. Calcd. for [M + H]$^+$ C$_{42}$H$_{54}$N$_{10}$O$_6$S: 732.2; found 733.2. $^1$H NMR (MeOD, δ = 3.34 ppm, 400 MHz): δ 7.91-7.79 (m, 6 H), 7.72 (d, J = 8.5 Hz, 4 H), 7.52-7.43 (m, 4 H), 7.33 (t, J = 8.3 Hz, 2 H), 7.13 (ddd, J = 1.0, 2.0, 8.0 Hz, 2 H), 3.77 (s, 2 H), 1.16 (s, 18 H). |

-continued

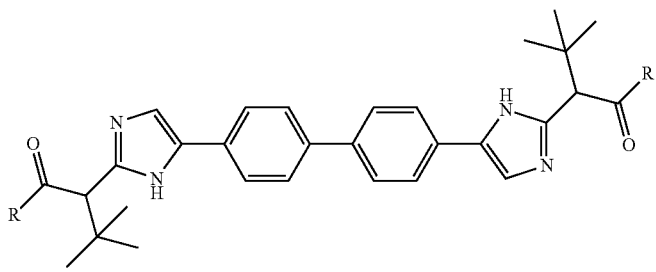

| Example | Form | R | LC & LC/MS data |
|---|---|---|---|
| B3 | Free base | -N(Et)(Et) (diethylamino) | LC (Condition B-32 and B-35): >99% homogeneity index. LC/MS (Condition B-12): $R_t$ = 2.49 min. LC/MS: Anal. Calcd. for [M + H]⁺ $C_{42}H_{54}N_{10}O_6S$: 624.4; found 625.4. ¹H NMR (DMSO-$d_6$, δ = 2.50 ppm, 400 MHz): δ 11.50 (br. s., 2 H), 7.84 (s, 4 H), 7.72-7.59 (m, 4 H), 7.47 (s, 2 H), 4.03 (s, 2 H), 3.70-3.44 (m, 5 H), 3.26-3.20 (m, 2 H), 3.13 (m, 2 H), 1.14 (br. s., 30 H). |
| B4 | Free base | pyrrolidin-1-yl | LC (Condition B-32 and B-35): >99% homogeneity index. LC/MS (Condition 12): $R_t$ = 2.35 min. LC/MS: Anal. Calcd. for [M + H]⁺ $C_{42}H_{54}N_{10}O_6S$: 620.4; found 621.5. ¹H NMR (MeOD, δ = 3.34 ppm, 400 MHz): δ 7.86-7.78 (m, 4 H), 7.76-7.66 (m, 4 H), 7.45 (s, 2 H), 4.10 (s, 2 H), 3.78-3.63 (m, 4 H), 3.50 (dt, J = 3.0, 6.8 Hz, 4 H), 2.12-1.84 (m, 8 H), 1.14 (s, 18 H). |
| B5 | Free base | cyclohexylamino | LC (Condition B-32 and B-35): >99% homogeneity index. LC/MS (Condition 12): $R_t$ = 2.81 min. LC/MS: Anal. Calcd. for [M + H]⁺ $C_{42}H_{54}N_{10}O_6S$: 676.4; found 677.4. ¹H NMR (MeOD, δ = 3.34 ppm, 400 MHz): δ 7.81 (d, J = 8.0 Hz, 4 H), 7.70 (d, J = 8.5 Hz, 4 H), 7.42 (s, 2 H), 3.82-3.67 (m, 2 H), 3.55 (s, 2 H), 2.01-1.72 (m, 8 H), 1.66 (d, J = 12.5 Hz, 2 H), 1.49-1.18 (m, 12 H), 1.10 (s, 18 H). |

Biological Activity

The NS5A synergistic inhibitory effect of test compounds can be determined using various amounts of an NS5A-targeting compound with titration of a second compound of interest. Both the NS5A-targeting compound and the second compound of interest, when tested individually versus HCV variants, are understood to be essentially inactive or weakly active and only regain synergistic inhibitory potency of 3-fold or greater inhibition when tested in combination versus HCV variants. In one embodiment, compound BMS-790052, as an NS5A-targeting compound, can be held constant at a fixed concentration of 200 nM with subsequent titration of the test compound on a variant of HCV. In one embodiment, the HCV genotype strain can be genotype 1a containing a change at amino acid 30 of the NS5A protein consisting of glutamine to glutamate. The test compound can be chosen from compounds listed above or from others present in the literature. One skilled in the art can readily test compounds in the HCV replicon cell based assay as has been demonstrated previously in the art and one can readily determine the effective concentration for 50% inhibition ($EC_{50}$) of a particular compound.

For illustration, Compound P-55, which is noted below, can be titrated in the HCV replicon cell-based assay consisting of the genotype-1a variant with glutamine 30 changed to glutamate in the NS5A protein. Titration of BMS-790052 singly would yield an $EC_{50}$ value ~200 nM while titration of P-55 singly would yield an $EC_{50}$ value >200 nM. The titration of P-55 in the presence of a fixed amount of BMS-790052 at 200 nM afforded an $EC_{50}$ values of ~2 nM for P-55 demonstrating a synergistic inhibitory effect for the combination of >100-fold. Similarly, the titration of BMS-790052 in the presence of a fixed amount of P-55 at 200 nM afforded an $EC_{50}$ values of ~2 nM for BMS-790052, demonstrating a reciprocal synergistic inhibitory effect ~100-fold for the combination (PCT/US2011/043785, filed Jul. 13, 2011), Table 3). Additional compounds can be tested in a similar manner and a ranking of synergist activities determined; these rankings for the genotype 1a Q→E variant are shown for selected compounds in the table below.

Compound P55

It is understood that the genotype is not limited to the genotype 1a variant but can encompass all genotypic variants of HCV including but not limited to HCV variants of 1b, 2a, 3a, 4a, 5a, 6a as demonstrated in commonly owned WO2012/009394. It is also understood that the synergy effect is not limited to BMS-790052 or P-55 combinations but can be derived from other combinations of NS5A-targeting compounds that by themselves have reduced or no potency towards HCV variants.

| Example number | Fold Synergistic (1a-QE) |
|---|---|
| MD-1 | >10 |
| MD-1, step b | >100 |
| MD-1, step c | <10 |
| MD-2 | >100 |
| MD-3 | >10 |
| MD-4 | <10 |
| MD-5 | >10 |
| MD-6 | >10 |
| MD-7 | <10 |
| MD-7, step b | <10 |
| MD-8 | <10 |
| MD-9 | <10 |
| MD-10 | <10 |
| MD-11 | >100 |
| MD-12 | >10 |
| MD-13 | >100 |
| MD-14 | <10 |
| MD-15 | <10 |
| MD-16 | <10 |
| MD-17 | <10 |
| MD-18 | >10 |
| MD-19 | >100 |
| MD-20 | >10 |
| MD-21 | >100 |
| MD-22 | >100 |
| MD-23 | >100 |
| MD-24 | >10 |
| MD-25 | >10 |
| MD-26 | >10 |
| MD-27 | >10 |
| MD-28 | >100 |
| MD-29 | <10 |
| MD-30 | <10 |
| MD-31 | <10 |
| MD-32 | >100 |
| MD-33 | <10 |
| MD-34 | >100 |
| MD-35 | >10 |
| MD-36 | >10 |
| MD-37 | >10 |
| MD-38 | >100 |
| MD-39 | >10 |
| MD-40 | >100 |
| MD-41 | >10 |
| MD-42 | >10 |
| MD-43 | >10 |
| MD-44 | >10 |
| MD-45 | >100 |
| MD-46 | >10 |
| MD-47 | >100 |

-continued

| Example number | Fold Synergistic (1a-QE) |
|---|---|
| MD-48 | <10 |
| MD-49 | >10 |
| MD-50 | <10 |
| MD-51 | >10 |
| MD-52 | >100 |
| MD-53 | <10 |
| MD-54 | >10 |
| MD-55 | <10 |
| MD-56 | <10 |
| MD-57 | >10 |
| MD-58 | >10 |
| MD-59 | >10 |
| MD-60 | >10 |
| MD-61 | <10 |
| B1 | >100 |
| B2 | <10 |
| B3 | >10 |
| B4 | <10 |
| B5 | <10 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A combination comprising an NS5A-targeting compound and an NS5A synergist, which, when administered, provides synergistic anti-HCV activity against variants that contain mutation(s) conferring resistance to the NS5A-targeting compound alone, wherein the NS5A-targeting compound is BMS-790052:

BMS-790052

-continued

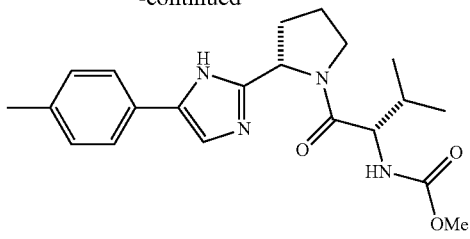

and wherein the NS5A synergist is a compound of formula (I):

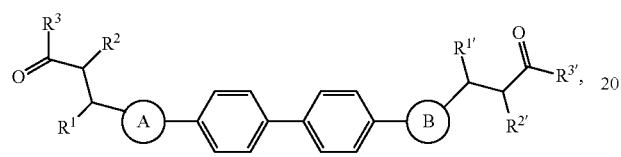

or a pharmaceutically acceptable salt thereof, wherein A and B are independently selected from

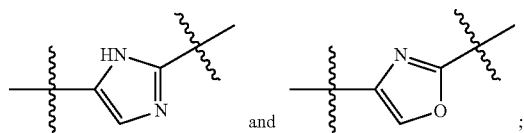 [SMILES: *c1cnc(*)[nH]1 ; *c1coc(*)n1]

$R^1$ is selected from alkoxy, alkyl, haloalkyl, and hydroxy;
$R^2$ is hydrogen; or, alternatively,
$R^1$ and $R^2$, together with the carbon atoms to which they are attached, form a dioxolanyl ring, wherein the dioxolanyl-ring is optionally substituted with one or two methyl groups;
$R^{1'}$ is selected from alkoxy, alkyl, haloalkyl, and hydroxy;
$R^{2'}$ is hydrogen; or, alternatively,
$R^{1'}$ and $R^{2'}$, together with the carbon atoms to which they are attached, form a dioxolanyl ring, wherein the dioxolanyl ring is optionally substituted with two methyl groups; and
$R^3$ and $R^{3'}$ are independently selected from alkoxy, hydroxy, and —$NR^aR^b$;
$R^a$ and $R^b$ are independently selected from hydrogen, alkoxycarbonylalkyl, alkyl, polycycloalkyl, (polycycloalkyl)alkyl, cycloalkyl, (cycloalkyl)alkyl, hydroxyalkyl, —$NR^cR^d$, ($NR^cR^d$)alkyl, ($NR^cR^d$)carbonylalkyl, phenylalkyl, and pyranyl, wherein the cycloalkyl, the cycloalkyl part of the (cycloalkyl)alkyl, and the phenyl part of the phenylalkyl is optionally substituted with one or two groups independently selected from alkoxy, alkoxyalkyl, aminocarbonyl, cyano, halo, hydroxy, and phenyl; and wherein the alkyl part of the ($NR^cR^d$)alkyl is optionally substituted with a hydroxy group; or, alternatively,
$R^a$ and $R^b$, together with the nitrogen atom to which they are attached, form a ring selected from morpholine, piperidine, and piperazine wherein each ring is optionally substituted with one or two groups selected from alkoxycarbonyl, alkyl, halo, oxo, and phenyl optionally substituted with halo; and
one of $R^c$ and $R^d$ is selected from hydrogen and alkyl and the other is selected from hydrogen, alkoxycarbonyl, and alkyl; or, alternatively,
$R^c$ and $R^d$, together with the nitrogen atom to which they are attached, form an oxazolidinone ring.

2. The combination of claim 1 wherein the compound of formula (I) is selected from

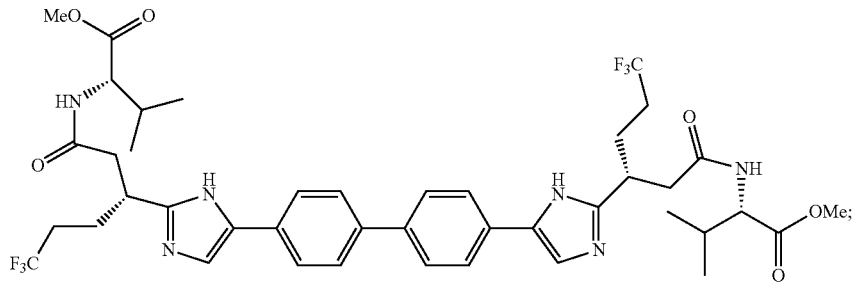

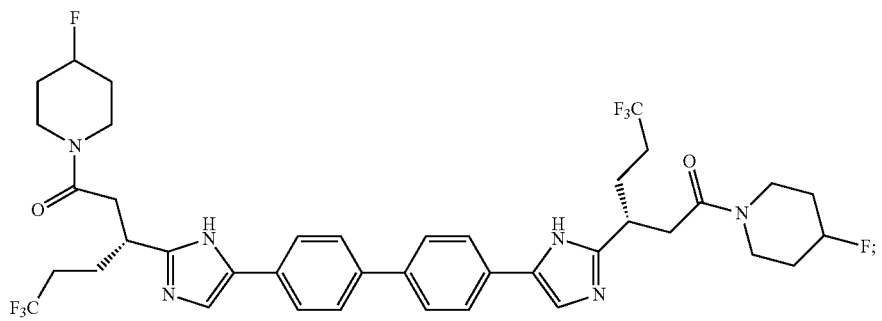

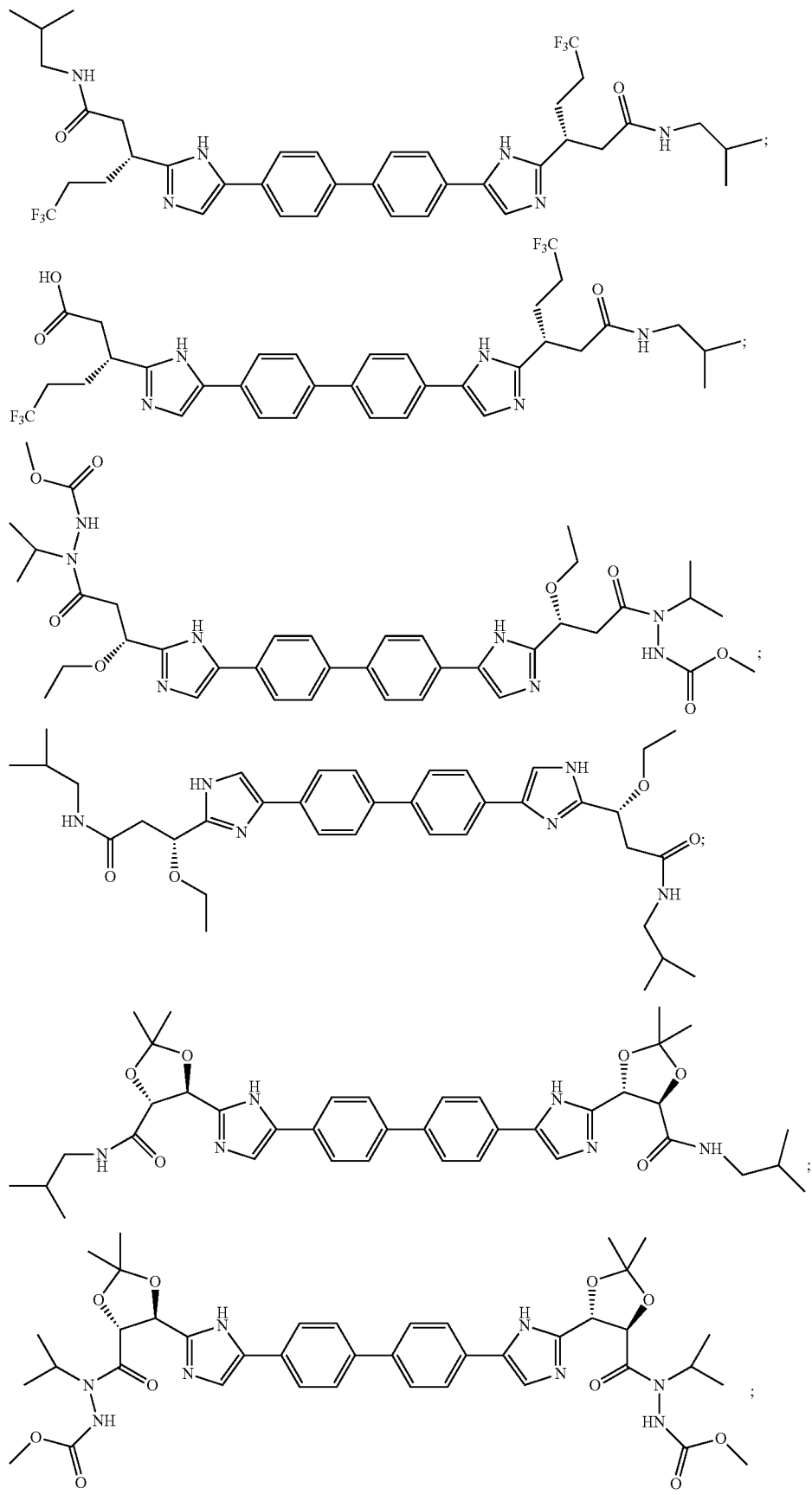

-continued
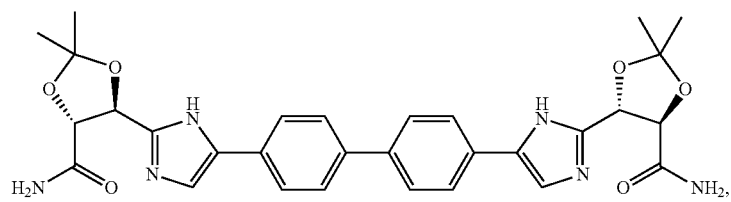
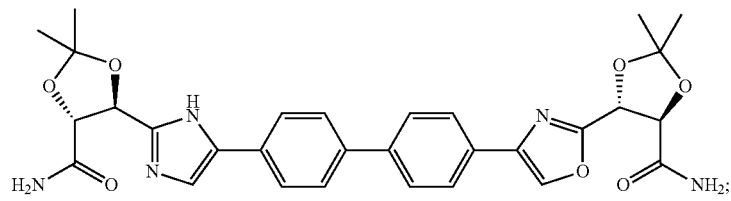
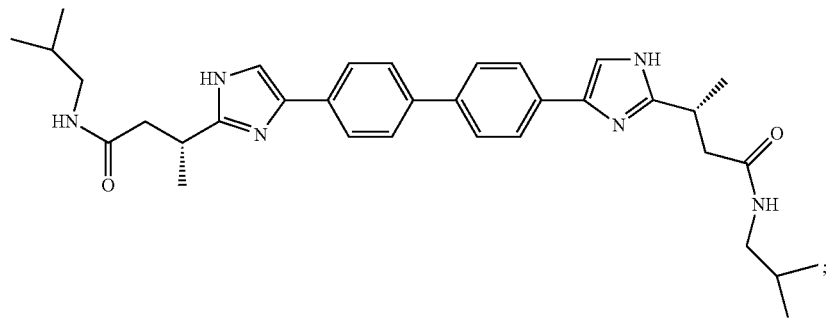
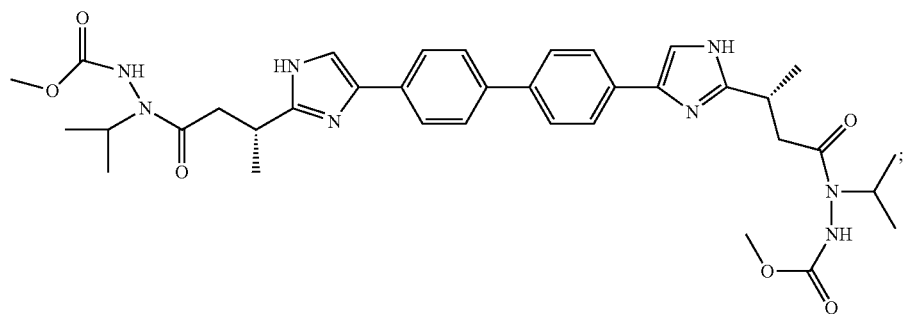
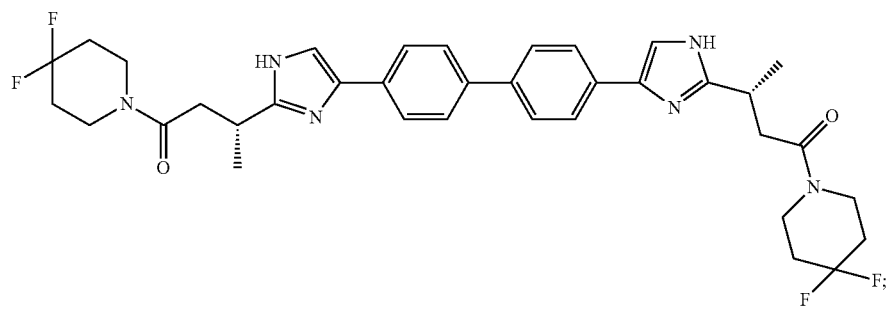
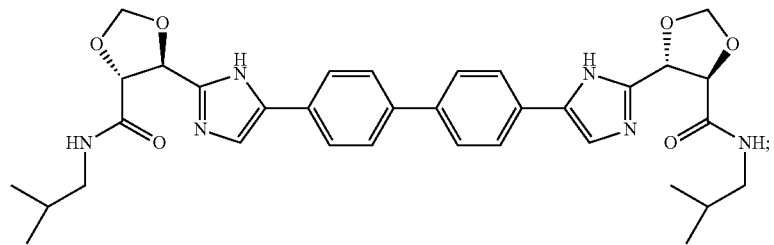

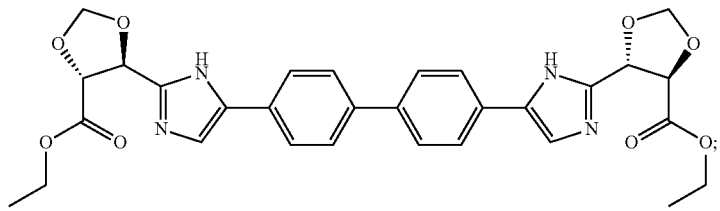
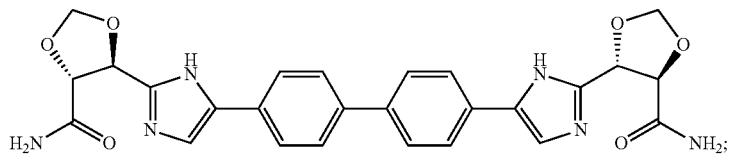
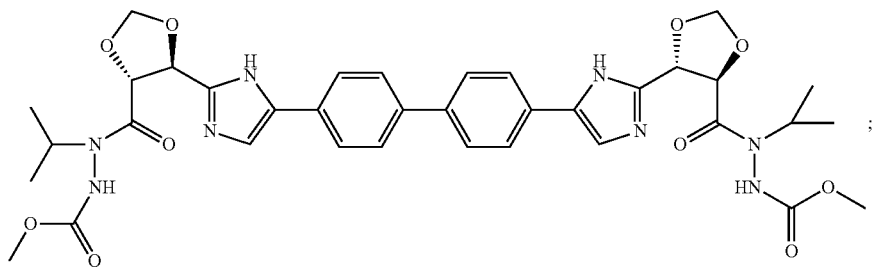
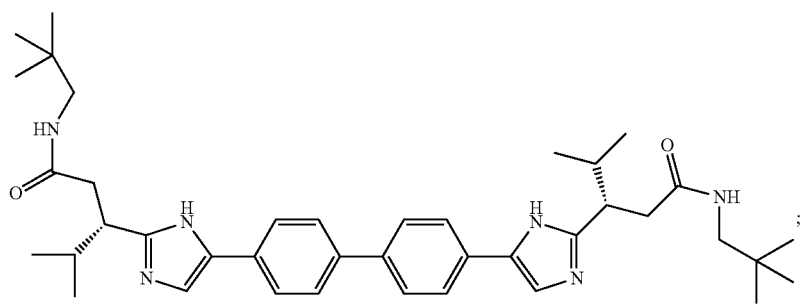
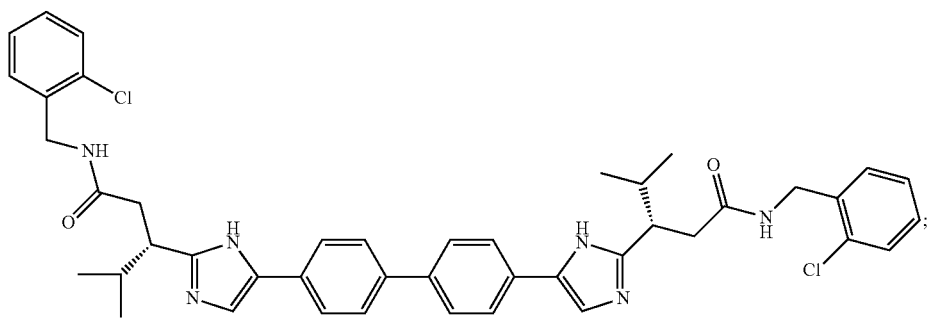
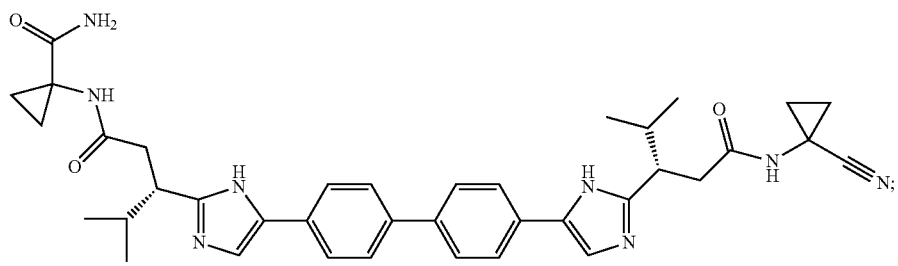

-continued
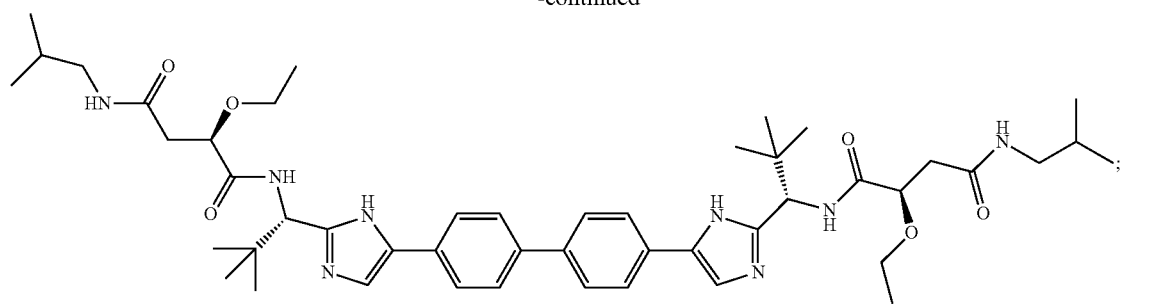
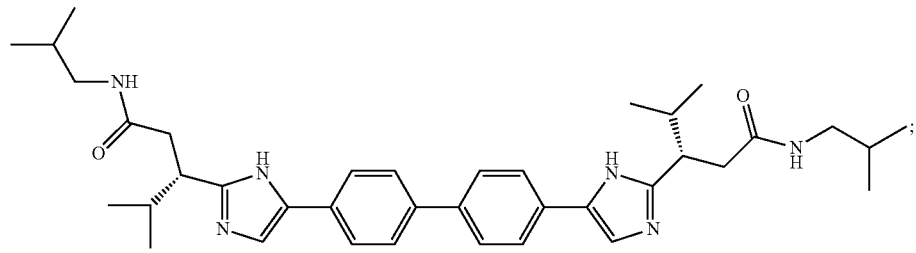
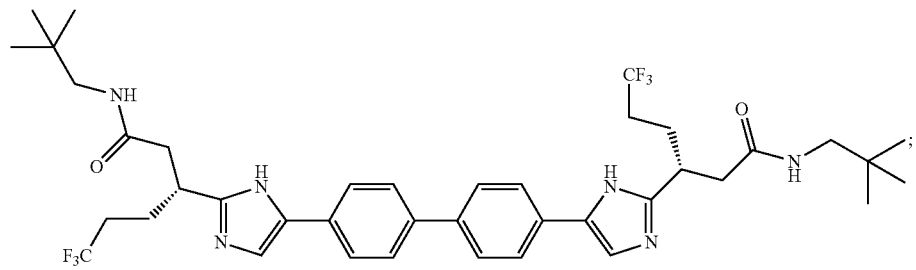
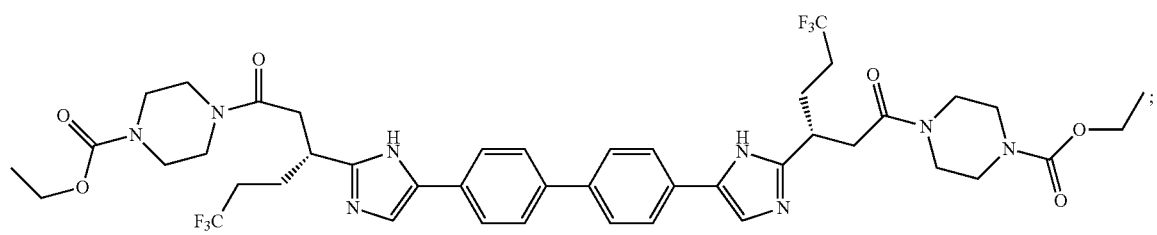
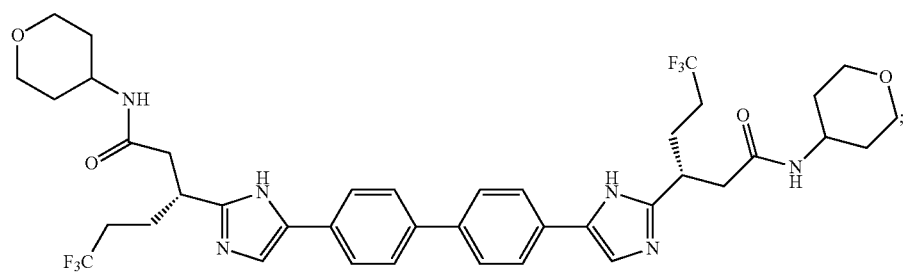
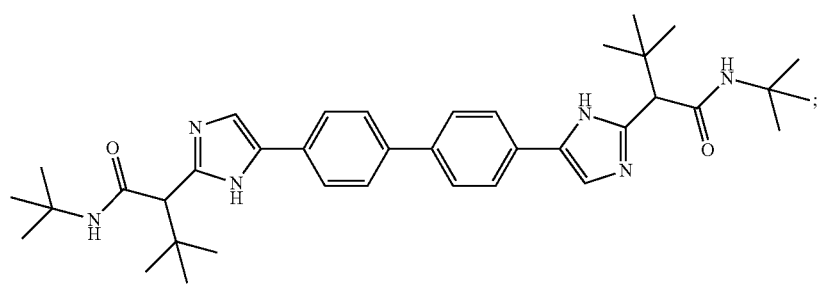

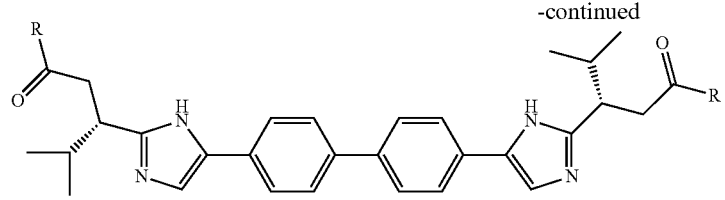
| R |
|---|
| 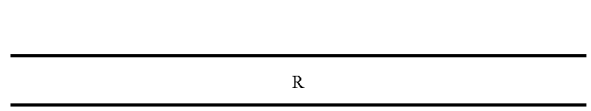 |
| 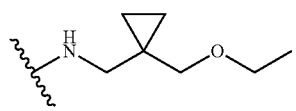 [SMILES: *NCC1(COCC)CC1] |
| 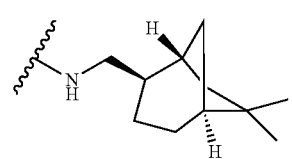 [SMILES: *NC[C@@H]1CC[C@H]2C[C@@H]1CC2(C)C] |
| 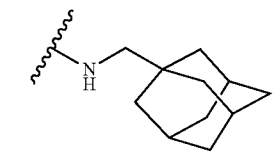 [SMILES: *NCC12CC3CC(CC(C3)C1)C2] |
| 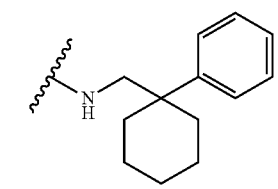 [SMILES: *NCC1(c2ccccc2)CCCCC1] |
| 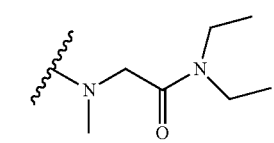 [SMILES: *N(C)CC(=O)N(CC)CC] |
| 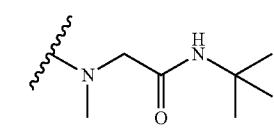 [SMILES: *N(C)CC(=O)NC(C)(C)C] |
| 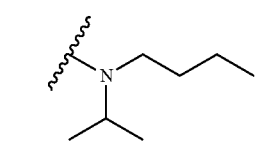 [SMILES: *N(CCCC)C(C)C] |
| 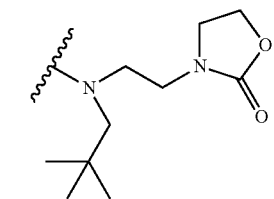 [SMILES: *N(CCN1CCOC1=O)CC(C)(C)C] |
-continued
| R |
|---|
| 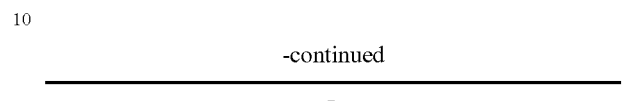 |
| 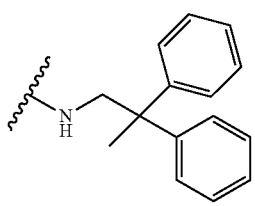 [SMILES: *NCC(C)(c1ccccc1)c1ccccc1] |
| 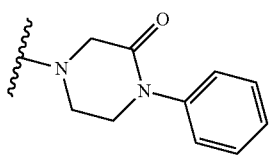 [SMILES: *N1CCN(c2ccccc2)C(=O)C1] |
| 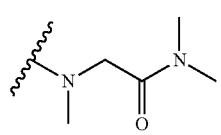 [SMILES: *N(C)CC(=O)N(C)C] |
| 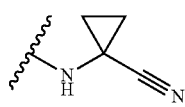 |
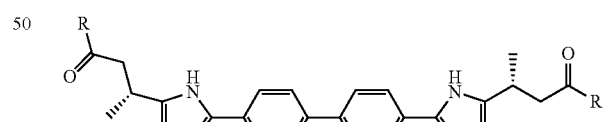
| R |
|---|
| 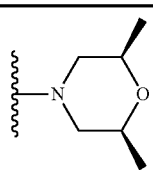 |

91
-continued

| R |
|---|
| (chemical structures) |

92
-continued

| R |
|---|
| (chemical structures) |

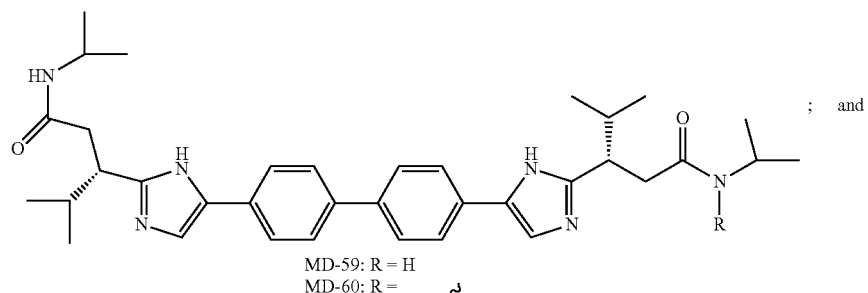

MD-59: R = H
MD-60: R = 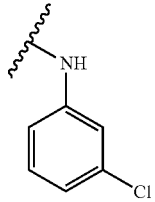 [SMILES: *Nc1cccc(Cl)c1]

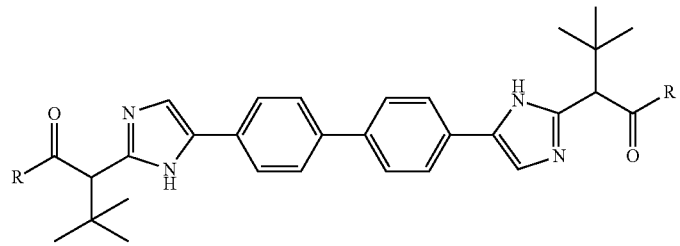

| R |
|---|
| 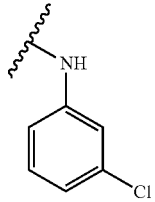 [SMILES: *Nc1cccc(Cl)c1] |
| 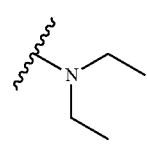 [SMILES: *N(CC)CC] |
| 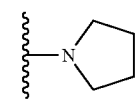 [SMILES: *N1CCCC1] |
| 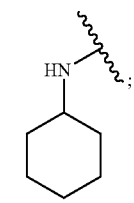 [SMILES: *NC1CCCCC1] | or a pharmaceutically acceptable salt thereof.

3. A composition comprising the combination of claim 1 and one or more pharmaceutically acceptable carriers.

4. The composition of claim 3 further comprising one or two additional compounds having anti-HCV activity.

5. The composition of claim 4 wherein at least one of the additional compounds is an interferon or a ribavirin.

6. The composition of claim 5 wherein the interferon is selected from interferon alpha 2B, pegylated interferon alpha, pegylated interferon lambda, consensus interferon, interferon alpha 2A, and lymphoblastoid interferon tau.

7. The composition of claim 4 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

8. A method of treating an HCV infection in a patient, comprising administering to the patient a therapeutically effective amount of a combination of claim 1, or a pharmaceutically acceptable salt thereof.

9. The method of claim 8 further comprising administering one or two additional compounds having anti-HCV activity prior to, after or simultaneously with the combination, or a pharmaceutically acceptable salt thereof.

10. The method of claim 9 wherein at least one of the additional compounds is an interferon or a ribavirin.

11. The method of claim 10 wherein interferon is selected from interferon alpha 2B, pegylated interferon alpha, pegylated interferon lambda, consensus interferon, interferon alpha 2A, and lymphoblastoid interferon tau.

12. The method of claim 9 wherein at least one of the additional compounds is effective to inhibit the function of a target selected from HCV protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 9,775,831 B2
APPLICATION NO. : 14/904852
DATED : October 3, 2017
INVENTOR(S) : Saulnier et al.

Page 1 of 1

It is certified that error appears in the above-identified patent and that said Letters Patent is hereby corrected as shown below:

In the Claims

Claim 2, Columns 83-84, Lines 1-5 delete:

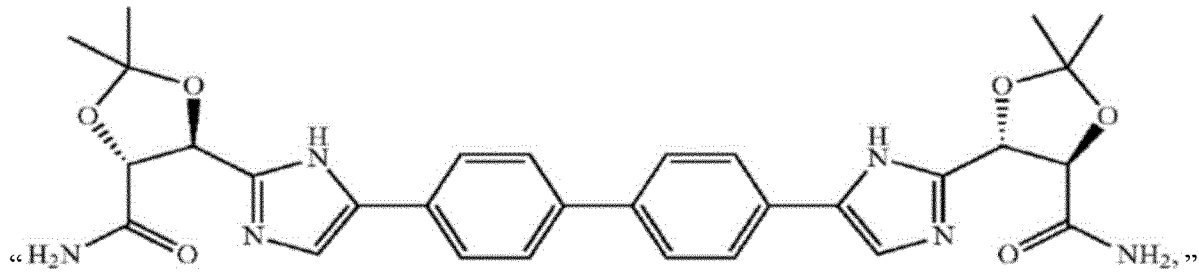

" "

And insert:

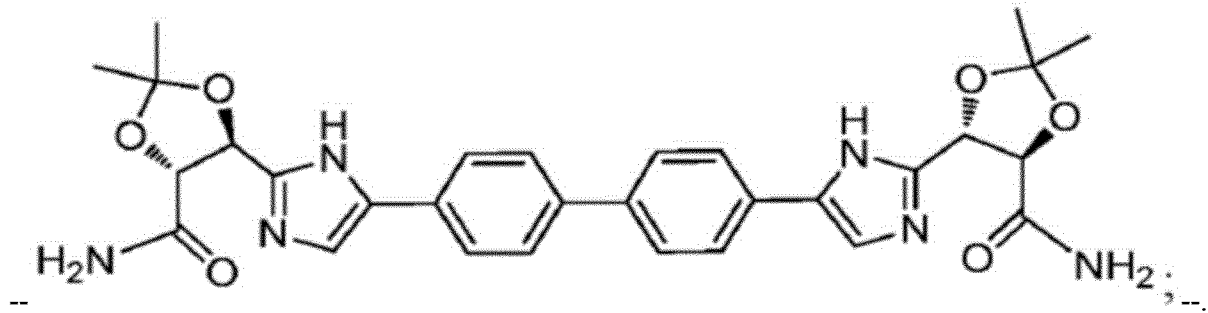

-- --

Signed and Sealed this
Eleventh Day of December, 2018

Andrei Iancu
*Director of the United States Patent and Trademark Office*